(12) United States Patent
Hayter et al.

(10) Patent No.: US 9,974,472 B2
(45) Date of Patent: May 22, 2018

(54) TEMPERATURE-COMPENSATED ANALYTE MONITORING DEVICES, SYSTEMS, AND METHODS THEREOF

(75) Inventors: Gary A. Hayter, Oakland, CA (US); Daniel M. Bernstein, El Granada, CA (US); Martin J. Fennell, Concord, CA (US); Michael R. Love, Pleasanton, CA (US); Kenneth J. Doniger, Menlo Park, CA (US); Songbiao Zhang, Fremont, CA (US); Mark K. Sloan, Hayward, CA (US); Hyun Cho, Berkeley, CA (US); Theodore J. Kunich, Pleasanton, CA (US); Jean-Pierre Cole, Tracy, CA (US); Christopher A. Thomas, San Leandro, CA (US); Erwin S. Budiman, Fremont, CA (US); David L. Li, Fullerton, CA (US); Royce Cheng, San Francisco, CA (US); Udo Hoss, Castro Valley, CA (US)

(73) Assignee: Abbott Diabetes Care Inc., Alameda, CA (US)

( * ) Notice: Subject to any disclaimer, the term of this patent is extended or adjusted under 35 U.S.C. 154(b) by 967 days.

(21) Appl. No.: 13/526,394

(22) Filed: Jun. 18, 2012

(65) Prior Publication Data
US 2013/0158376 A1 Jun. 20, 2013

Related U.S. Application Data

(60) Provisional application No. 61/497,821, filed on Jun. 16, 2011.

(51) Int. Cl.
*A61B 5/05* (2006.01)
*A61B 5/145* (2006.01)
*A61B 5/01* (2006.01)
*A61B 5/00* (2006.01)
*A61B 5/1473* (2006.01)

(52) U.S. Cl.
CPC ............ *A61B 5/14532* (2013.01); *A61B 5/01* (2013.01); *A61B 5/14503* (2013.01); *A61B 5/7225* (2013.01); *A61B 5/1473* (2013.01); *A61B 2560/0252* (2013.01); *A61B 2562/0271* (2013.01)

(58) Field of Classification Search
CPC ....... A61B 5/14532; A61B 5/145; A61B 5/00; A61B 5/01; A61B 5/1473; A61B 5/7225; A61B 5/14503; A61B 2560/0252; A61B 2562/0271
USPC ........................................ 600/345, 347, 365
See application file for complete search history.

(56) References Cited

U.S. PATENT DOCUMENTS

| 3,729,343 A | 4/1973 | Thomas |
| 4,545,382 A | 10/1985 | Higgins et al. |
| 4,711,245 A | 12/1987 | Higgins et al. |
| 5,262,035 A | 11/1993 | Gregg et al. |

(Continued)

FOREIGN PATENT DOCUMENTS

WO 2010/040090 4/2010

*Primary Examiner* — Christian Jang
*Assistant Examiner* — Eric Messersmith
(74) *Attorney, Agent, or Firm* — Vorys, Sater, Seymour and Pease LLP

(57) ABSTRACT

Methods, devices and systems related providing accurate glucose levels in view of temperatures that may adversely affect glucose value.

16 Claims, 12 Drawing Sheets

(56) References Cited

U.S. PATENT DOCUMENTS

| | | |
|---|---|---|
| 5,262,305 A | 11/1993 | Heller et al. |
| 5,264,014 A | 11/1993 | Lannefors et al. |
| 5,264,104 A | 11/1993 | Gregg et al. |
| 5,320,715 A | 6/1994 | Berg |
| 5,320,725 A | 6/1994 | Gregg et al. |
| 5,356,786 A | 10/1994 | Heller et al. |
| 5,509,410 A | 4/1996 | Hill et al. |
| 5,593,852 A | 1/1997 | Heller et al. |
| 5,601,435 A | 2/1997 | Quy |
| 5,628,890 A | 5/1997 | Carter et al. |
| 5,820,551 A | 10/1998 | Hill et al. |
| 5,822,715 A | 10/1998 | Worthington et al. |
| 5,899,855 A | 5/1999 | Brown |
| 5,918,603 A | 7/1999 | Brown |
| 6,071,391 A | 6/2000 | Gotoh et al. |
| 6,120,676 A | 9/2000 | Heller et al. |
| 6,121,009 A | 9/2000 | Heller et al. |
| 6,143,164 A | 11/2000 | Heller et al. |
| 6,144,837 A | 11/2000 | Quy |
| 6,161,095 A | 12/2000 | Brown |
| 6,175,752 B1 | 1/2001 | Say et al. |
| 6,270,455 B1 | 8/2001 | Brown |
| 6,284,478 B1 | 9/2001 | Heller et al. |
| 6,299,757 B1 | 10/2001 | Feldman et al. |
| 6,338,790 B1 | 1/2002 | Feldman et al. |
| 6,377,894 B1 | 4/2002 | Deweese et al. |
| 6,461,496 B1 | 10/2002 | Feldman et al. |
| 6,503,381 B1 | 1/2003 | Gotoh et al. |
| 6,514,460 B1 | 2/2003 | Fendrock |
| 6,514,718 B2 | 2/2003 | Heller et al. |
| 6,540,891 B1 | 4/2003 | Stewart et al. |
| 6,560,471 B1 | 5/2003 | Heller et al. |
| 6,591,125 B1 | 7/2003 | Buse et al. |
| 6,592,745 B1 | 7/2003 | Feldman et al. |
| 6,600,997 B2 | 7/2003 | Deweese et al. |
| 6,616,819 B1 | 9/2003 | Liamos et al. |
| 6,618,934 B1 | 9/2003 | Feldman et al. |
| 6,650,471 B2 | 11/2003 | Doi |
| 6,676,816 B2 | 1/2004 | Mao et al. |
| 6,730,200 B1 | 5/2004 | Stewart et al. |
| 6,736,957 B1 | 5/2004 | Forrow et al. |
| 6,746,582 B2 | 6/2004 | Heller et al. |
| 6,749,740 B2 | 6/2004 | Liamos et al. |
| 6,764,581 B1 | 7/2004 | Forrow et al. |
| 6,773,671 B1 | 8/2004 | Lewis et al. |
| 6,881,551 B2 | 4/2005 | Heller et al. |
| 6,893,545 B2 | 5/2005 | Gotoh et al. |
| 6,942,518 B2 | 9/2005 | Liamos et al. |
| 7,041,468 B2 | 5/2006 | Drucker et al. |
| 7,167,818 B2 | 1/2007 | Brown |
| 7,299,082 B2 | 11/2007 | Feldman et al. |
| 7,768,386 B2 | 8/2010 | Hayter et al. |
| 7,811,231 B2 | 10/2010 | Jin et al. |
| 7,835,925 B2 | 11/2010 | Roe et al. |
| 2003/0169800 A1* | 9/2003 | Pompei .................. 374/121 |
| 2004/0186365 A1 | 9/2004 | Jin et al. |
| 2005/0245839 A1* | 11/2005 | Stivoric et al. ............... 600/549 |
| 2006/0025662 A1 | 2/2006 | Buse et al. |
| 2006/0091006 A1 | 5/2006 | Wang et al. |
| 2007/0068807 A1 | 5/2007 | Feldman et al. |
| 2007/0095661 A1 | 5/2007 | Wang et al. |
| 2007/0108048 A1 | 5/2007 | Wang et al. |
| 2007/0199818 A1 | 8/2007 | Petyt et al. |
| 2008/0066305 A1 | 3/2008 | Wang et al. |
| 2008/0102441 A1 | 5/2008 | Chen et al. |
| 2008/0148873 A1 | 6/2008 | Wang |
| 2008/0267823 A1 | 10/2008 | Wang et al. |
| 2008/0300919 A1 | 12/2008 | Charlton et al. |
| 2009/0030641 A1* | 1/2009 | Fjield ................ A61B 5/14532 702/104 |
| 2009/0036747 A1* | 2/2009 | Hayter et al. ................. 600/300 |
| 2009/0275815 A1* | 11/2009 | Bickoff et al. ................ 600/345 |
| 2010/0198034 A1 | 8/2010 | Thomas et al. |
| 2010/0268475 A1 | 10/2010 | Kunimasa |
| 2010/0324392 A1 | 12/2010 | Yee et al. |
| 2010/0325868 A1 | 12/2010 | Wang et al. |
| 2010/0326842 A1 | 12/2010 | Mazza et al. |
| 2011/0105873 A1 | 5/2011 | Feldman et al. |
| 2011/0152658 A1* | 6/2011 | Peyser et al. ................. 600/365 |
| 2012/0028283 A1 | 2/2012 | Hoss et al. |
| 2012/0150005 A1 | 6/2012 | Hoss et al. |
| 2012/0157801 A1 | 6/2012 | Hoss et al. |
| 2012/0165635 A1* | 6/2012 | Radhakrishnan et al. .... 600/347 |

* cited by examiner

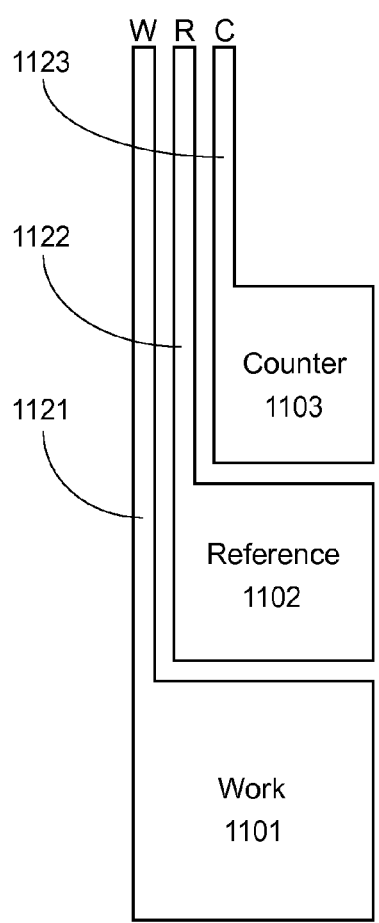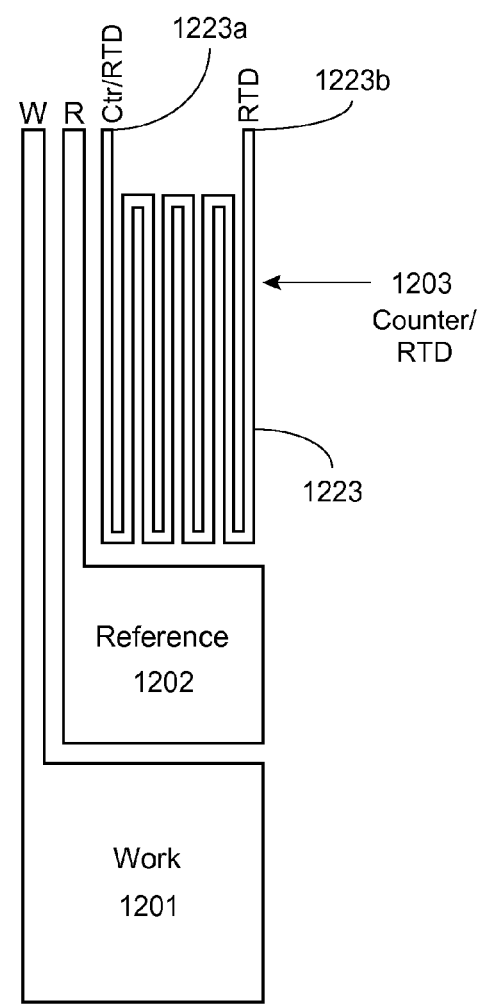
FIG. 10
FIG. 11

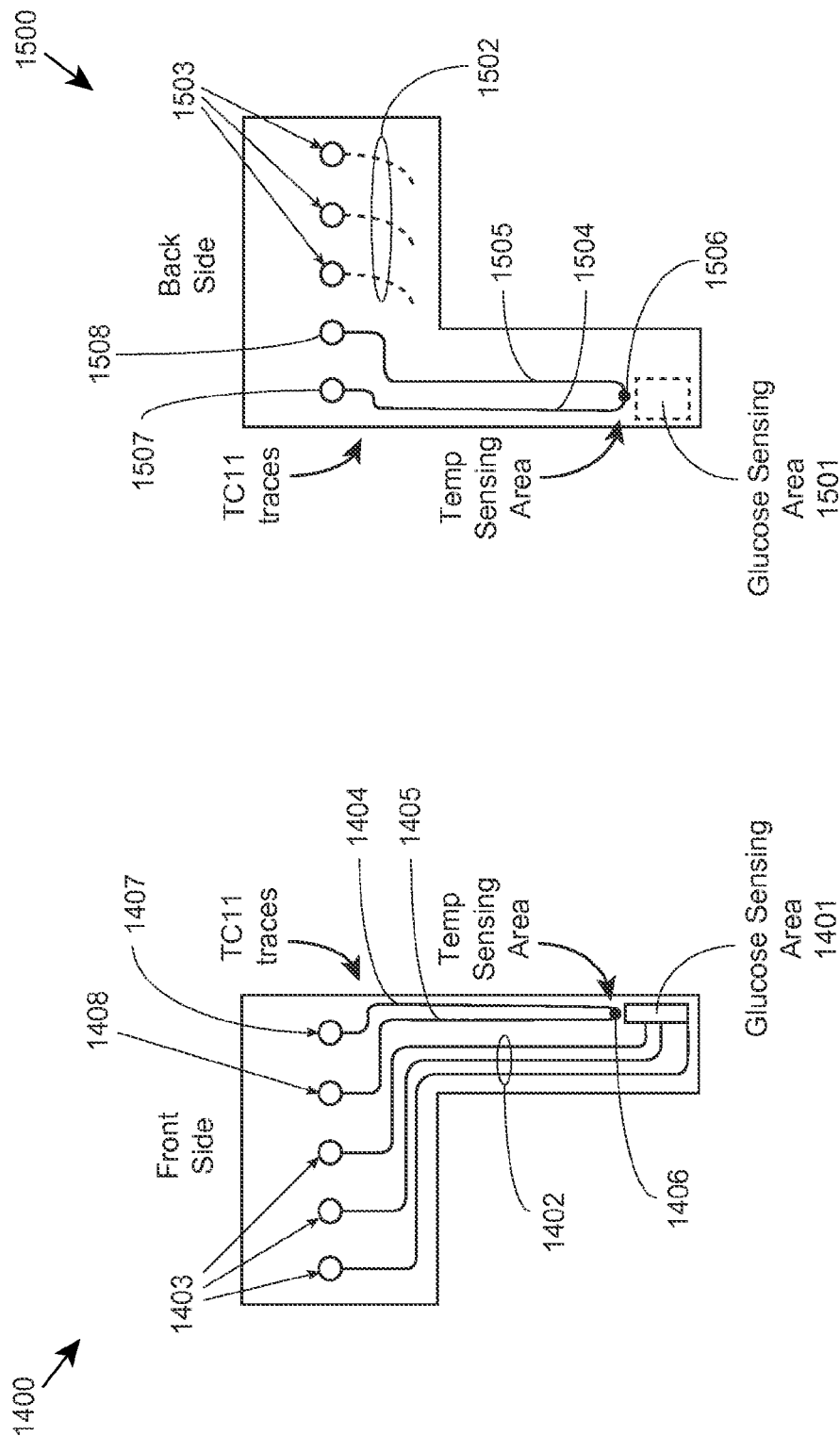

TEMPERATURE-COMPENSATED ANALYTE MONITORING DEVICES, SYSTEMS, AND METHODS THEREOF

CROSS-REFERENCE TO RELATED APPLICATION

This application claims the benefit of priority under 35 U.S.C. § 119(e) to U.S. Provisional Patent Application No. 61/497,821 filed Jun. 16, 2011, the disclosure of which is incorporated by reference herein in its entirety.

INCORPORATION BY REFERENCE

The following patents, applications and/or publications are incorporated herein by reference for all purposes: U.S. Pat. No. 7,041,468; U.S. Pat. No. 5,356,786; U.S. Pat. No. 6,175,752; U.S. Pat. No. 6,560,471; U.S. Pat. No. 5,262,035; U.S. Pat. No. 6,881,551; U.S. Pat. No. 6,121,009; U.S. Pat. No. 7,167,818; U.S. Pat. No. 6,270,455; U.S. Pat. No. 6,161,095; U.S. Pat. No. 5,918,603; U.S. Pat. No. 6,144,837; U.S. Pat. No. 5,601,435; U.S. Pat. No. 5,822,715; U.S. Pat. No. 5,899,855; U.S. Pat. No. 6,071,391; U.S. Pat. No. 6,120,676; U.S. Pat. No. 6,143,164; U.S. Pat. No. 6,299,757; U.S. Pat. No. 6,338,790; U.S. Pat. No. 6,377,894; U.S. Pat. No. 6,600,997; U.S. Pat. No. 6,773,671; U.S. Pat. No. 6,514,460; U.S. Pat. No. 6,592,745; U.S. Pat. No. 5,628,890; U.S. Pat. No. 5,820,551; U.S. Pat. No. 6,736,957; U.S. Pat. No. 4,545,382; U.S. Pat. No. 4,711,245; U.S. Pat. No. 5,509,410; U.S. Pat. No. 6,540,891; U.S. Pat. No. 6,730,200; U.S. Pat. No. 6,764,581; U.S. Pat. No. 6,299,757; U.S. Pat. No. 6,461,496; U.S. Pat. No. 6,503,381; U.S. Pat. No. 6,591,125; U.S. Pat. No. 6,616,819; U.S. Pat. No. 6,618,934; U.S. Pat. No. 6,676,816; U.S. Pat. No. 6,749,740; U.S. Pat. No. 6,893,545; U.S. Pat. No. 6,942,518; U.S. Pat. No. 6,514,718; U.S. Pat. No. 5,264,014; U.S. Pat. No. 5,262,305; U.S. Pat. No. 5,320,715; U.S. Pat. No. 5,593,852; U.S. Pat. No. 6,746,582; U.S. Pat. No. 6,284,478; U.S. Pat. No. 7,299,082; U.S. Patent Application No. 61/149,639, entitled "Compact On-Body Physiological Monitoring Device and Methods Thereof", U.S. patent application Ser. No. 11/461,725, filed Aug. 1, 2006, entitled "Analyte Sensors and Methods"; U.S. patent application Ser. No. 12/495,709, filed Jun. 30, 2009, entitled "Extruded Electrode Structures and Methods of Using Same"; U.S. patent application Ser. No. 12/698,124, filed Feb. 1, 2010, entitled "Compact On-Body Physiological Monitoring Devices and Methods Thereof"; U.S. patent application Ser. No. 12/698,129, filed Feb. 1, 2010, entitled "Analyte Sensor And Apparatus For Insertion Of The Sensor"; U.S. Patent Application Publication No. US2004/0186365; U.S. Patent Application Publication No. 2007/0095661; U.S. Patent Application Publication No. 2006/0091006; U.S. Patent Application Publication No. 2006/0025662; U.S. Patent Application Publication No. 2008/0267823; U.S. Patent Application Publication No. 2007/0108048; U.S. Patent Application Publication No. 2008/0102441; U.S. Patent Application Publication No. 2008/0066305; U.S. Patent Application Publication No. 2007/0199818; U.S. Patent Application Publication No. 2008/0148873; U.S. Patent Application Publication No. 2007/0068807; US patent Application Publication No. 2010/0198034; U.S. Patent Application Publication No. 2010/0325868; and U.S. Provisional Application No. 61/149,639 titled "Compact On-Body Physiological Monitoring Device and Methods Thereof"; U.S. Provisional Patent Application No. 61/368,553, filed Jul. 28, 2010, entitled, "Analyte Sensors Having Temperature Independent Membranes"; U.S. Provisional Patent Application No. 61/415,174, filed Nov. 18, 2010, entitled, "Adaptor for On-Body Self-Powered Analyte Monitoring System"; and U.S. Provisional Patent Application No. 61/421,371, filed Dec. 9, 2010, entitled, "Analyte Sensors with Reduced Sensitivity Variation", the disclosures of each of which are incorporated herein by reference in their entirety.

BACKGROUND

In vivo analyte monitoring systems include an in vivo analyte sensor. At least a portion of the sensor is positioned beneath the skin surface of a user to contact bodily fluid to monitor one or more analytes in the fluid over a period of time. This is also referred to as continuous analyte monitoring in that the sensor remains positioned in the user for a continuous period of time.

Analyte sensors may have temperature dependencies and the sensor signals produced by the sensors are may then be affected by temperature changes. An error caused by temperature measurement may lead to an associated error in analyte measurements, such as blood glucose measurements.

SUMMARY

Aspects of the present disclosure relate to analyte monitoring systems, devices, and methods thereof related to temperature compensation, such as temperature compensated glucose values. Included are devices, computer-implemented methods, and systems that determine temperature of an environment surrounding an in vivo glucose sensor, and whether the temperature adversely affects the in vivo analyte sensor glucose data, e.g., the temperature is too high and/or too low. If the temperature may adversely affect the glucose data, the system may be responsive to the temperature information so that erroneous glucose information is not presented to the user. Determined glucose values may be modified or not depending on the temperature and/or glucose values may be displayed to a user or not depending on the temperature. Temperature data may be in vivo temperature data (e.g., obtained at the location of a working electrode of an in vivo analyte sensor during a sensing process such as on or near the body-inserted sensor portion) and/or may be ambient temperature, and/or may be temperature of a processor of a sensor electronics unit such as a sensor control unit and/or may be skin surface temperature.

In certain embodiments, a processor of a glucose monitoring system may always compensate in vivo glucose sensor data based on temperature, but a display device will not display the temperature-compensated glucose values if the temperature is determined to exceed a predetermined threshold, or a processor of a glucose monitoring system will only compensate in vivo glucose sensor data based on temperature if temperature is determined to be within a predetermined range, and a display device will display temperature un-compensated glucose values if the temperature is determined to be within a first range predetermined range and will display temperature-compensated glucose values if temperature is determined to be in a second range.

Embodiments include obtaining glucose data from an in vivo glucose sensor, obtaining temperature data from one or more temperature sensors, comparing the temperature data to a predetermined temperature threshold, and determining a temperature-compensated glucose value if the temperature data does not exceed the predetermined threshold, and not determining a temperature-compensated glucose value if the temperature data does exceed the predetermined threshold. Certain embodiments may include not compensating for temperature if the temperature data is within a predetermined range. In other words, glucose values may be adjusted or not based on temperature data obtained at the same or substantially same time as the glucose data.

Embodiments include methods that include displaying information responsive to obtained temperature data. Embodiments include obtaining glucose data from an in vivo glucose sensor, obtaining temperature data from one or more temperature sensors, comparing the temperature data to a predetermined temperature threshold, and displaying on a user interface device a temperature-compensated glucose value if the temperature data does not exceed the predetermined threshold, and not displaying a temperature-compensated glucose value if the temperature data does exceed the predetermined threshold. In such embodiments, glucose values may be determined or not, but in any event are not communicated to a user if a temperature threshold is exceeded.

Embodiments include computer systems that analyze temperature data for its affects to a glucose sensor. Certain embodiments include an in vivo glucose sensor, at least one temperature sensor, a sensor electronics unit that receives glucose data from the in vivo analyte sensor, and a receiver unit that receives glucose data from the electronics unit. A display may be included with the sensor electronics unit or receiver unit. At least one processor of the electronics unit and/or the receiver unit includes instructions to process temperature data of the at least one temperature sensor and in vivo analyte sensor data of the in vivo analyte sensor, and compare the temperature data to a predetermined temperature threshold, and determine a temperature-compensated glucose value if the temperature data does not exceed the predetermined threshold, and not determine a temperature-compensated glucose value if the temperature data does exceed the predetermined threshold. The at least one processor may include instructions to not compensate for temperature if the temperature data is within a predetermined range. In other words, it may cause glucose values to be adjusted or not based on temperature data obtained at the same or substantially same time as the glucose data. In display embodiments, the one or more processors may include instructions to cause the display to display or not to display information responsive to obtained temperature data. At least one processor includes instructions to process temperature data of the at least one temperature sensor and in vivo analyte sensor data of the in vivo glucose sensor in include obtaining glucose data from an in vivo glucose sensor, and compare the temperature data to a predetermined temperature threshold, and display on the display a temperature-compensated glucose value if the temperature data does not exceed the predetermined threshold, and not display a temperature-compensated glucose value if the temperature data does exceed the predetermined threshold. In such embodiments, the one or more processors may cause glucose values to be determined or not, but in any event are not communicated to a user on a display device if a temperature threshold is exceeded.

In some aspects of the present disclosure, methods of detecting and/or determining an analyte level by compensating for ambient temperature using a temperature sensor (e.g., coupled to an in vivo analyte sensor) are provided. The methods includes receiving a sensor signal (e.g., sensor information, such as current, voltage, etc.) derived from an in vivo analyte sensor; detecting a temperature measurement from a temperature sensor; determining, with a processor, whether a temperature threshold requirement is exceeded based on the temperature measurement; and determining, with the processor, a temperature-compensated analyte sensor signal. When the threshold requirement is not exceeded, the temperature-compensated analyte sensor signal is determined using the temperature measurement. Only when the threshold requirement is exceeded, the temperature-compensated analyte sensor signal is determined using an ambient-compensated temperature that is derived by compensating the temperature measurement for ambient temperature.

In some aspects of the present disclosure, analyte monitoring devices are provided that include a housing; a processor coupled to the housing; and memory communicably coupled to the processor. An in vivo analyte sensor is communicably coupled to the processor, and a temperature sensor is communicably coupled to the processor. The memory includes instructions stored therein that, when executed by the processor, cause the processor to receive a sensor signal from the in vivo analyte sensor; detecting a temperature measurement from the temperature sensor; determine whether a threshold requirement is exceeded based on the temperature measurement; and determine a temperature-compensated analyte sensor signal. When the threshold requirement is not exceeded, the temperature-compensated analyte sensor signal is determined using the temperature measurement. Only when the threshold requirement is exceeded, the temperature-compensated analyte sensor signal is determined using an ambient-compensated temperature that is derived by compensating the temperature measurement for ambient temperature.

In some aspects of the present disclosure, methods of compensating for ambient temperature using a single temperature sensor are provided that include detecting a temperature measurement from a temperature sensor; and determining, with a processor, an ambient-compensated temperature from the temperature measurement using an offset term.

In some aspects of the present disclosure, analyte monitoring devices are provided that include a housing; a processor coupled to the housing; and memory communicably coupled to the processor. An in vivo analyte sensor is communicably coupled to the processor, and a temperature sensor is communicably coupled to the processor. The memory includes instructions stored therein that, when executed by the processor, cause the processor to detect a temperature measurement from the temperature sensor; and determine an ambient-compensated temperature from the temperature measurement using an offset term.

In some aspects of the present disclosure, methods of compensating for ambient temperature using temperature sensors are provided that include sampling at a first sampling rate, with a processor, first temperature measurements from a first temperature sensor on an on-body sensor; determining, with a processor, first ambient-compensated temperatures from the first temperature measurements; and determining, with a processor, final ambient-compensated temperatures by applying a correction gain or factor to the first ambient-compensated temperatures. The correction gain or factor changes value at a slower rate than the sampling rate.

In some aspects of the present disclosure analyte monitoring device are provided that include a housing; a processor coupled to the housing; and memory communicably coupled to the processor. An in vivo analyte sensor is communicably coupled to the processor, and a first temperature sensor and second temperature sensor are communicably coupled to the processor. The memory includes instructions stored therein that, when executed by the processor, cause the processor to sample at a first sampling rate, with a processor, first temperatures measured from a first temperature sensor on the housing; determine first ambient-compensated temperatures from the first temperature measurements; and determine final ambient-compensated temperatures by applying a correction gain or factor to the first ambient-compensated temperatures. The correction gain or factor changes value at a slower rate than the sampling rate.

In some aspects of the present disclosure, in vivo analyte sensors are provided that include a substrate layer; an electrode layer disposed on the substrate layer, and a temperature sensing element disposed on the substrate layer. The electrode layer includes a sensing area, and the temperature sensing element providing a signal for determining temperature adjacent the sensing area.

In some aspects of the present disclosure, analyte monitoring devices are provided that include a housing; electronic circuitry coupled to the housing, the electronic circuitry including a processor; and an in vivo analyte sensor electrically coupled to the electronic circuitry and extending from the housing. The in vivo analyte sensor include a substrate layer; an electrode layer disposed on the substrate layer; and a temperature sensing element disposed on the substrate layer, the temperature sensing element providing a signal for determining temperature adjacent a sensing area.

In some aspects of the present disclosure, analyte sensor devices are provided that include a body including an elongated member having a central tunnel that inserts into skin of a subject, electrodes disposed on the body, and a temperature sensor coupled to the body. The body is adapted to couple to the skin of the subject In some aspects of the present disclosure, methods are provided that include coupling an analyte sensor device to a skin of a subject and inserting a temperature sensor within the skin of the subject. The temperature sensor is disposed within the central tunnel. The sensor coupling device includes a body including an elongated member having a central tunnel that inserts into the skin of a subject, and electrodes disposed on the body. The body is adapted to couple to the skin of the subject.

In some aspects of the present disclosure, methods are provided that include receiving a first sensor signal from a first electrode on an in vivo analyte sensor on an on-body sensor; receiving a second sensor signal from a second electrode on the in vivo analyte sensor, and determining, with a processor, a compensated temperature at the two working electrodes based on the difference between the temperature dependencies for the different sensing chemistries on the two working electrodes. The first electrode and second electrode include different sensing chemistries with different temperature dependencies.

In some aspects of the present disclosure, analyte monitoring devices are provided that include a housing; a processor coupled to the housing; and memory communicably coupled to the processor. An in vivo analyte sensor is communicably coupled to the processor, and the in vivo analyte sensor includes two working electrodes. The memory includes instructions stored therein that, when executed by the processor, cause the processor to detect a first sensor signal from a first electrode on the in vivo analyte sensor; detect a second sensor signal from a second electrode on the in vivo analyte sensor; and determine a compensated temperature at the two working electrodes based on the difference between the temperature dependencies for the different sensing chemistries on the two working electrodes. The first electrode and second electrode include different sensing chemistries with different temperature dependencies.

BRIEF DESCRIPTION OF DRAWINGS

FIG. 10 illustrates an electrode arrangement for a typical three-terminal sensor, according to certain embodiments;

FIG. 11 illustrates an electrode arrangement for a three-terminal analyte sensor wherein one of the electrodes is also an embedded RTD, according to certain embodiments;

FIG. 13 illustrates a front-side view of an analyte sensor having thermocouple temperature sensor, according to certain embodiments;

FIG. 14 illustrates a back-side view of an analyte sensor having thermocouple temperature sensor, according to certain embodiments;

DETAILED DESCRIPTION

Figure 1:
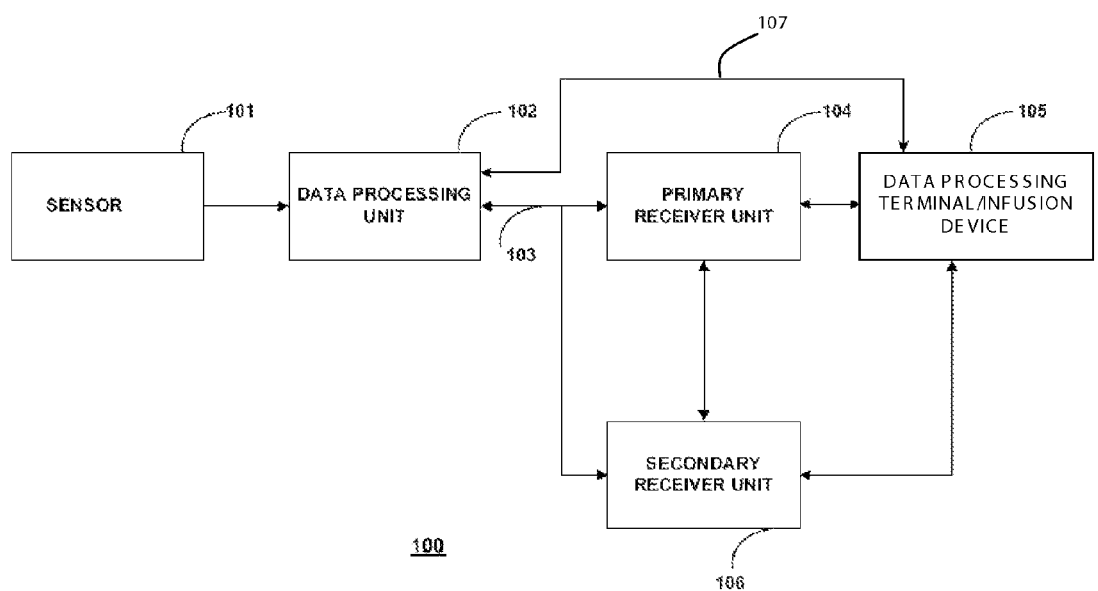
FIG. 1 shows a block diagram of an embodiment of an analyte monitoring system, according to certain embodiments.

Before the present disclosure is described in additional detail, it is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges is also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described. All publications mentioned herein are incorporated herein by reference to disclose and describe the methods and/or materials in connection with which the publications are cited.

It must be noted that as used herein and in the appended claims, the singular forms "a", "an", and "the" include plural referents unless the context clearly dictates otherwise.

The publications discussed herein are provided solely for their disclosure prior to the filing date of the present application. Nothing herein is to be construed as an admission that the present disclosure is not entitled to antedate such publication by virtue of prior disclosure. Further, the dates of publication provided may be different from the actual publication dates which may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure.

The figures shown herein are not necessarily drawn to scale, with some components and features being exaggerated for clarity.

The analyte sensor may be configured so that at least a portion thereof is placed under the skin of the patient to detect the analyte levels of the patient, and another portion of the analyte sensor—which may be above the skin—is coupled to electronics within a housing that is positioned externally on the skin of the subject. The electronics may include various components, such as communication element(s) for communication with a remote receiving unit. The analyte monitoring device that is coupled to the subject's body and includes the in vivo positioned analyte sensor, housing, and electronics (e.g., data processing, storage, and/or communication components) is also referred to herein as an "on-body unit", "OBU", "on-body sensor", "on body patch", or "patch".

Analyte sensors may have temperature dependencies and the sensor signals produced by the sensors may then be affected by temperature changes. An error caused by temperature may lead to an associated error in analyte measurements, such as glucose measurements.

It should be appreciated the subject matter of the disclosure is not limited to transcutaneous analyte sensor, but is also applicable to in vivo analyte sensors in general.

Temperature Compensation

As summarized above, aspects of the present disclosure relate to analyte monitoring systems, devices, and methods thereof related to temperature compensation. It should be appreciated that while the devices and methods may be described in terms of a subcutaneous sensor, other in vivo analyte sensors may also be applicable and the subject matter not limited to specifically subcutaneous analyte sensors.

It should also be appreciated that the embodiments described herein are exemplary and should not be viewed as limiting. For example, it should be appreciated that the methods described herein may be implemented in an on-body unit, the receiver, or mixed between the on-body unit and the receiver. Thus, various combinations of the steps performed on the on-body unit or receiver are contemplated. For example, an on-body unit may perform some steps such as temperature measurement and transmit the measurement to a receiver, where a processor on the receiver performs subsequent processing, such as determining ambient temperature compensation, determining temperature-compensated analyte sensor signals, determining analyte levels, etc. Or, as another example, the on-body unit may perform the steps of measuring the temperature, determining ambient temperature compensation, and determining temperature-compensated analyte sensor signals. For instance, the on-body unit may transmit the results to a receiver wherein the results are provided on a user interface.

It is noted that the combinations of steps between the on-body unit and receiver are appreciated for the one temperature sensor and two temperature sensor embodiments. Thus, for example, steps in the two temperature sensor embodiments may also be performed on the on-body unit or the receiver in other embodiments—e.g., sampling of temperature sensors, and/or correction factor or gain determination, determining ambient temperature compensation, determining temperature-compensated analyte sensor signals, etc.

It is also appreciated that temperatures may be measured by a processor on the on-body unit and/or receiver. For example, a processor may receive temperature data from a temperature sensor and calculate a temperature from the temperature data. The temperature may be, for example, an analog or digital signal derived by the temperature sensor. For example, in certain embodiments, a processor on the on-body unit may be coupled to the temperature sensor and provide a temperature measurement to the receiver, wherein the receiver detects the temperature measurement communicated and then performs additional processing steps based on the temperature measurement. It is appreciated that in another embodiment, the temperature data from the temperature sensor is sent to the receiver and the processor on the receiver calculates the temperature from the temperature data. The processor may then use this detected temperature for additional processing steps.

Compensating Sensor Signals

Temperature measurements are important for obtaining accurate analyte measurements (e.g., glucose measurements) with on-body sensors that are part of in vivo analyte monitoring systems—e.g., continuous glucose monitor (CGM) systems or intermittent or periodic glucose monitoring systems. The analyte-sensing chemistry on a subcutaneously positionable analyte sensor, or other in vivo analyte sensor, of the on-body sensor is temperature dependent and the sensor signal produced by the in vivo analyte sensor is thus affected by temperature.

Subcutaneously inserted glucose sensors, for example, may measure glucose by correlating the sensor signal output with glucose concentration. The signal response of analyte sensor may be linear across the operating range of glucose concentrations. However, the slope of this response may vary as temperature around the analyte sensor tip changes.

In order to compensate for this thermal effect, knowledge of temperature around the sensor sensing area is needed. The term "sensing area" is used herein to mean the area of the analyte sensor where the sensing chemistries are located. For example, in certain embodiments, the sensing area is disposed at the sensor tip, and thus the temperature at the sensor tip is estimated.

Therefore, the effect of temperature may be taken into account in order to calculate an accurate value for glucose concentration.

On-body sensors may utilize a temperature sensor disposed near the in vivo analyte sensor to estimate the sensor temperature. This temperature measurement is used to compensate the analyte sensor signal for temperature effects. For example, temperature-compensated analyte sensor signal may be determined by:

$$I_{TC} = I * 1.07^{(32.5-T)},$$

where I is the raw sensor current, T is the measured temperature in degrees Celsius (C), and $I_{TC}$ is the temperature compensated signal that is proportional to glucose concentration.

Ambient temperature impinging on the on-body housing may influence temperature measurements, and in effect, create a temperature measurement error that will lead to a glucose calculation error. For example, in some instances, experiments have shown that in an ambient temperature environment of 20 degrees C., the resulting glucose error due to ambient temperature effects can be about 10%.

In some aspects of the present disclosure, on-body sensors employ a second temperature sensor used to compensate for errors in the sensor temperature measurement due to the influence of ambient temperature on the first temperature sensor. For example, one temperature sensor (T1) may be located close to the skin surface Tskin, and another temperatures sensor (T2) located close to the transmitter (TX) processor or on the printed circuit board (PCB).

The temperature which compensates for ambient temperature influence using two temperature sensors is determined by, for example:

$$T = T1 + K*(T1-T2)$$

where K is related to the thermal resistances between the first temperature sensor and the second temperature sensor, and is a constant (e.g., 0.5, 0.2, or other constant) that may be derived empirically; T1 is the measured temperature at the temperature sensor near the sensor; T2 is the measured ambient temperature from the second temperature sensor; and T is the temperature which is compensated for ambient temperature influence. Other more complex models may be contemplated; for instance, K may not be constant but rather a function of T1 and/or T2, for instance.

Ambient Temperature Compensation Using a Single Temperature Sensor

To estimate the temperature at the sensing area of the in vivo analyte sensor, ambient compensation may be performed. In some aspects of the present disclosure, ambient temperature compensation is provided using a single temperature sensor on the on-body sensor. Thus, a second temperature is not required to compensate for ambient effects. Having a single temperature instead of multiple temperature sensors may provide one or more benefits, such as a reduction in cost, a reduction in complexity, etc.

Figures 5, 6:
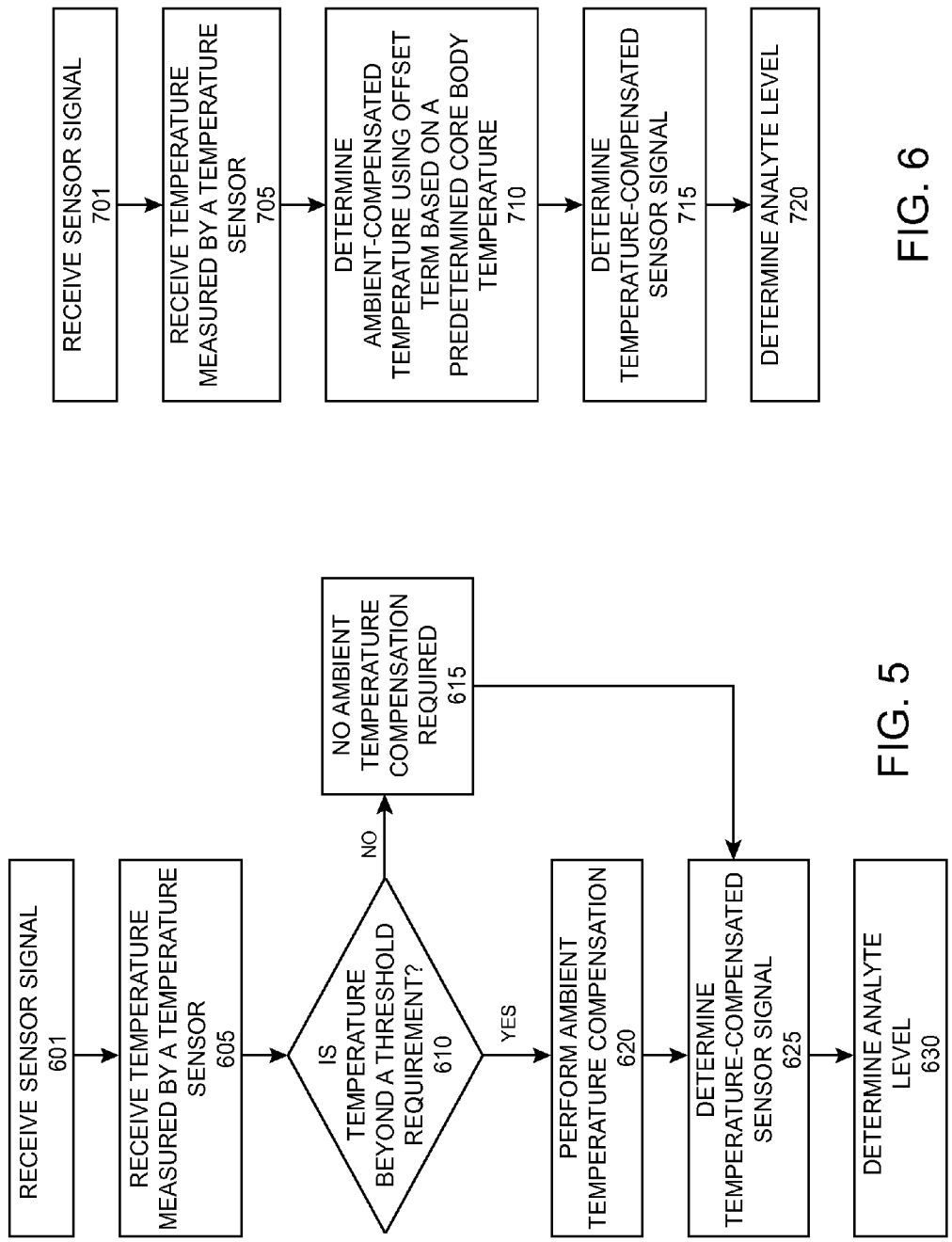
FIG. 5 illustrates a flowchart for a method of determining an analyte level by compensating for ambient temperature using a single temperature sensor on an on-body sensor, according to certain embodiments.
FIG. 6 illustrates a flowchart for a method of compensating for ambient temperature using a single temperature sensor on an on-body sensor, according to certain embodiments.

FIG. 5 illustrates a flowchart for a method of determining an analyte level by compensating for ambient temperature using a single temperature sensor (e.g., a temperatures sensor that approximates skin temperature) on an on-body sensor, according to certain embodiments.

At block 601, a sensor signal is received from an in vivo analyte sensor that is transcutaneously positioned with the skin of a subject. For example, the on-body sensor may include a processor that is electrically coupled to the analyte sensor and receives the sensor signal.

At block 605, the processor receives a temperature signal from a temperature sensor coupled to the on-body sensor. The temperature sensor may be, for example, positioned at or near a skin contacting surface to represent skin temperature. Since skin temperature may be affected by ambient temperature, a change in skin temperature may be correlated to a change in ambient temperature. When the ambient temperature is low, skin temperature will decrease, and when the ambient temperature is high, skin temperature will increase. Thus, deviations from "normal" skin temperature may be used to represent how strong the ambient temperature effects are.

At block 610, the processor determines if the measured temperature has reached a predetermined threshold value. For instance, a normal temperature or normal temperature range may be established and any deviation past the established threshold or thresholds (e.g., outside the normal temperature range) will trigger the ambient temperature correction. It should be appreciated that the term "predetermined threshold" is used broadly herein, and may include an upper and lower threshold. For example, an upper threshold and lower threshold may be implemented in some instances to establish a range. In some instances, only an upper or lower threshold may be implemented.

If the skin temperature does not deviate beyond the threshold, then it can be assumed that the ambient temperature effects are minimal, and no ambient temperature compensation is required, as represented by block 615. The temperature measurement may then be used to determine the temperature compensated analyte sensor signal, $I_{TC}$, as represented by block 625, and transmitted or displayed as a corresponding analyte (e.g., glucose) level, as represented by block 630.

If the skin temperature deviates beyond the predetermined threshold, then it can be assumed that the ambient temperature effects are significant, and ambient temperature compensation is performed (e.g., a correction factor applied) to compensate for the effects of ambient temperature, as represented by block 620. The resulting ambient-compensated temperature is then used to determine the temperature-compensated analyte sensor signal, $I_{TC}$, as represented by block 625, for a more accurate analyte (e.g., glucose) level determination that is transmitted or displayed, as represented by block 630.

For example, skin temperature for most people may normally range between 30 and 35° C. in ambient temperature environments that people are comfortable in. In certain embodiments, ambient temperature compensation is applied when "extreme" skin temperatures are detected (e.g., when the skin temperatures deviate beyond the predetermined threshold or thresholds). For instance, when the skin temperature measurement from the temperature sensor drops below 30 degrees C., then a correction factor can be added to the temperature measurement.

It should be appreciated that the predetermined threshold or thresholds (e.g., the "normal" range) may vary, and further, that the actual compensation algorithm (e.g., correction factor) implemented may also vary. As an example, ambient temperature compensation may be provided by the correction factor:

If $T<30$, then $T_{corrected}=T+1$

AND

IF $T>35$, then $T_{corrected}=T-1$

As another example, the ambient temperature compensation may be provided by a slightly more complex correction factor, such as:

If $T<30$, then $T_{corrected}=T+(30-T)/5$

AND

If $T>35$, then $T_{corrected}=T-(T-35)/5$ $T_{corrected}$ is then used to determine the temperature-compensated analyte sensor signal. In this way, the temperature-compensated analyte sensor signal accounts for ambient temperature influence. It should be appreciated that correction factors of varying complexities may be implemented in other embodiments.

It should be appreciated that illness may also affect the skin temperature of a subject—e.g., to make the skin temperature elevate outside the normal range. In certain embodiments, the ambient temperature compensation is applied only if the temperature error causes a high reading. In this way, only low temperature measurements are compensated.

In certain embodiments, changes in skin temperature are used to detect and correct for ambient temperature influences. For example, an ambient correction factor may be applied after a change in skin temperature is detected. It should be appreciated that the magnitude of the change may vary in different implementations as desired. For example, in some instances, a "normal" temperature could be detected at the start of a sensor wear, and when the temperature deviates by some predetermined amount (or, for example, by an amount detected by monitoring the changes during a period at the start of a sensor wear), then the ambient temperature compensation can be performed, such as described above.

In certain embodiments, temperature changes above a certain absolute value over a predetermined period of time initiates the ambient temperature compensation. For instance, $T(t=0)-T(t=-10)>5$, then $T_{corrected}=T+1$ $T(t=0)-T(t=-10)<-5$, then $T_{corrected}=T-1$ In certain embodiments, the ambient temperature compensation is based on the rate of change of skin temperature. In other embodiments, a combination of absolute temperature checks and temperature rate of change could be used in both the detection and correction.

It should be appreciated that the embodiment shown in FIG. 5 is exemplary, and that one or more steps may be performed by a processor on the on-body unit and/or a receiver in communication with the on-body unit in other embodiments. For example, in certain embodiments, the temperature sensor is coupled to the on-body unit and a processor on the on-body unit is detecting the temperature measurement, determining whether the threshold requirement is met, performing the ambient temperature compensation, and determining the temperature-compensated signal. Then, for example, the temperature-compensated signal is sent to a receiver wherein the temperature-compensated analyte level is displayed on a user-interface of the receiver for instance. In another embodiment, for example, the temperature sensor is coupled to the on-body unit and a processor on the on-body unit transmits the temperature measurements to the receiver where a processor coupled to the receiver determines whether the threshold requirement is met, performs the ambient temperature compensation, and determines the temperature-compensated signal. Then, for example, the temperature-compensated analyte level is displayed on a user-interface of the receiver for instance. It should be appreciated that the steps may be split up in other combinations between the on-body unit and the receiver.

It should be appreciated that, in certain embodiments, the ambient temperature compensation may, for the most, always or continuously be performed on the received analyte sensor signal. For example, the processor may continuously perform the ambient temperature compensation on the analyte sensor signal in addition to determining if the threshold temperature has been exceeded. When the temperature measurement does not exceed the temperature threshold, the temperature-compensated analyte sensor signal is based off the uncompensated signal, resulting in uncompensated analyte levels. When the temperature measurement exceeds the temperature threshold, the temperature-compensated analyte sensor signal is based off the ambient-compensated signal, resulting in ambient-compensated analyte levels. Thus, the temperature-compensated analyte sensor signal results in a mixed signal of the uncompensated analyte levels and ambient-compensated analyte levels. The temperature-compensated analyte sensor signal may be transmitted (e.g., communicated to a receiver) or presented on a user interface (e.g., displayed on a display for the user).

In other embodiments, the ambient-temperature compensation is not always or continuously performed on the received analyte sensor signal, but rather, only when the temperature threshold is exceeded. When the temperature measurement does not exceed the temperature threshold, the temperature-compensated analyte sensor signal is based off the uncompensated signal, resulting in uncompensated analyte levels presented on a user interface (e.g., displayed on a display). When the temperature measurement exceeds the temperature threshold, ambient-compensation is performed and the temperature-compensated analyte sensor signal is based off the ambient-compensated signal, resulting in ambient-compensated analyte levels presented on the user interface. Again, the temperature-compensated analyte sensor signal results in a mixed signal of the uncompensated analyte levels and ambient-compensated analyte levels.

It is also appreciated that in certain embodiments, the ambient compensation may be based off predetermined temperature ranges rather than predetermined thresholds. For example, the uncompensated analyte sensor signal may be used when the temperature measurement falls within a predetermined range or ranges, and the ambient compensated signal is used when the temperature measurement falls within another predetermined range or ranges.

It should be appreciated that in certain embodiments the temperature compensation may be applied to an analyte sensor signal that is not yet calibrated or converted (e.g., scaled by a scaling factor) to a corresponding analyte level, and thereafter converted to the corresponding analyte level. In yet other embodiments, the temperature compensation is applied to an analyte sensor signal that already represents the analyte level (e.g., is already calibrated or converted to the corresponding analyte level), and the temperature-compensated analyte sensor signal is the temperature compensated analyte level.

Ambient Temperature Compensation Based on Core Body Temperature

As previously noted, some on-body units may include a correction algorithm that utilizes two temperatures sensors to compensate for ambient temperature influence on the temperature sensor. For example, one temperature sensor is located close to the skin in a can that protrudes from the bottom of the transmitter. The other temperature sensor is located on the printed circuit board (PCB) in the transmitter and is a feature provided by the controller chip. Again, the correction method employed is:

$$T = T1 + K^*(T1-T2)$$

This method can be considered an "extrapolation" method, since two temperature measurements are made at points where the temperature for each is lower than the sensing area temperature, and the sensing area temperature is estimated by extrapolating from these two measured temperatures. In this transmitter configuration, the two temperature sensors are generally well separated, which results in a stable K value that is robust over different transmitter locations on the body and for different body types. As transmitter designs become more physically smaller, however, it becomes more difficult to separate the two temperature sensors thermally. Without adequate thermal separation, the K value becomes significantly less stable, and furthermore, becomes significantly larger, with the effect of amplifying the noise in the temperature measurement.

Utilizing a single temperature sensor instead of two may provide many advantages, such as cost savings. In some aspects of the present disclosure, ambient temperature compensation is based on a predetermined core body temperature and temperature measurements from a single temperature sensor.

FIG. 6 illustrates a flowchart for a method of compensating for ambient temperature using a single temperature sensor on an on-body unit, according to certain embodiments.

At block 701, a sensor signal is received from an analyte sensor that is transcutaneously positioned within the skin of a subject, or otherwise implanted in vivo. For example, the on-body unit may include a processor that is electrically coupled to the analyte sensor and receives the analyte sensor signal.

At block 705, the processor receives temperature data from a temperature sensor coupled to the on-body unit. For example, in certain embodiments, the temperature sensor may be positioned at or near a skin contacting surface to represent skin temperature.

At block 710, the processor determines an ambient-compensated temperature from the measured temperature using an offset term (e.g., an offset term based on a predetermined core body temperature). For example, a correction factor is applied to the measured temperature to correct for ambient temperature effects. The correction factor may have an offset term that is based on a predetermined core body temperature value—e.g., 37° C. since a user's core body temperature is relatively stable at approximately 37° C. For example, ambient temperature compensation may be provided by the following correction factor:

$$T_{est} = B_{corebody} + K^*T1$$

where $B_{corebody}$ is a predetermined core body temperature (e.g., approximately 37 degrees C.); K is a constant that may be empirically derived; and T1 is the measured temperature by the temperature sensor; and $T_{est}$ is the estimated sensing area temperature that is compensated for ambient temperature influence.

The resulting sensing area (e.g., sensor tip) temperature estimate is compensated for ambient effects and may then be used to determine the temperature-compensated analyte sensor signal, $I_{TC}$, as represented by block 715, for a more accurate glucose level determination that is transmitted or displayed, as represented by block 720.

The sensing area temperature estimate is an "interpolation" method since the sensing area temperature estimate is in between the core body temperature and the temperature measured at the transmitter. Measurement noise is not amplified using the interpolation method.

As similarly stated above, it should be appreciated that the embodiment shown in FIG. 6 is exemplary, and that one or more steps may be performed by a processor on the on-body unit and/or a receiver in communication with the on-body unit in other embodiments. For example, in certain embodiments, the temperature sensor is coupled to the on-body unit and a processor on the on-body unit detects the temperature measurement, determines an ambient-compensated temperature from the measured temperature using an offset term, and determines the temperature-compensated signal. Then, for example, the temperature-compensated signal is sent to a receiver wherein the temperature-compensated analyte level is displayed on a user-interface of the receiver for instance. In another embodiment, for example, the temperature sensor is coupled to the on-body unit and a processor on the on-body unit transmits the temperature measurements to the receiver where a processor coupled to the receiver determines an ambient-compensated temperature from the measured temperature using an offset term, and determines the temperature-compensated signal. Then, for example, the temperature-compensated analyte level is displayed on a user-interface of the receiver for instance. It should be appreciated that the steps may be split up in other combinations between the on-body unit and the receiver.

Using One-Temperature Sensor Models and Two-Temperature Sensor Models

Subcutaneously inserted glucose sensors measure glucose by correlating the sensor signal output with glucose concentration. As stated above, this signal output is affected by temperature. As stated above, in some instances, temperature is estimated using two temperature sensors.

For example, in certain embodiments, one thermistor is disposed close to the skin surface to provide a skin temperature measurement, $T_{skin}$. Another thermistor is disposed away from the skin surface to provide a temperature measurement, $T_{cpu}$, that may be near the on-body processor that is has more influence from the ambient temperature and less influence from the sensor tip temperature than $T_{skin}$.

Figure 7:
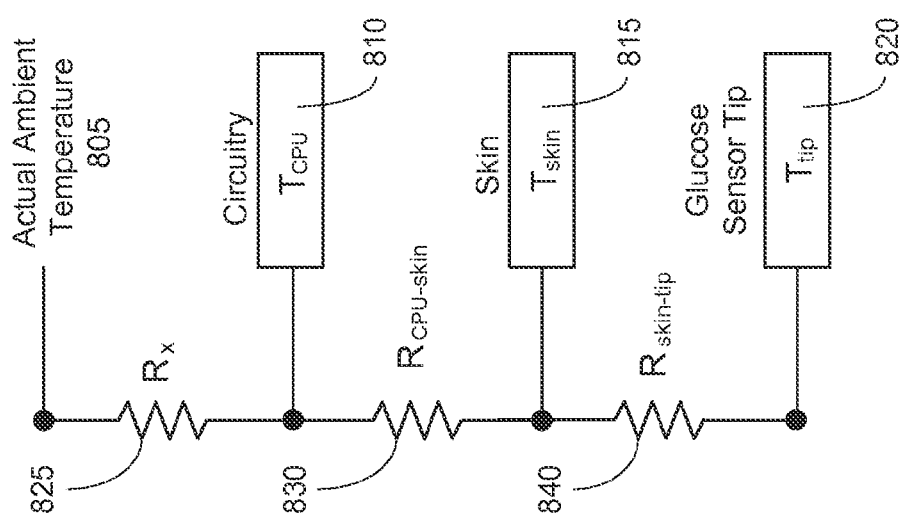
FIG. 7 illustrates a circuit diagram representation of an example two-thermistor model, according to certain embodiments.

FIG. 7 illustrates a circuit diagram representation of an example two-thermistor model, according to certain embodiments. It should be appreciated that in other embodiments a different type of temperature sensor may be implemented.

As shown, temperature 805 is ambient air temperature; temperature $T_{cpu}$ 810 is the temperature at the circuitry (e.g., processor); temperature $T_{skin}$ 815 is the temperature at the skin surface; and temperature $T_{tip}$ 820 is estimated temperature at the sensing area (e.g., at the sensor tip). Resistance $R_x$ 825 represents thermal resistance between the ambient air and circuitry; $R_{cpu-skin}$ 830 represents thermal resistance between the circuitry and the skin; and $R_{skin-tip}$ 835 represents thermal resistance between the skin and sensing area.

$K=R_{skin-tip}/R_{cpu-skin}$ is a fixed constant, which acts as a scaling factor to extrapolate the difference $T_{tip}-T_{skin}$ as a function of the difference $T_{skin}-T_{cpu}$.

$$T_{tip}=T_{skin}=K*(T_{skin}-T_{cpu})$$

This relationship is used to calculate the temperature at the sensing area, $T_{tip}$:

$$T_{tip}=T_{skin}+K*(T_{skin}-T_{cpu})$$

In some aspects, the two-thermistor model has relative insensitivity to changes in ambient temperature, core body temperature, and site-to-site thermal impedance variability. The two-sensor model may also possess minute-to-minute variability in the temperature sensor (e.g., thermistor) readings $T_{cpu}$ and $T_{skin}$ that can degrade the smoothness of the temperature corrected glucose signal. This is especially a concern when plasma-to-interstitial glucose lag compensation is required.

In certain embodiments, the one-sensor model described above assumes that the core body temperature is the dominant heat source, and that the thermal resistance between the core body and the sensing element is universally constant.

Figure 8:
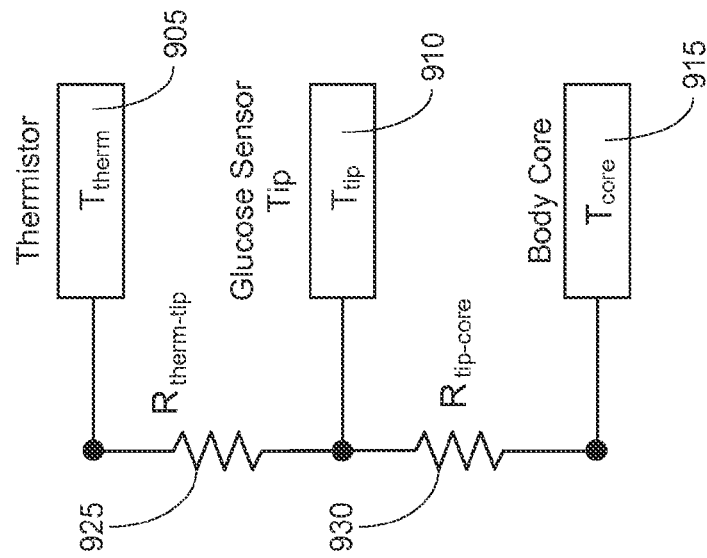
FIG. 8 illustrates a circuit diagram representation of an example one-thermistor model, according to certain embodiments.

FIG. 8 illustrates a circuit diagram representation of an example one-thermistor model, according to certain embodiments. As shown, temperature $T_{therm}$ 905 is the temperature at the thermistor; sensing area temperature (e.g., sensor tip temperature) $T_{tip}$ 910 is the estimated temperature at the sensing area, and body core temperature $T_{core}$ 915 is the predetermined body core temperature. $R_{therm-tip}$ 925 represents thermal resistance between the thermistor and the sensing area. $R_{tip-core}$ 930 represents thermal resistance between the sensing area and the core body.

Where $K_{1TM}=R_{tip-core}/R_{therm-tip}$, such that $T_{tip}$ can be calculated as follows:

$$T_{tip}=(T_{therm}*K_{1TM}+T_{core})/(1+K_{1TM})$$

where $K_{1TM}$ is an empirically derived constant for the one-thermistor model.

Since the model does not extrapolate between two measurement channels, improved minute-to-minute smoothness occurs. Experimental data suggests that while the one-thermistor model has a very consistent minute-to-minute estimate, the site-to-site variability results in a poorer overall $T_{tip}$ estimate compared to the two-thermistor model. $R_{tip-core}$ in the one-thermistor model assumes knowledge of a constant thermal resistance between the body's core temperature and the sensing area (e.g., sensor tip). The value of this resistance might vary between the arm and abdomen sites because of different proximities to the body core.

The minute-to-minute variability that is caused by the extrapolation operation of the two-thermistor model measurements directly affects the minute-to-minute variability of the glucose measurement. In addition, it limits the extent of plasma-to-interstitial glucose lag correction possible.

In some aspects of the present disclosure, a correction gain is determined based on temperature estimates calculated using the one-thermistor model and the two-thermistor model. For instance, two thermistors are disposed on the on-body sensor, such as described above for the two-thermistor model. Temperature estimates are calculated using the one-therm thermistor model technique, resulting in sensor temperature estimate $T_{1TM}$. Temperature estimates are also calculated using the two-thermistor model, resulting in sensor temperature estimate $T_{2TM}$.

In certain embodiments, present to recent past comparisons of the two temperature estimates $T_{1TM}$ and $T_{2TM}$ are used to improve the accuracy of the sensor temperature measured $T_{1TM}$ and utilize this recursively modified estimate of the sensor temperature. The result is a sensor temperature estimate that has the minute-to-minute smoothness (which is related to precision) of the one-thermistor model, yet has the site-to-site variability (which is related to accuracy) of the two-thermistor model. This approach allows for a smoother two-thermistor model temperature corrected raw glucose signal, which helps improve the signal quality of the final product, reduce the uncertainty of threshold and projected alarms due to unnecessary noise, reduce the uncertainty of rate arrows, reduce the impact of non-physiological temperature transients, and allow for better concordance to reference blood glucose.

Figure 9:
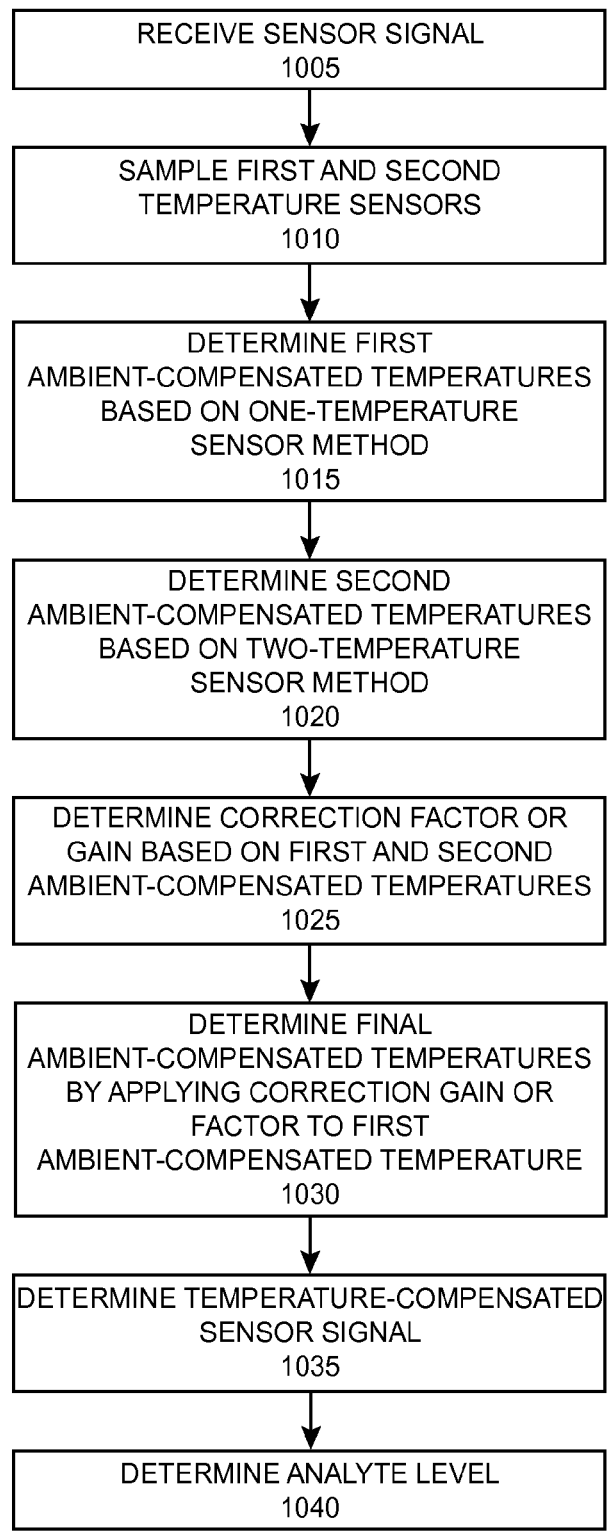
FIG. 9 illustrates method of compensating for ambient temperature using temperature sensors on an on-body sensor, according to certain embodiments.

FIG. 9 illustrates method of compensating for ambient temperature using temperature sensors on an on-body unit, according to certain embodiments.

At block 1005, a sensor signal is received from an analyte sensor that is transcutaneously positioned within the skin of a subject, or otherwise implanted in vivo. For example, the on-body unit may include two temperature sensors (e.g., two thermistors) and a processor that is electrically coupled to the analyte sensor and receives the sensor signal.

At block 1010, first and second thermistors on the on-body unit are sampled by the processor. At block 1015, the processor determines ambient-compensated temperatures based on a one temperature model. At block 1020, the processor determines ambient-compensated temperatures based on a two temperature model.

At block 1025, correction gain or factor is determined based on past sampled ambient-compensated temperatures for the one-thermistor and two-thermistor models. At block 1030, a final ambient-compensated temperature is determined by applying the correction gain or factor to the ambient-compensated temperatures determined in block 1015.

For example, in certain embodiment, a simple gain error model is assumed on the one thermistor model. In other words:

$$T_{1TM}(k)=K_{1TM}(k)\times T_{1TMnominal}(k)$$

where $T_{1TMnominal}$ is the nominal output based on the one-thermistor model as previously described, $K_{1TM}$ is the correction gain for this model, and $T_{1TM}$ is the final ambient-compensated temperature resulting from using the improved one-thermistor model.

"k" refers to the index of the sample instance/time. Note that the value $T_{1TMnominal}$ is computed during every sample instance and attempts to reflect the latest temperature, which may or may not be rapidly varying over time. However, $K_{1TM}$ is computed such that the value changes very slowly overtime, with the assumption that the biological and environmental factors that affect this gain error changes very slowly over time. $K_{1TM}$ changes at a rate slower than the sampling rate. In certain embodiments, this is achieved by performing a moving average between the nominal one-thermistor model and two-thermistor model outputs:

$$K_{1TM}(k):=\frac{1}{N}\sum_{j=0}^{N-1}\frac{T_{2TM}(k-j)}{T_{1TMnominal}(k-j)}$$

where $T_{2TM}$ is the output of the two-thermistor model, and N is a relatively large positive window such that $K_{1TM}$ varies very slowly and reliably over time. The values of $T_{1TMnominal}$ and $T_{2TM}$ pairs are such that both values are valid and/or can be computed at any time index within the set of N most recent pairs.

In an alternative embodiment, the same assumptions are made as the previous embodiment, but the evolution of $K_{1TM}$ is governed by a calculation that is more robust to occasional $T_{1TM}$ nominal and $T_{2TM}$ outliers. As in the previous embodiment, the values of $T_{1TMnominal}$ and $T_{2TM}$ pairs must be such that both values are valid and/or can be computed at any time index within the set of N most recent pairs.

$$K_{1TM}(k) := \frac{\sum_{j=0}^{N-1} T_{2TM}(k-j)}{\sum_{j=0}^{N-1} T_{1TMnominal}(k-j)}$$

In yet another embodiment, parameter adaption is used. One example is to use the MIT adaption rule:

$$\frac{d}{dt} K_{1TM}(t) = -\gamma e(t) \frac{\partial e}{\partial K_{1TM}}$$

$$= \gamma \left[\frac{T_{2TM}(k)}{T_{1TMnominal}(k)}\right]^2 \left[\frac{1}{K_{1TM}(k)}\right]^3$$

Where $\gamma$ is an adaption scaling factor that governs the aggressiveness level of the adaptation, and needs to be tuned a priori. Taking a backwards difference approximation to discretize the above equation, the following difference equation that governs the time evolution of $K_{1TM}$ is obtained:

$$K_{1TM}(k) = K_{1TM}(k-1) + \frac{\gamma}{\delta}\left[\frac{T_{2TM}(k)}{T_{1TMnominal}(k)}\right]^2 \left[\frac{1}{K_{1TM}(k)}\right]$$

where $\delta$ is the sample time of the calculation. To avoid the need to solve for the root of a quadratic equation, a time delayed approximate can be used:

$$K_{1TM}(k) = K_{1TM}(k-1) + \frac{\gamma}{\delta}\left[\frac{T_{2TM}(k)}{T_{1TMnominal}(k)}\right]^2 \left[\frac{1}{K_{1TM}(k-1)}\right]$$

The three embodiments described above are based on the assumption that the main source of inaccuracy of the one-thermistor model is predominately a gain error. If an offset error is assumed, the same concepts described in the embodiments above can be implemented with a slight modification. For example, one would assume:

$$T_{1TM}(k) = D_{1TM}(k) + T_{1TMnominal}(k)$$

where the offset difference $D_{1TM}$ can be corrected by the following windowed comparison between the nominal one-thermistor model and two-thermistor model approaches.

$$D_{1TM}(k) := \sum_{j=0}^{N-1} T_{2TM}(k-j) - \sum_{j=0}^{N-1} T_{1TMnominal}(k-j)$$

The final ambient-compensated temperature may then be used, for example, to determine a temperature-compensated signal, as represented by block 1035. The corresponding analyte (e.g., glucose) level may then be transmitted or displayed, as represented by block 1040.

In addition, given that two thermistors are available, the above embodiments can be implemented on both thermistors such that instead of using a single modified one-thermistor model, an average of two modified one-thermsitor model outputs is used.

Again, as similarly stated above, it should be appreciated that the embodiment shown in FIG. 9 is exemplary, and that one or more steps may be performed by a processor on the on-body unit and/or a receiver in communication with the on-body unit in other embodiments. For example, in certain embodiments, the temperature sensors are coupled to the on-body unit and a processor on the on-body unit samples the temperatures sensors, determines the ambient-compensated temperature from the one-temperature sensor model and two-temperature sensor model, determines the correction factor or gain, determines the final ambient-compensated temperatures. The processor on the on-body unit may then either determine the temperature-compensated signal, or transmit the final ambient-compensated signal to a receiver having a processor that determines the temperature compensated signal and presents the corresponding analyte level on a user interface. It should be appreciated that these embodiments are exemplary, and that the steps may be split up in other combinations between the on-body unit and the receiver. For example, in other embodiments, one or more of the steps in determining the ambient-compensated signal and/or final ambient compensated signal may be performed by the receiver.

Provided below is an example analysis. It should be appreciated that the example analysis is exemplary and is not meant to be limiting.

Example Analysis:

Using the temperature sensor close to the skin, the equation for sensor (skin) temperature becomes:

$T=0.25*Tc+0.75*T1$ wherein Tc is the body core temperature 37 degrees C. and is treated as a constant.

Using the temperature sensor on the PCB, the equation for sensor (skin) temperature becomes:

$T=0.54*Tc+0.46*T2$

If the core temperature is 37 degrees C., these two equations will correct for the ambient effect. Further, the intrinsic measurement error in T1 or T2 is not amplified (like with the two temperature sensors implementation), but rather attenuated a bit.

Moreover, if the core body temperature does deviate from 37 degrees C., the resulting error is not significant, and further does not depend on the ambient temperature. For example, the following data was found:

For the temperature sensor close to the skin (T1): The resulting error, Terr, is 0.25 degrees C. per degree deviation from 37 degrees C.

| Tc | Terr | Glucose Error (assume F = 105 rather than 1.07) |
|----|------|-------------------------------------------------|
| 36 | 0.25 | −1.2% |
| 37 | 0 | 0% |
| 38 | −0.25 | 1.2% |
| 39 | −0.5 | 2.5% |
| 40 | −0.75 | 3.7% |

For the temperature on the PCB (T2), the resulting error is only modestly worse; Terr, is 0.5 degrees C. per degree deviation from 37 degrees C.

| Tc | Terr | Glucose Error (assume F = 105 rather than 1.07) |
|---|---|---|
| 36 | 0.54 | −2.6% |
| 37 | 0 | 0% |
| 38 | −0.54 | 2.6% |
| 39 | −1.08 | 5.4% |
| 40 | −1.62 | 8.2% |

Temperature Sensors Disposed Adjacent the Sensing Area

In some aspects of the present disclosure, an on-body sensor is provided with a temperature sensor disposed on the analyte sensor adjacent to the sensing area (e.g., at sensor tip on the sensor tail). In such case, extrapolation is not required to determine the temperature value at the sensing area. This may provide one or more benefits, such as less data required to be transmitted to the controller, promoting shorter RF packets and longer battery life, reducing complexity of system software, etc.

In some aspects of the present disclosure, embedded temperature sensors are provided. The term "embedded temperature sensor" is used herein to mean a temperature sensor that is disposed on an analyte sensor such that it is exposed to body fluids (e.g., interstitial fluids) when the analyte sensor is positioned in vivo.

An embedded temperature sensor enables the temperature of the interstitial fluid itself to be measured. In this way, the temperature at the location of the sensor chemistry of in vivo analyte sensors may be measured. Since the sensing chemistry is within interstitial fluid, a measurement of the interstitial fluid temperature provides a very accurate temperature measurement for the sensing area.

In certain aspects of the present disclosure, the embedded temperature sensors are resistive temperature detection (RTD) devices. RTDs are devices which increase in electrical resistance with increasing temperature. Temperature may be measured, for example, by driving a reference current through the device and measuring the voltage across the device. Platinum provides high accuracy, linearity, and stability when used as an RTD. It should be appreciated that other materials (e.g., metals or metal-alloys, etc.) may be used as an RTD.

As a non-limiting example, a platinum RTD may have a nominal resistance at 0 degrees C. and a temperature coefficient of 0.00385Ω/Ω/degrees C. The nominal 0 degrees C. resistance may range from 100Ω to 500Ω, for example, depending on construction. The absolute resistance of the RTD at any given temperature T determined as follows:

$$RTD(T) = RTD_0 + T \cdot 0.00385 \Omega/\Omega/\text{degrees C.}$$

where RTD(T) is equal to the absolute RTD resistance in Ohms; $RTD_0$ is equal to the resistance of the RTD at 0 degrees C. in Ohms; and T is equal to the temperature in degrees C. And further, the linearity of the platinum RTD may, for example, be less than +/−0.5% from 0-100 degrees C.

In certain embodiments, platinum is used as a sensor conductive base material to form an electrode that is also an embedded RTD. The platinum RTD trace may be made by any variety of manufacturing processes. For example, laser ablation may be used to create the electrodes and accommodate very fine feature sizes, as well as allow for a long platinum RTD trace to increase its resistance.

FIG. 10 illustrates an electrode arrangement for a typical three-terminal sensor, according to certain embodiments. The subcutaneous tail of a three-terminal analyte sensor is shown including a working electrode 1101, reference electrode 1102, and counter electrode 1103. Each of the three electrodes 1101, 1102, 1103 has a single electrical trace 1121, 1122, 1123, respectively, that extends from the along the sensor tail towards the electronics in the on-body sensor. The electrical traces provide the electrical communication path between the corresponding electrodes and electronics in the on-body sensor.

FIG. 11 illustrates an electrode arrangement for a three-terminal analyte sensor wherein one of the electrodes is also an embedded RTD, according to certain embodiments. The subcutaneous tail of the three-terminal analyte sensor is shown including a working electrode 1201 and reference electrode 1202, as well as a counter electrode 1203 that is also an embedded RTD. When the sensor is positioned in vivo into the skin of the subject, the embedded RTD and electrode 1203 is embedded in the subject and exposed to interstitial fluid.

The embedded RTD and electrode 1203 includes an electrical trace having two ends 1223a, 1223b such that current can be applied to the RTD and voltage measured across the two ends 1223a, 1223b. In the embodiment shown, the embedded RTD and electrode 1203 is a single electrical trace 1223 that extends back and forth longitudinally to increase the distance of the electrical trace. A long trace increases resistance and facilitates a better measurement. In certain embodiments, a long platinum RTD trace is used to increase its resistance and facilitate a better measurement.

Figure 12:
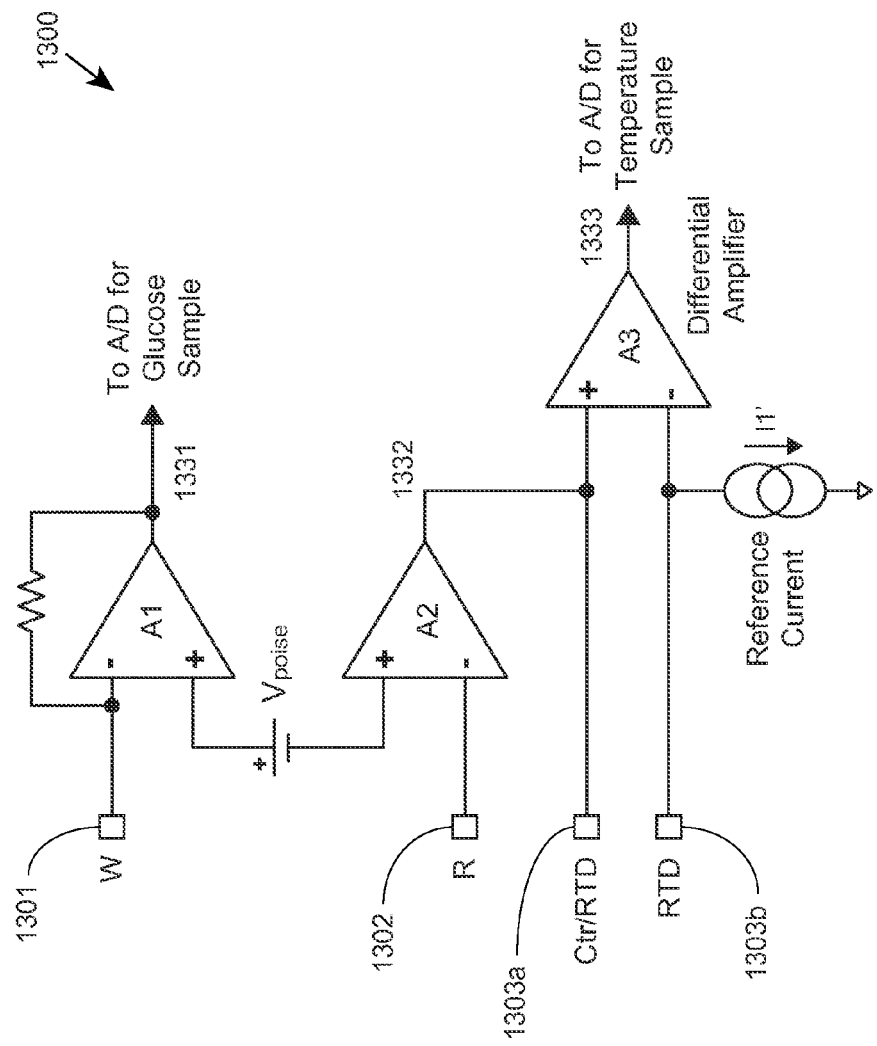
FIG. 12 illustrates a partial circuit diagram for an example analog front-end circuit for a three-terminal analyte sensor with one of the electrodes as an embedded RTD, according to certain embodiments.

FIG. 12 illustrates a partial circuit diagram for an example analog front-end circuit for a three-terminal analyte sensor with one of the electrodes as an embedded RTD, according to certain embodiments. As shown, analog front-end 1300 includes a working electrode contact point 1301 (e.g., to electrically couple to working electrode 1201 in FIG. 11) and a reference electrode contact point 1302 (e.g., to electrically couple to reference electrode 1202 in FIG. 11). Analog front-end 1300 also includes contact points 1303a, 1303b. Contact point 1303a electrically couples to the counter electrode of the analyte sensor and also serves as one end of the embedded RTD (e.g., end 1203a in FIG. 11). Contact point 1303b serves as a contact point that electrically couples to the other end of the embedded RTD (e.g., end 1203b in FIG. 11).

Analog front-end also includes amplifiers A1, A2 that are electrically coupled to the working and reference electrodes to provide the condition analyte signal 1331 for sampling by an A/D converter (not shown). Contact point 1303a is electrically coupled to the inverting input of amplifier A3. Contact point 1303b is electrically coupled to the non-inverting input of differential amplifier A3 along with the output 1332 of amplifier A2. Amplifier A3 measures the voltage across the RTD which is created by the flow of current provided through the RTD, as indicated by reference current, I1. The output 1333 of amplifier A3 provides the temperature signal to the A/D converter for the temperature sample.

It should be appreciated that other circuit elements may also be implemented to the analog front-end 1300—e.g., to improve performance, such as a reference resistor for the reference current to flow through, which could eliminate temperature and other errors in the A/D converter.

It should also be appreciated that in other embodiments, the embedded RTD could be implemented as one of the other electrodes—e.g., the reference electrode or working electrode. Furthermore, it should also be appreciated that an embedded RTD may be implemented in an analyte sensor with a different number of electrodes than three—e.g., a two-electrode sensor. For example, a two-electrode sensor may have a working electrode as well as a reference electrode that is also an embedded RTD.

It should be appreciated that the shape of the embedded RTD and electrode may vary in other embodiments. For example, in other embodiments, the embedded RTD and electrode may extend back and forth longitudinally a number of times that is different than shown in FIG. 11. Or alternatively, for example, the embedded RTD and electrode may extend back and forth latitudinally, or both latitudinally and longitudinally. It should be appreciated that in other embodiments, any variety of patterns and designs may be used for the shape of the embedded RTD and electrode, as long as the counter electrode has sufficient surface area exposed to the interstitial fluid. Moreover, the position of the two ends of the embedded RTD and electrode may also vary in different embodiments.

Temperature Sensors and Analyte Sensor Devices Having Elongated Members with Central Tunnels In some aspects of the present disclosure, analyte sensor devices are provided that include a body having an elongated member (e.g., a hollow tube) with a central tunnel therein. Electrodes are disposed on the outside of the body and a temperature sensor coupled to the body. In certain embodiments, the central tunnel houses a temperature sensor. In this way, the temperature sensor provides a direct temperature measurement at the analyte sensor tip.

For example, in certain embodiments, a needle is disposed within the central tunnel during insertion. In certain embodiments, the sharp is withdrawn and a temperature sensor is inserted into the central tunnel of the hollow tube. The inserted temperature sensor may then provide temperature measurements at the analyte sensor tip.

In certain embodiments, the temperature sensor is adapted to pierce the skin and serve as the needle. For example, the temperature sensor may be formed as the needle, formed as part of the sharp, or coupled to a needle. In some instances, the temperature sensor is adapted to pierce the skin of the subject and is softened by exposure to body fluids—e.g., made from or include a material that softens when exposed to body fluids. In this way, the sharp softens when inserted into the subject and does not become an irritant.

In certain embodiments, the on-body housing of the analyte sensor device is adapted to couple to an insulin delivery tube and insulin pump. For example, the analyte sensor device may serve as an insulin delivery cannula. In such case, the analyte sensor device functions as an analyte monitoring system and integrated insulin delivery cannula.

In certain embodiments two conductors, such as wires or conductive plastic, are extruded in the walls of the insulin delivery cannula. One of the wires acts as a reference electrode for the analyte (e.g., glucose) sensing function. For example, in some instances, the one wire may be made from silver or other suitable conductor with or without a coating, and the second wire made from either gold or other highly conducting material. Both wires are fully embedded into the walls of the cannula (e.g., a soft cannula) and would extend near the tip of the cannula. At or near the tip of the cannula, each of the two wires terminates at a feature that allows the wires to electrochemically communicate with tissue and body fluids in conjunction with appropriate chemical or biological materials. For instance, the silver wire could be plated or chemically chloridized with silver chloride to form an Ag/AgCl reference electrode or auxiliary electrode in a two electrode system. The other wire may be, for example, coated or deposited with glucose sensing chemistry to form a working electrode. In some instances, either or both electrodes may be covered by a thin layer of membrane to restrict the glucose flux as well as to protect the electrode components. Further, in some instances, a section of the cannula may be laser ablated or chemically etched to increase the surface area of the active working or reference electrode.

In certain embodiments, a thermocouple is extruded into the insulin delivery cannula. For example, the thermocouple may be co-extruded into an insulin delivery cannula such as described above. The thermocouple may be co-extruded with the other materials in order to provide temperature sensing at the location of interest at the implanted site—e.g., close to the sensing chemistry.

In certain embodiments, the dual function soft cannula may be attached to a housing and adhesive patch to facilitate retention on the skin. The housing may include the additional components needed for continuous glucose sensing—e.g., a thermistor or thermocouple for skin temperature measurement and a counter electrode to return electrons to the body to form a closed sensor circuit. The wires of these two components may be molded inside the plastic cannula housing, for example. These wires along with the two electrode wires may be exposed at the distal end of the cannula and arranged around a keyed fluid and electrical connecting point. The connection point allows all wires to be connected to their counterparts embedded inside a connector on a multi conducting insulin delivery tube, for instance, when the cannula is connected to the tube.

In certain embodiments, the wires for the thermistor or thermocouple for skin temperature measurements and a wire to act as a counter electrode is extruded or embedded into the cannula, creating a multi-function structure.

The wires embedded inside the wall of the insulin delivery tubing enable a dual function device that delivers insulin and provides continuous glucose monitoring support functionality such as sensor signal transduction, calibration and user interface. The integrated system described above may be attached to or worn on the body.

In certain embodiments, the integrated system may include an insulin delivery pump, the CGM system, the data collection and processing hardware, and the user interface including control buttons and display. In some instances, the system may also have a discrete glucose meter embedded in it so that the user can check the blood glucose with the system using test strips.

In certain embodiments, the hardware of the insulin delivery pump and the continuous glucose monitor are combined into a more compact assembly and attached to the body using an adhesive patch. Other components (data processing algorithms, user interface, and/or discrete glucose meter, etc.) may, for example, be integrated into a separate controller that communicates with the assembly wirelessly. This embodiment may significantly improve usability of the system.

Thermocouples

In some aspects of the present disclosure, ambient temperature compensation is provided using a thermocouple temperature sensor. The thermocouple temperature sensors are included of dissimilar metals—e.g., metal-inks. Example metals may include, but are not limited to, gold, silver, carbon, titanium, and alloys thereof.

The physical properties of the dissimilar metals create a thermocouple temperature sensor at the junction of the dissimilar metals. A small voltage that is dependent on temperature will exist between the dissimilar metals. The voltage produced by a thermocouple is known and predictable based on the properties of the two dissimilar metals. Measurement of this voltage results in data that can be used to accurately determine the temperature of the analyte sensor (e.g., glucose sensor). For example, measurement of this small signal can be performed by the electronics located in the on-body unit—e.g., in the transmitter of the on-body unit.

For example, in certain embodiments, calibration can be done by applying two different voltages to a measurement circuit and computing the zero point and scale of the measurement circuit. This method may in some instances, include one or more benefits—e.g., cost, accuracy, and speed. For example, thermocouple sensors can be manufactured very inexpensively and may be conducive to high volume processing.

In certain embodiments, the thermocouple is created by depositing two different metals onto the analyte sensor tail and joining them at a junction located close to the actual sensing area. For example, the metals may be deposited onto the analyte sensor substrate by any variety of methods, such as, but not limited to, sputtering, electroplating, or using a metallic ink. In some instances, the thermocouple may be constructed using metal wire.

The two traces of different metals are electrically conducted ("bonded") to form the junction. Having the junction adjacent to the actual sensor active area provides a temperature measurement close to the sensing area, resulting in an accurate measurement.

In certain embodiments, the thermocouple is formed on the same side of the analyte sensor as the sensing area (e.g., glucose sensing area). In other embodiments, the thermocouple is formed on the opposite side of the analyte sensor as the sensing area.

FIG. 13 illustrates a front-side view of an analyte sensor having thermocouple temperature sensor, according to certain embodiments. The analyte sensor 1400 shown is a glucose sensor having a glucose sensing area 1401 including three electrodes—e.g., working electrode, reference electrode, and counter electrode. Electrical traces 1402 extend from the electrodes in the sensing area 1401 to corresponding contact points 1402 for connection to the electronics in the on-body sensor.

Glucose sensor 1400 also includes two traces 1404, 1405. Trace 1404 and 1405 are made of dissimilar materials (e.g., different metals or metal-alloys) that extend from corresponding contact points 1407, 1408, respectively, to a junction point 1406 located next to the glucose sensing area 1401. Contact points 1407, 1408 provide electrical connection to the electronics on the on-body sensor for measurement of the voltage produced by the junction of dissimilar materials.

In the embodiment shown, the two traces 1404, 1405 of dissimilar materials are on the same side (e.g., front side) of the glucose sensor 1400, and further are on the same side of the sensor 1400 as the glucose sensing area 1401 and electrode traces 1402. While the distance between the junction point 1406 and the glucose sensing area 1401 may vary in different embodiments, having the junction point 1406 closer to the glucose sensing area 1401 provides a more accurate temperature estimate at the glucose sensing area 1401. Some space is needed to provide distance between the junction point 1406 and the glucose sensing area 1401 for insulation between the two.

FIG. 14 illustrates a back-side view of an analyte sensor having thermocouple temperature sensor, according to certain embodiments. The analyte sensor 1500 shown is a glucose sensor having a glucose sensing area 1501 including three electrodes—e.g., working electrode, reference electrode, and counter electrode. Electrical traces 1502 extend from the electrodes in the sensing area 1501 to corresponding contact points 1502 for connection to the electronics in the on-body sensor.

Glucose sensor 1500 also includes two traces 1504, 1505. Trace 1504 and 1505 are made of dissimilar materials (e.g., different metals or metal-alloys) that extend from corresponding contact points 1508, 1509, respectively, to a junction point 1506 located next to the glucose sensing area 1501. Contact points 1507, 1508 provide electrical connection to the electronics on the on-body sensor for measurement of the voltage produced by the junction of dissimilar materials.

In the embodiment shown, the two traces 1504,1505 of dissimilar materials are on the opposite side (e.g., back side) of the glucose sensor 1500 than the glucose sensing 1501 and electrode traces 1402 (e.g., on the front-side).

While the position of the junction point 1506 relative to the glucose sensing area 1501 may vary in different embodiments, having the junction point 1506 closer to the glucose sensing area 1501 provides a more accurate temperature estimate at the glucose sensing area 1501. In the embodiment shown, the junction point 1506 and the glucose sensing area 1501 are insulated from one another by the substrate itself, allowing the two traces 150 to extend further along the analyte sensor (e.g., directly opposite the glucose sensing area 1501).

It should be appreciated that in certain embodiments one of the two thermocouple traces could be made of the same material as the electrode traces. It should also be appreciated that in other embodiments one of the thermocouple traces may be on the opposite side of the sensor as the other thermocouple trace with a junction point near the glucose sensing area (e.g., implemented using a through-hole via).

In certain embodiments, the thermocouple sensor includes dissimilar metal traces on facing sides of two pieces of substrate (e.g., Kapton or another type of Polymer) that adhere together. In such case, the sensor is electrically isolated from the body as well as not crowding or disturbing the glucose sensing traces since the thermal sensing traces would be on a different plane. It should be appreciated that each of the dissimilar metals may be disposed on either inner facing side of the two pieces of substrate, independent of one another, such that a junction point is formed when the two pieces of substrate are combined. For example, one dissimilar metal may be one facing side while the other dissimilar metal is on the other facing side, and when the two facing sides are brought together, the two dissimilar metals forming a thermocouple junction point. This also applies to the other sensor concepts described herein as well.

Figure 15:
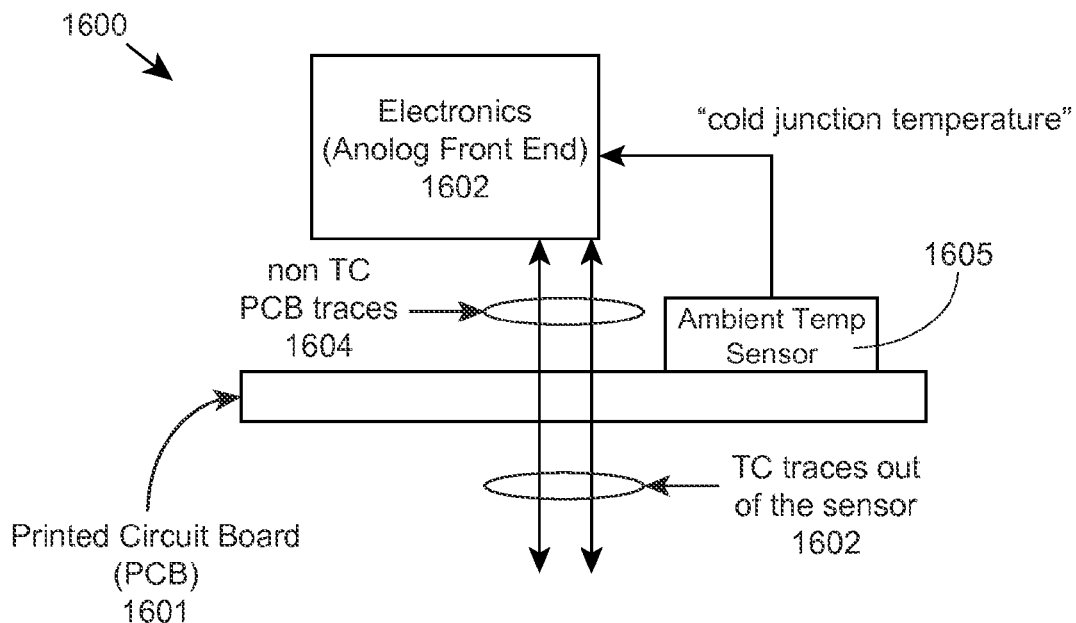
FIG. 15 illustrates a system block diagram of an on-body sensor having a thermocouple temperature sensor, according to certain embodiments.

FIG. 15 illustrates a system block diagram of an on-body sensor having a thermocouple temperature sensor, according to certain embodiments. On-body sensor 1600 includes a printed circuit board (PCB) 1601 having various electronic components thereon, including, for example, the analog front-end circuitry 1602. The thermocouple traces 1602 on the analyte sensor terminate on the PCB 1601 at contact points 1603 that are electrically coupled to non-thermocouple traces 1604 disposed on the PCB 1601. The non-thermocouple traces 1604 electrically couple the thermocouple traces 1602 to the analog front-end circuitry 1602 for measuring the voltage providing by the thermocouple.

In certain embodiments, such as shown, an ambient temperature sensor 1605 generates a signal that is used for "cold junction temperature" compensation in the system. In some instances, the "cold junction" temperature sensor 1605 is positioned at the point that the dissimilar metal traces 1602 are connected to the PCB 1601 in the on-body device. The voltage that is measured at the cold junction is a function of the temperature differential between the cold junction and the bonding point.

Thermocouple tape having two dissimilar metals is described in U.S. Pat. No. 3,729,343, filed on Jan. 8, 1971 and issued on Apr. 24, 1973, the entirety of which is hereby incorporated by reference.

In some aspects of the present disclosure, an analyte sensor is provided having a sensor substrate that includes two dissimilar materials on opposite sides with a thermocouple junction formed by a through-hole within the substrate.

In certain embodiments, a metal (or metal-alloy) trace is disposed on one side of the sensor substrate and a thermocouple trace (e.g., a conductive ink layer) on the opposite side of the substrate. A thermocouple junction is formed between the metal trace on one side and the conductive ink layer on the opposite side by a through-hole (e.g., a laser-drilled hole in the substrate). The conductive ink is disposed in the through-hole and forms a thermocouple junction between the metal trace on one side of the substrate and the conductive ink on the opposite side of the substrate. The conductive ink material may be made from any variety of materials suitable for creating a thermocouple junction—such as metal or metal alloys including, but not limited to, platinum, carbon, copper, iron, silver, etc.

In some aspects of the present disclosure, methods of making the above-mentioned thermocouple are provided. The methods include forming a metal or metal-alloy layer (e.g., a film plated with the metal or metal-alloy) on a sensor substrate; removing a portion of the metal or metal-alloy layer (e.g., by forming a laser-drilled hole); forming a conductive ink layer (e.g., a conductive ink trace) on the opposite side of the substrate as the metal or metal-ally layer; filling the through-hole with the conductive ink such that a thermocouple junction is formed between the conductive ink layer and the metal layer.

In certain embodiments, the metal or metal-alloy layer is also a sensor electrode. It should be appreciated that the conductive ink may be applied to the sensor substrate at various times. For example, in certain embodiments, the conductive ink layer may be applied before the through-hole is formed and again applied afterwards to fill the through-hole. In other embodiments, the conductive ink is applied after the through-hole to form the conductive ink layer and fill the through-hole.

Figure 16:
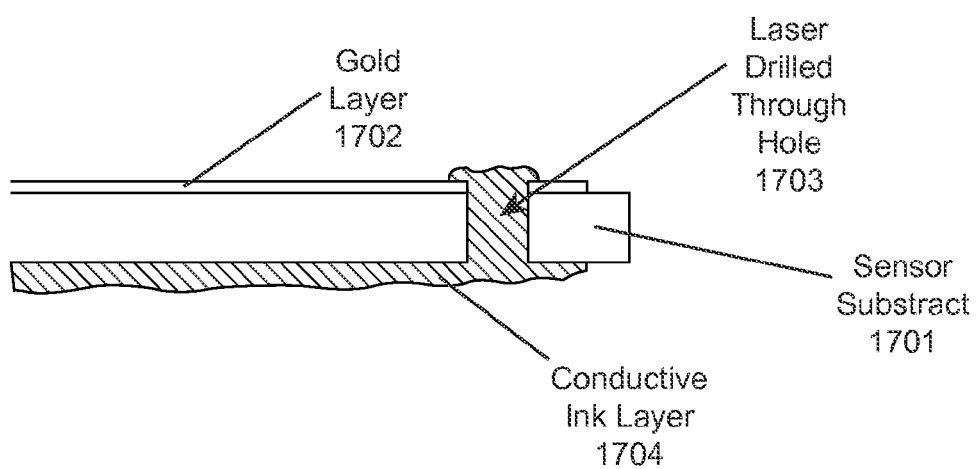
FIG. 16 illustrates a cross-sectional view of an analyte sensor substrate having a thermocouple junction, according to certain embodiments.

FIG. 16 illustrates a cross-sectional view of an analyte sensor substrate having a thermocouple junction, according to certain embodiments. The sensor substrate 1701 includes a layer of gold 1702 on one side of the substrate 1701. A through-hole 1703 is formed (e.g., via laser drilling) in the sensor substrate 1701 such that a portion of the layer of gold 1702 is removed. It should be appreciated that in other embodiments, the portion of the layer of gold 1702 at the through-hole may be removed before the laser drilled through-hole is formed—e.g., via an etching process, etc.— or otherwise disposed on the substrate 1701 in a printed pattern.

As shown in FIG. 16, a conductive ink layer 1704 is disposed on the opposite side of the sensor substrate 1701 as the layer of gold 1702. The through-hole 1703 is filled with the conductive ink such that the conductive ink layer 1703 and layer of gold 1703 are connected and a thermocouple junction formed.

Provided below is an example analysis. It should be appreciated that the example analysis is exemplary and is not meant to be limiting.

Example Analysis:

The following analysis is provided for exemplary purposes and is not meant to be limiting. The following analysis is based on the following: a sensor temperature range of 32 degrees C. to 42 degrees C. (typical body temperature of 37 degrees C.+/−5 degrees C.); a cold junction temperature range of 10 degrees C. to 50 degrees C.; thermocouple op amp similar to operation amplifier, OPA333, manufactured by Texas Instruments; an analog to digital converter (ADC) with a resolution less than 0.1 degrees C. and input voltage range of 0 to 400 mV; a modulator clock of 32768 Hz and conversion time of 125 mS (12 Bits); thermocouple sensitivity of 40.7 µV/degrees C. (e.g., type T Cu—Cn).

The analysis was also based on the OPA333 operation amplifier having the following features: low offset voltage of 10 µV(max); zero drift of 0.05 µV/PC(max); 0.01 Hz to 10 Hz noise of 1.1 µVpp; quiescent current of 17 µA; single-supply operation; supply voltage of 1.8V to 5.5V; rail-to-rail input/output; and microsize packages (SC70 and SOT23).

The results of the analysis were as follows: ADC 1 bit resolution=97.65 µV (12 bits-range of 400 mV); required minimum gain for thermocouple amplifier=2.4; maximum amplifier offset at ADC=24 µV (this is <1ADC count.); and type-T thermocouple output at 25.2 C=1.000 mV. Any calibration for the ADC slope and offset variation may be done by applying a known voltage during manufacture, for example.

The actual gain may be chosen much higher than minimum. The signal as seen by the thermocouple amplifier is the combination of the cold junction thermocouple and the sensor tip thermocouple. Exact calculations depend on the Seebeck voltage of the materials chosen.

In some instances, the cold junction thermocouple may vary in a temperature range that is higher than the sensor tip thermocouple and also lower than the sensor tip thermocouple. In such case, provided the cold junction temperature is known and sensitivity of the cold junction TC is known, a subtraction can be made that eliminates the cold junction contribution.

In some instances, the method for cold junction compensation uses a precision thermistor and requires no calibration.

In certain embodiments, one of the existing sensor electrode conductors is used as one of the thermocouple connections. Having a thermocouple output that is a differential voltage allows the sensor electrode conductor to be used and avoid using two additional connections to the sensor.

In some instances, carbon-polymer contacts are used with a thermocouple amplifier having high impedance input (non-inverting). This method helps avoid some thermal gradient issue and provides a more direct sensor temperature measurement.

Types of Temperature Sensors:

It should be appreciated that any variety of temperature sensors may be applicable to the subject matter of the present disclosure. The following temperature sensors are exemplary and are not intended to be limiting.

Thermistor:

In some aspects of the present disclosure, a thermistor sensor may be used for temperature compensation. The thermistor sensor may be disposed, for example, on a sensor tail that is positioned under the skin or near the tip of the analyte sensor. Example thermistors that may be implemented include, but are not limited to, surface mounted thermistors of type 0402, 0201, or 0105. Other example may include, but are not limited to, glass beads types, epoxy bead types, or small chip thermistors.

In some aspects of the present disclosure, the thermistor sensor is located in a thermally conductive structure such that it protrudes from the bottom of the skin worn transmitter device and provides a low thermal resistance path from the user's skin to a thermistor located in the electronics.

Figure 17:
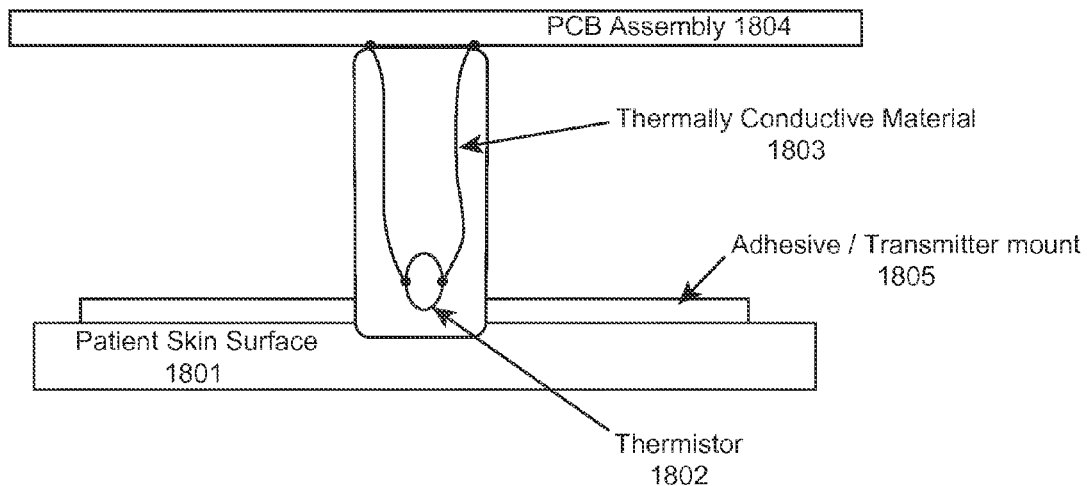
FIG. 17 illustrates an on-body sensor having a thermistor located in a thermally conductive structure such that it protrudes from the bottom of the on-body sensor, according to certain embodiments.

FIG. 17 illustrates an on-body sensor having a thermistor located in a thermally conductive structure such that it protrudes from the bottom of the on-body sensor, according to certain embodiments. On-body sensor 1800 is shown attached to a patient's skin surface 1801. The on-body sensor 1800 includes a thermistor 1802 that is disposed within a thermally conductive material 1803. The thermistor 1802 is electrically coupled to the on-body sensor's printed circuit board (PCB) 1804 for electrical coupling to the electronics on the PCB. The on-body sensor 1800 includes an adhesive layer 1805 that mounts the on body sensor 1800 to the patient's skin 1801. The thermally conductive material 1803 including the thermistor 1802 extends beyond the adhesive layer 1805 and protrudes from the on-body sensor 1800. The thermally conductive material 1803 contacts the skin 1801 of the patient to provide temperature measurement of the patient's skin 1801.

Resistive Temperature Device:

In some aspects of the present disclosure, a resistive temperature device (RTD) type sensor may be used for temperature compensation. For example, an RTD type sensor may be constructed from traces of metal (e.g., including, but not limited to, metals such as gold or platinum, or metal-alloys thereof) and deposited onto the sensor substrate. For instance, an RTD device such as a wire wound encapsulated device may be incorporated onto the sensor tail. The RTD device may then measure by the sensor electronics.

Pyro-Electric Sensor:

In some aspects of the present disclosure, a pyro-electric sensor may be used for temperature compensation. Pyro-electric sensors are sensitive to the infra-red light emitted by a warm object—e.g., the patients skin. In certain embodiments, an optical path is constructed from the patient's skin surface to the pyro-electric sensor that is located inside the electronics of the on-body unit. In this way, the skin surface temperature can be sensed and measured.

Semiconductor Sensor:

In some aspects of the present disclosure, a semiconductor sensor may be used for temperature compensation. In certain embodiments, a semiconductor sensor (such as, but not limited to, a diode junction or band gap type temperature sensor) is disposed (e.g., directly or disposed on a small device) either on the sensor tail or very close to the sensor insertion site to sense the glucose sensor temperature.

Temperature Compensation and Sensing Elements:

In some aspects of the present disclosure, analyte monitoring devices and systems include a sensing area that includes two or more sensing elements disposed on the sensing surface. For example, the sensing surface may be on a working electrode. Additional details regarding multiple sensing elements disposed on a sensing surface may be found in U.S. Provisional Patent Application No. 61/421, 371, filed Dec. 9, 2010, the entirety of which is incorporated herein by reference.

In certain embodiments, more than one sensing element is disposed at the sensing area (e.g., sensor tip). As demonstrated above, temperature compensation may be performed when multiple sensing elements are at the sensor tip. Furthermore, it has been shown that very small sensing layer areas improve repeatability of the sensor sensitivity. Further, multiple sensing dots may promote the collection of sufficient current for generating a viable signal.

In certain embodiments, on-body sensors are provided having multiple sensing elements at the sensing area, wherein some of the sensing elements are made of a different material than other sensing elements. For example, some of the sensing elements are made of a first material and the other sensing elements are made of a second material. The different materials have different temperature responses. Thus, current from the sensing elements of one material may be collected and compared to the current from the sensing elements of the second material to determine the temperature at the sensor tip. In this way, a temperature measurement is performed almost directly at the sensor tip.

Figure 18:
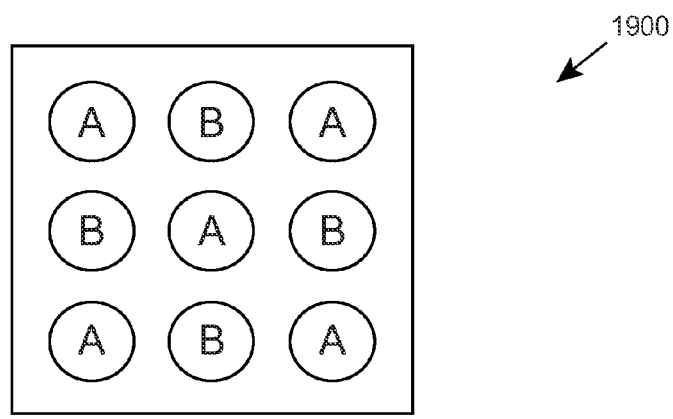
FIG. 18 illustrates a top view of multiple sensing elements disposed on a sensing surface, according to certain embodiments.

FIG. 18 illustrates a top view of multiple sensing elements disposed on a sensing surface, according to certain embodiments. Sensing surface 1900 is shown including sensing elements A and sensing elements B. Sensing elements A are made of a first material and sensing elements B are made from a different material than sensing elements A. The different materials (e.g., sensing chemistries) have different temperature dependencies and thus different temperature responses. Current from sensing elements A are compared to current from sensing elements B to determine the temperature at the sensor tip. In this way, a temperature measurement is performed almost directly at the sensor tip.

It should be appreciated that the number of sensing elements may vary in different embodiments. Further, it should also be appreciated that the sensing elements may be disposed on the sensing surface in a variety of shapes and patterns, and should not be limited to the embodiment shown in FIG. 18.

Temperature Compensation and Electrodes with Different Chemistries

In some aspects of the present disclosure, temperature compensation is performed when multiple working electrodes having different chemistries are present. For example, in some instances, an OBU may include a double sensor having different enzymes. For example, an on-body sensor may include two working electrodes having different sensing chemistries on each electrode. Because the sensing chemistry is different, their temperature dependencies are different. However, in a limited temperature range, the functional dependence is the same. Sensor current may be determined by, for example:

$$I \sim (1+a)^{(T-T_{nom})}$$

where I is the sensor current, a is a known positive constant much less than unity, and $T_{nom}$ is a set temperature. The sensor current also depends on the surface area, the amount of sensing material, and efficiency of the sensing chemistry and diffusion controlling membrane—collectively referred to herein as factor A. The ratio of the sensor currents is:

$$\frac{I_1}{I_2} = \frac{A_1(1+a_1)^{(T-T_{nom})}}{A_2(1+a_2)^{(T-T_{nom})}}$$

Solving for T:

$$T = T_{nom} + \frac{\ln(I_1/I_2) - \ln(A_1/A_2)}{\ln\left(\frac{1+a_1}{1+a_2}\right)}$$

All of the quantities on the rights side of the equation are, in principle, known. If A1 is set equal to A2, then I1=I2 when $T=T_{nom}$.

Once T is calculated, the sensor current is compensated for temperature and the analyte level calculated.

Temperature Compensation Using a Known Reservoir

In some aspects of the present disclosure, a secondary sensing element is used to directly measure the effect of temperature on the chemistry, independent of the user's analyte level (e.g., blood glucose). This measurement data is used in conjunction with measurement data from the primary sensor, which is dependent on temperature and the user's blood glucose, to remove the temperature effect. In this way, a more accurate estimate of the user's blood glucose concentration may be achieved. Moreover, temperature variation may be automatically compensated without implementing the mathematical model used in the some of the two sensor models described above, and instead use the chemistry to compensate itself.

In certain embodiments, an on-body sensor includes a secondary sensing element and a known volume of glucose at a known concentration (e.g., as provided by a "reservoir"). Having a secondary sensing element and a known volume of glucose at a known concentration (e.g., as provided by a "reservoir") enables temperature variation to be "cancelled out" without having to model the actual temperature variation of the chemistry. The secondary sensing element may be disposed under the skin, for example, and the secondary dot and reservoir isolated from the rest of the system. In some instances, the reservoir is physically small, but lasts for the entire sensor life.

In certain embodiments, this type of thermometer may be operated in two ways; in the linear range, and in saturation. In the linear range, the current is a function of the glucose concentration and the temperature. The glucose concentration as a function of time is calculated by keeping track of the total charge collected. This yields the expected current at the nominal temperature. Any difference between the expected current and the actual current may be attributed to temperature variation. In certain embodiments, a membrane is disposed between the sensing element and the reservoir for operation in the linear range.

In saturation, the current is determined solely by enzyme activity. Since this is a function of temperature, temperature variation may be measured directly. When operating in saturation, the membrane may be thinner, even if glucose concentrations should need to remain high.

In certain embodiments, the reservoir is kept away from the sensing element until the sensor has started, whether operating in either the linear range or saturation. In this way, any time limit to the stability of the sensing layer in a wet environment is accounted for. For example, a temporary barrier may be implemented that ceases to separate the second sensing area and the reservoir when the analyte sensor is transcutaneously positioned—e.g., a barrier that is broken, dissolved, or otherwise removed upon the insertion process.

In certain embodiments, the secondary sensor signal is an analog signal which controls the gain of the primary sensor circuit. The gain control may be linear since the secondary signal itself contains the complex non-linear variation that may be more difficult to model.

In certain embodiments, the secondary sensor signal is sampled and the primary signal gain modified in a software algorithm. The software algorithm may be executed by a processing device in the on-body electronics for example. The gain control may be linear since the secondary signal itself contains the complex non-linear variation that may be more difficult to model.

Provided below are example analyses related to using a known reservoir. The example analyses are exemplary and are not meant to be limiting.

Example 1

A sensing dot with an area of 0.01 square millimeter (1/10 the area of the primary sensing dot), and a cubical reservoir of side length 0.5 millimeters filled with 10 millimolar glucose solution starts with a current of 6 nA, and finishes with a current of 0.6 nA.

Example 2

$a = 6.02 \times 10^{23}$ molecules/mole $q = 1.6 \times 10^{-19}$ C/molecules $T = 122$ hours $= 439,200$ seconds (sensor life)

$\beta = 6$ nA/(mM/Liter)/mm$^2$ $\quad = 6$ (A/meter$^2$)(1/(M/Liter))

$\quad = 10^{-23}$ (A/meter$^2$)(1/molecule)(Liter)

$\quad = 10^{-26}$ (Amp)(m)/molecule

Example 3

Time Evolution of Glucose Concentration $N = $ # of molecules in reservoir $dN/dt = -\alpha I$ $\alpha = $ molecules/(Amp $\times$ sec) $=$ molecules/c $= 1/q$ $n = $ # molecules/m$^3$ concentration $V = $ reservoir volume $dn/dt = -I/(qV)$ $I = \beta A n$ $A = $ m$^2$ area of sensing dot $dn/dt = -\beta A n/(qV)$ $n(t) = n_0 \exp(-\beta A n/(qV))$ $\quad = n_0 \exp(-6.25 \times 10^{-8} At/V)$ Example 4

Time Constant vs Sensor Life $6.25 \times 10^{-8}$ (AT)/V $\approx 2$
$A = 10^{-8}$ m$^2$
$T = 4.4 \times 10^5$ s
$V \approx 1.4 \times 10^{-10}$ m3
Cube: 0.5 mm on a side
Maximum and Minimum Concentrations and Currents
$\beta A = 0.6$ nA/(mM/Liter)
Maximum current $I_o = 6$ nA
Maximum concentration $n_o = 10$ mM/L
After 5 days (and 2 time constants) $I_f \approx 0.6$ nA It should be understood that techniques introduced above can be implemented by programmable circuitry programmed or configured by software and/or firmware, or they can be implemented entirely by special-purpose "hard-wired" circuitry, or in a combination of such forms. Such special-purpose circuitry (if any) can be in the form of, for example, one or more application-specific integrated circuits (ASICS), programmable logic devices (PLDs), field-programmable gate arrays (FPGAs), etc.

Software or firmware implementing the techniques introduced herein may be stored on a machine-readable storage medium and may be executed by one or more general-purpose or special-purpose programmable microprocessors. A "machine-readable medium", as the term is used herein, includes any mechanism that can store information in a form accessible by a machine (a machine may be, for example, a computer, network device, cellular phone, personal digital assistant (PDA), manufacturing took, any device with one or more processors, etc.). For example, a machine-accessible medium includes recordable/non-recordable media (e.g., read-only memory (ROM); random access memory (RAM); magnetic disk storage media; optical storage media; flash memory devices; etc.), etc.

The term "logic", as used herein, can include, for example, special purpose hardwired circuitry, software and/or firmware in conjunction with programmable circuitry, or a combination thereof.

Electrochemical Sensors

Embodiments of the present disclosure relate to methods and devices for detecting at least one analyte, including glucose, in body fluid. Embodiments relate to the continuous and/or automatic in vivo monitoring of the level of one or more analytes using a continuous analyte monitoring system that includes an analyte sensor at least a portion of which is to be positioned beneath a skin surface of a user for a period of time and/or the discrete monitoring of one or more analytes using an in vitro blood glucose ("BG") meter and an analyte test strip. Embodiments include combined or combinable devices, systems and methods and/or transferring data between an in vivo continuous system and an in vivo system. In certain embodiments, the systems, or at least a portion of the systems, are integrated into a single unit.

An analyte sensor as described herein may be an in vivo analyte sensor or an in vitro sensor (i.e., a discrete monitoring test strip). Such a sensor can be formed on a substrate, e.g., a substantially planar substrate. In certain embodiments, the sensor is a wire, e.g., a working electrode wire inner portion with one or more other electrodes associated (e.g., on, including wrapped around) therewith. The sensor may also include at least one counter electrode (or counter/reference electrode) and/or at least one reference electrode or at least one reference/counter electrode.

Accordingly, embodiments include analyte monitoring devices and systems that include an analyte sensor at least a portion of which is positionable beneath the skin surface of the user for the in vivo detection of an analyte, including glucose, lactate, ketones, and the like, in a body fluid. Embodiments include wholly implantable analyte sensors and analyte sensors in which only a portion of the sensor is positioned under the skin and a portion of the sensor resides above the skin, e.g., for contact to a sensor control unit (which may include a transmitter), a receiver/display unit, transceiver, processor, etc. The sensor may be, for example, subcutaneously positionable in a user for the continuous or periodic monitoring of a level of an analyte in the user's interstitial fluid. For the purposes of this description, continuous monitoring and periodic monitoring will be used interchangeably, unless noted otherwise. The sensor response may be correlated and/or converted to analyte levels in blood or other fluids. In certain embodiments, an analyte sensor may be positioned in contact with interstitial fluid to detect the level of glucose, which detected glucose may be used to infer the glucose level in the user's bloodstream. Analyte sensors may be insertable into a vein, artery, or other portion of the body containing fluid. Embodiments of the analyte sensors may be configured for monitoring the level of the analyte over a time period which may range from seconds, minutes, hours, days, weeks, to months, or longer.

In certain embodiments, the analyte sensors, such as glucose sensors, are capable of in vivo detection of an analyte for one hour or more, e.g., a few hours or more, e.g., a few days or more, e.g., three or more days, e.g., five days or more, e.g., seven days or more, e.g., several weeks or more, or one month or more. Future analyte levels may be predicted based on information obtained, e.g., the current analyte level at time $t_0$, the rate of change of the analyte, etc. Predictive alarms may notify the user of a predicted analyte level that may be of concern in advance of the user's analyte level reaching the future predicted analyte level. This provides the user an opportunity to take corrective action.

FIG. 1 shows a data monitoring and management system such as, for example, an analyte (e.g., glucose) monitoring system 100 in accordance with certain embodiments. Aspects of the subject disclosure are further described primarily with respect to glucose monitoring devices and systems, and methods of glucose detection, for convenience only and such description is in no way intended to limit the scope of the embodiments. It is to be understood that the analyte monitoring system may be configured to monitor a variety of analytes at the same time or at different times.

Analytes that may be monitored include, but are not limited to, acetyl choline, amylase, bilirubin, cholesterol, chorionic gonadotropin, glycosylated hemoglobin (HbA1c), creatine kinase (e.g., CK-MB), creatine, creatinine, DNA, fructosamine, glucose, glucose derivatives, glutamine, growth hormones, hormones, ketones, ketone bodies, lactate, peroxide, prostate-specific antigen, prothrombin, RNA, thyroid stimulating hormone, and troponin. The concentration of drugs, such as, for example, antibiotics (e.g., gentamicin, vancomycin, and the like), digitoxin, digoxin, drugs of abuse, theophylline, and warfarin, may also be monitored. In embodiments that monitor more than one analyte, the analytes may be monitored at the same or different times.

The analyte monitoring system 100 includes an analyte sensor 101, a data processing unit 102 connectable to the sensor 101, and a primary receiver unit 104. In some instances, the primary receiver unit 104 is configured to communicate with the data processing unit 102 via a communication link 103. In certain embodiments, the primary receiver unit 104 may be further configured to transmit data to a data processing terminal 105 to evaluate or otherwise process or format data received by the primary receiver unit 104. The data processing terminal 105 may be configured to receive data directly from the data processing unit 102 via a communication link 107, which may optionally be configured for bi-directional communication. Further, the data processing unit 102 may include a transmitter or a transceiver to transmit and/or receive data to and/or from the primary receiver unit 104 and/or the data processing terminal 105 and/or optionally a secondary receiver unit 106.

Also shown in FIG. 1 is an optional secondary receiver unit 106 which is operatively coupled to the communication link 103 and configured to receive data transmitted from the data processing unit 102. The secondary receiver unit 106 may be configured to communicate with the primary receiver unit 104, as well as the data processing terminal 105. In certain embodiments, the secondary receiver unit 106 may be configured for bi-directional wireless communication with each of the primary receiver unit 104 and the data processing terminal 105. As discussed in further detail below, in some instances, the secondary receiver unit 106 may be a de-featured receiver as compared to the primary receiver unit 104, for instance, the secondary receiver unit 106 may include a limited or minimal number of functions and features as compared with the primary receiver unit 104. As such, the secondary receiver unit 106 may include a smaller (in one or more, including all, dimensions), compact housing or embodied in a device including a wrist watch, arm band, PDA, mp3 player, cell phone, etc., for example. Alternatively, the secondary receiver unit 106 may be configured with the same or substantially similar functions and features as the primary receiver unit 104. The secondary receiver unit 106 may include a docking portion configured to mate with a docking cradle unit for placement by, e.g., the bedside for night time monitoring, and/or a bi-directional communication device. A docking cradle may recharge a power supply.

Only one analyte sensor 101, data processing unit 102 and data processing terminal 105 are shown in the embodiment of the analyte monitoring system 100 illustrated in FIG. 1. However, it will be appreciated by one of ordinary skill in the art that the analyte monitoring system 100 may include more than one sensor 101 and/or more than one data processing unit 102, and/or more than one data processing terminal 105. Multiple sensors may be positioned in a user for analyte monitoring at the same or different times. In certain embodiments, analyte information obtained by a first sensor positioned in a user may be employed as a comparison to analyte information obtained by a second sensor. This may be useful to confirm or validate analyte information obtained from one or both of the sensors. Such redundancy may be useful if analyte information is contemplated in critical therapy-related decisions. In certain embodiments, a first sensor may be used to calibrate a second sensor.

The analyte monitoring system 100 may be a continuous monitoring system, or semi-continuous, or a discrete monitoring system. In a multi-component environment, each component may be configured to be uniquely identified by one or more of the other components in the system so that communication conflict may be readily resolved between the various components within the analyte monitoring system 100. For example, unique IDs, communication channels, and the like, may be used.

In certain embodiments, the sensor 101 is physically positioned in or on the body of a user whose analyte level is being monitored. The sensor 101 may be configured to at least periodically sample the analyte level of the user and convert the sampled analyte level into a corresponding signal for transmission by the data processing unit 102. The data processing unit 102 is coupleable to the sensor 101 so that both devices are positioned in or on the user's body, with at least a portion of the analyte sensor 101 positioned transcutaneously. The data processing unit may include a fixation element, such as an adhesive or the like, to secure it to the user's body. A mount (not shown) attachable to the user and mateable with the data processing unit 102 may be used. For example, a mount may include an adhesive surface. The data processing unit 102 performs data processing functions, where such functions may include, but are not limited to, filtering and encoding of data signals, each of which corresponds to a sampled analyte level of the user, for transmission to the primary receiver unit 104 via the communication link 103. In certain embodiments, the sensor 101 or the data processing unit 102 or a combined sensor/data processing unit may be wholly implantable under the skin surface of the user.

In certain embodiments, the primary receiver unit 104 may include an analog interface section including an RF receiver and an antenna that is configured to communicate with the data processing unit 102 via the communication link 103, and a data processing section for processing the received data from the data processing unit 102 including data decoding, error detection and correction, data clock generation, data bit recovery, etc., or any combination thereof.

In operation, the primary receiver unit 104 in certain embodiments is configured to synchronize with the data processing unit 102 to uniquely identify the data processing unit 102, based on, for example, an identification information of the data processing unit 102, and thereafter, to periodically receive signals transmitted from the data processing unit 102 associated with the monitored analyte levels detected by the sensor 101.

Referring again to FIG. 1, the data processing terminal 105 may include a personal computer, a portable computer including a laptop or a handheld device (e.g., a personal digital assistant (PDA), a telephone including a cellular phone (e.g., a multimedia and Internet-enabled mobile phone including an iPhone™, a Blackberry®, or similar phone), an mp3 player (e.g., an iPOD™, etc.), a pager, and the like), and/or a drug delivery device (e.g., an infusion device), each of which may be configured for data communication with the receiver via a wired or a wireless connection. Additionally, the data processing terminal 105 may further be connected to a data network (not shown) for storing, retrieving, updating, and/or analyzing data corresponding to the detected analyte level of the user.

The data processing terminal 105 may include a drug delivery device (e.g., an infusion device), such as an insulin infusion pump or the like, which may be configured to administer a drug (e.g., insulin) to the user, and which may be configured to communicate with the primary receiver unit 104 for receiving, among others, the measured analyte level. Alternatively, the primary receiver unit 104 may be configured to integrate an infusion device therein so that the primary receiver unit 104 is configured to administer an appropriate drug (e.g., insulin) to users, for example, for administering and modifying basal profiles, as well as for determining appropriate boluses for administration based on, among others, the detected analyte levels received from the data processing unit 102. An infusion device may be an external device or an internal device, such as a device wholly implantable in a user.

In certain embodiments, the data processing terminal 105, which may include an infusion device, e.g., an insulin pump, may be configured to receive the analyte signals from the data processing unit 102, and thus, incorporate the functions of the primary receiver unit 104 including data processing for managing the user's insulin therapy and analyte monitoring. In certain embodiments, the communication link 103, as well as one or more of the other communication interfaces shown in FIG. 1, may use one or more wireless communication protocols, such as, but not limited to: an RF communication protocol, an infrared communication protocol, a Bluetooth enabled communication protocol, an 802.11x wireless communication protocol, or an equivalent wireless communication protocol which would allow secure, wireless communication of several units (for example, per Health Insurance Portability and Accountability Act (HIPPA) requirements), while avoiding potential data collision and interference.

Figure 2:
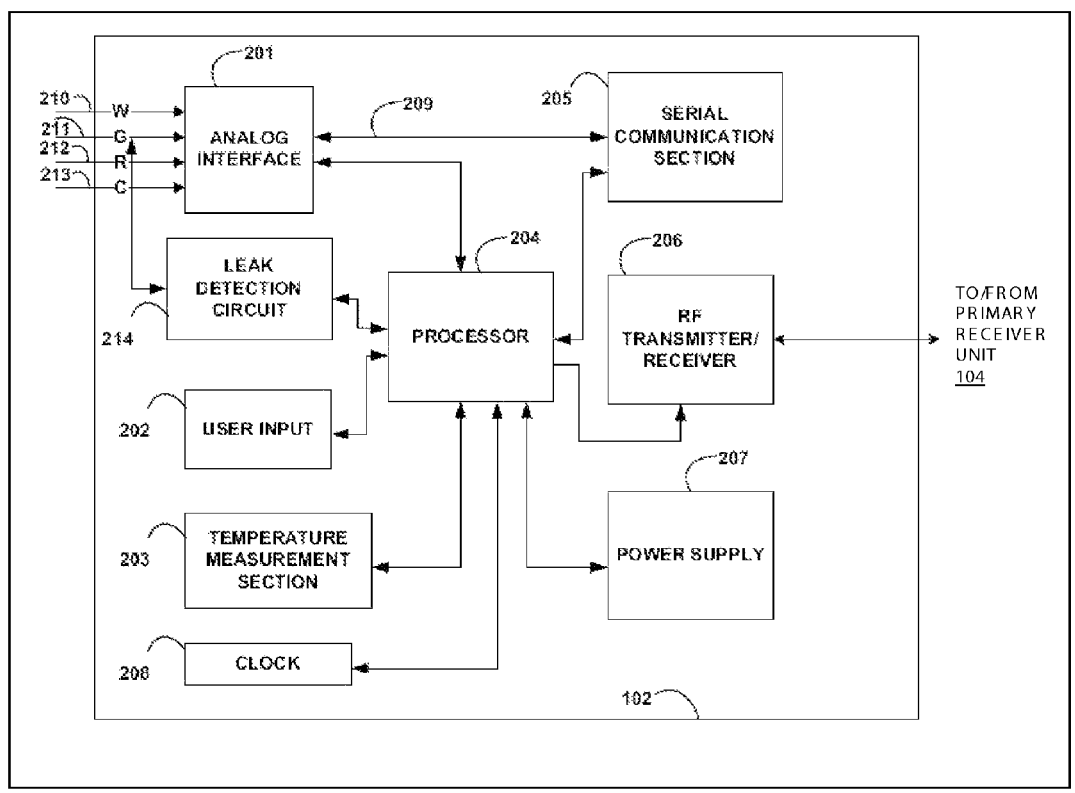
FIG. 2 shows a block diagram of an embodiment of a data processing unit of the analyte monitoring system shown in FIG. 1, according to certain embodiments.

FIG. 2 shows a block diagram of an embodiment of a data processing unit 102 of the analyte monitoring system shown in FIG. 1. User input and/or interface components may be included or a data processing unit may be free of user input and/or interface components. In certain embodiments, one or more application-specific integrated circuits (ASIC) may be used to implement one or more functions or routines associated with the operations of the data processing unit (and/or receiver unit) using for example one or more state machines and buffers.

As can be seen in the embodiment of FIG. 2, the analyte sensor 101 (FIG. 1) includes four contacts, three of which are electrodes: a work electrode (W) 210, a reference electrode (R) 212, and a counter electrode (C) 213, each operatively coupled to the analog interface 201 of the data processing unit 102. This embodiment also shows an optional guard contact (G) 211. Fewer or greater electrodes may be employed. For example, the counter and reference electrode functions may be served by a single counter/reference electrode. In some cases, there may be more than one working electrode and/or reference electrode and/or counter electrode, etc.

Figure 3:
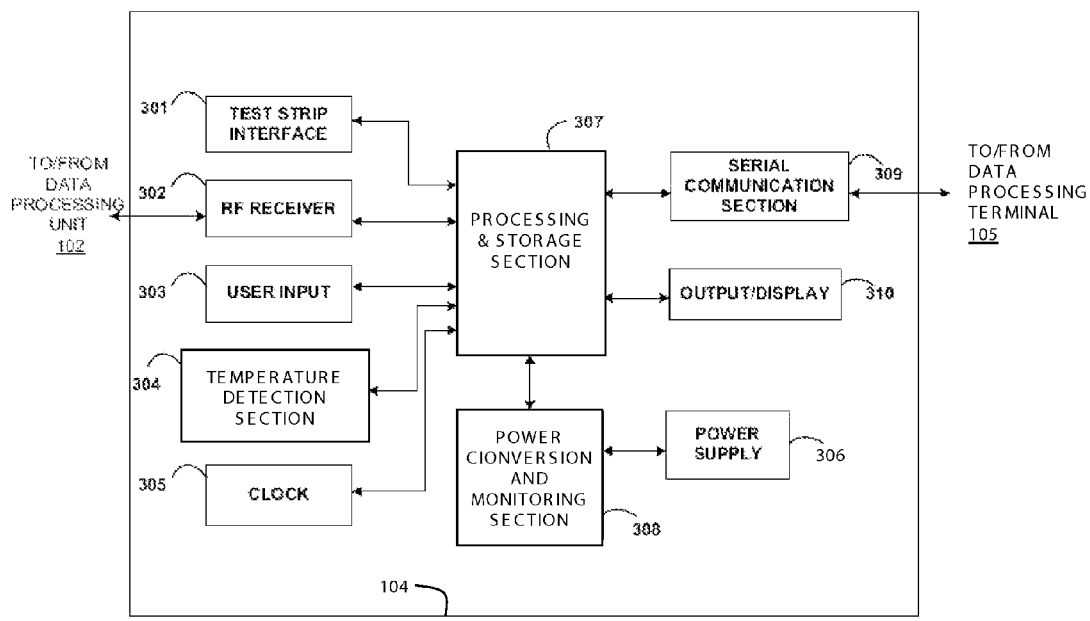
FIG. 3 shows a block diagram of an embodiment of the primary receiver unit of the analyte monitoring system of FIG. 1, according to certain embodiments.

FIG. 3 is a block diagram of an embodiment of a receiver/monitor unit such as the primary receiver unit 104 of the analyte monitoring system shown in FIG. 1. The primary receiver unit 104 includes one or more of: a test strip interface 301, an RF receiver 302, a user input 303, an optional temperature detection section 304, and a clock 305, each of which is operatively coupled to a processing and storage section 307. The primary receiver unit 104 also includes a power supply 306 operatively coupled to a power conversion and monitoring section 308. Further, the power conversion and monitoring section 308 is also coupled to the processing and storage section 307. Moreover, also shown are a receiver serial communication section 309, and an output 310, each operatively coupled to the processing and storage section 307. The primary receiver unit 104 may include user input and/or interface components or may be free of user input and/or interface components.

In certain embodiments, the test strip interface 301 includes an analyte testing portion (e.g., a glucose level testing portion) to receive a blood (or other body fluid sample) analyte test or information related thereto. For example, the test strip interface 301 may include a test strip port to receive a test strip (e.g., a glucose test strip). The device may determine the analyte level of the test strip, and optionally display (or otherwise notice) the analyte level on the output 310 of the primary receiver unit 104. Any suitable test strip may be employed, e.g., test strips that only require a very small amount (e.g., 3 microliters or less, e.g., 1 microliter or less, e.g., 0.5 microliters or less, e.g., 0.1 microliters or less), of applied sample to the strip in order to obtain accurate glucose information. Embodiments of test strips include, e.g., FreeStyle® or Precision® blood glucose test strips from Abbott Diabetes Care Inc. (Alameda, Calif.). Glucose information obtained by an in vitro glucose testing device may be used for a variety of purposes, computations, etc. For example, the information may be used to calibrate sensor 101, confirm results of sensor 101 to increase the confidence thereof (e.g., in instances in which information obtained by sensor 101 is employed in therapy related decisions), etc.

In further embodiments, the data processing unit 102 and/or the primary receiver unit 104 and/or the secondary receiver unit 106, and/or the data processing terminal/infusion device 105 may be configured to receive the analyte value wirelessly over a communication link from, for example, a blood glucose meter. In further embodiments, a user manipulating or using the analyte monitoring system 100 (FIG. 1) may manually input the analyte value using, for example, a user interface (for example, a keyboard, keypad, voice commands, and the like) incorporated in one or more of the data processing unit 102, the primary receiver unit 104, secondary receiver unit 106, or the data processing terminal/infusion device 105.

Additional detailed descriptions of exemplary sensors are provided in U.S. Pat. Nos. 5,262,035; 5,264,104; 5,262,305; 5,320,715; 5,593,852; 6,175,752; 6,650,471; 6,746,582, and 7,811,231, each of which is incorporated herein by reference in their entirety.

Figure 4:
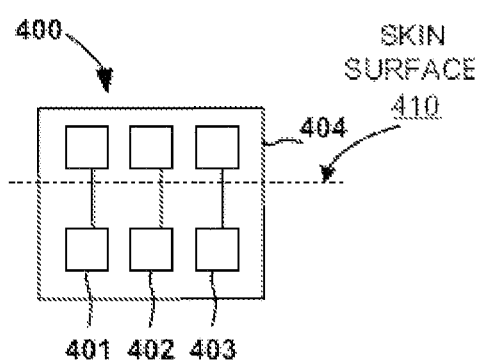
FIG. 4 shows a schematic diagram of an embodiment of an analyte sensor, according to certain embodiments.

FIG. 4 schematically shows an embodiment of an analyte sensor 400 in accordance with the embodiments of the present disclosure. This sensor embodiment includes electrodes 401, 402 and 403 on a base 404. Electrodes (and/or other features) may be applied or otherwise processed using any suitable technology, e.g., chemical vapor deposition (CVD), physical vapor deposition, sputtering, reactive sputtering, printing, coating, ablating (e.g., laser ablation), painting, dip coating, etching, and the like. Materials include, but are not limited to, any one or more of aluminum, carbon (including graphite), cobalt, copper, gallium, gold, indium, iridium, iron, lead, magnesium, mercury (as an amalgam), nickel, niobium, osmium, palladium, platinum, rhenium, rhodium, selenium, silicon (e.g., doped polycrystalline silicon), silver, tantalum, tin, titanium, tungsten, uranium, vanadium, zinc, zirconium, mixtures thereof, and alloys, oxides, or metallic compounds of these elements.

The analyte sensor 400 may be wholly implantable in a user or may be configured so that only a portion is positioned within (internal) a user and another portion outside (external) a user. For example, the sensor 400 may include a first portion positionable above a surface of the skin 410, and a second portion positioned below the surface of the skin. In such embodiments, the external portion may include contacts (connected to respective electrodes of the second portion by traces) to connect to another device also external to the user such as a transmitter unit. While the embodiment of FIG. 4 shows three electrodes side-by-side on the same surface of base 404, other configurations are contemplated, e.g., fewer or greater electrodes, some or all electrodes on different surfaces of the base or present on another base, some or all electrodes stacked together, electrodes of differing materials and dimensions, etc.

The substrate may be formed using a variety of non-conducting materials, including, for example, polymeric or plastic materials and ceramic materials. Suitable materials for a particular sensor may be determined, at least in part, based on the desired use of the sensor and properties of the materials.

In certain embodiments, the substrate is flexible. For example, if the sensor is configured for implantation into a user, then the sensor may be made flexible (although rigid sensors may also be used for implantable sensors) to reduce pain to the user and damage to the tissue caused by the implantation of and/or the wearing of the sensor. A flexible substrate often increases the user's comfort and allows a wider range of activities. Suitable materials for a flexible substrate include, for example, non-conducting plastic or polymeric materials and other non-conducting, flexible, deformable materials. Examples of useful plastic or polymeric materials include thermoplastics such as polycarbonates, polyesters (e.g., polyethylene terephthalate (PET)), polyvinyl chloride (PVC), polyurethanes, polyethers, polyamides, polyimides, or copolymers of these thermoplastics, such as PETG (glycol-modified polyethylene terephthalate).

In other embodiments, the sensors are made using a relatively rigid substrate to, for example, provide structural support against bending or breaking. Examples of rigid materials that may be used as the substrate include poorly conducting ceramics, such as aluminum oxide and silicon dioxide. An implantable sensor having a rigid substrate may have a sharp point and/or a sharp edge to aid in implantation of a sensor without an additional insertion device.

It will be appreciated that for many sensors and sensor applications, both rigid and flexible sensors will operate adequately. The flexibility of the sensor may also be controlled and varied along a continuum by changing, for example, the composition and/or thickness of the substrate.

In addition to considerations regarding flexibility, it is often desirable that implantable sensors should have a substrate which is physiologically harmless, for example, a substrate approved by a regulatory agency or private institution for in vivo use.

The sensor may include optional features to facilitate insertion of an implantable sensor. For example, the sensor may be pointed at the tip to ease insertion. In addition, the sensor may include a barb which assists in anchoring the sensor within the tissue of the user during operation of the sensor. However, the barb may be small enough so that little damage is caused to the subcutaneous tissue when the sensor is removed for replacement.

Electronics Unit

A sensor electronics unit such as a sensor control unit can be integrated in the sensor, part or all of which is subcutaneously implanted or it can be configured to be placed on the skin of a user. The sensor control unit is optionally formed in a shape that is comfortable to the user and which may permit concealment, for example, under a user's clothing. The thigh, leg, upper arm, shoulder, or abdomen are convenient parts of the user's body for placement of the sensor control unit to maintain concealment. However, the sensor control unit may be positioned on other portions of the user's body. Certain embodiments of the sensor control unit has a thin, oval shape to enhance concealment. However, other shapes and sizes may be used.

The particular profile, as well as the height, width, length, weight, and volume of the sensor control unit may vary and depends, at least in part, on the components and associated functions included in the sensor control unit. In general, the sensor control unit includes a housing may be formed as a single integral unit that rests on the skin of the user. The housing may contain most or all of the electronic components of the sensor control unit.

The housing of the sensor control unit may be formed using a variety of materials, including, for example, plastic and polymeric materials, such as rigid thermoplastics and engineering thermoplastics. Suitable materials include, for example, polyvinyl chloride, polyethylene, polypropylene, polystyrene, ABS polymers, and copolymers thereof. The housing of the sensor control unit may be formed using a variety of techniques including, for example, injection molding, compression molding, casting, and other molding methods. Hollow or recessed regions may be formed in the housing of the sensor control unit. The electronic components of the sensor control unit and/or other items, including a battery or a speaker for an audible alarm, may be placed in the hollow or recessed areas.

The sensor control unit may be attached to the skin of the user, for example, by adhering the sensor control unit directly to the skin of the user with an adhesive provided on at least a portion of the housing of the sensor control unit which contacts the skin or by suturing the sensor control unit to the skin through suture openings in the sensor control unit.

When positioned on the skin of a user, the sensor and the electronic components within the sensor control unit are coupled via conductive contacts. The one or more working electrodes, counter electrode (or counter/reference electrode), optional reference electrode, and optional temperature probe are attached to individual conductive contacts. For example, the conductive contacts are provided on the interior of the sensor control unit. Other embodiments of the sensor control unit have the conductive contacts disposed on the exterior of the housing. The placement of the conductive contacts is such that they are in contact with the contact pads on the sensor when the sensor is properly positioned within the sensor control unit.

Sensor Electronics

The sensor electronics also may include at least a portion of the electronic components that operate the sensor and the analyte monitoring device system. The electronic components of the sensor control unit may include a power supply for operating the sensor control unit and the sensor, a sensor circuit for obtaining signals from and operating the sensor, a measurement circuit that converts sensor signals to a desired format, and a processing circuit that, at minimum, obtains signals from the sensor circuit and/or measurement circuit and provides the signals to an optional transmitter. In certain embodiments, the processing circuit may also partially or completely evaluate the signals from the sensor and convey the resulting data to the optional transmitter and/or activate an optional alarm system if the analyte level exceeds a threshold. The processing circuit often includes digital logic circuitry.

The sensor control unit may optionally contain a transmitter for transmitting the sensor signals or processed data from the processing circuit to a receiver/display unit; a data storage unit for temporarily or permanently storing data from the processing circuit; a temperature probe circuit for receiving signals from and operating a temperature probe; a reference voltage generator for providing a reference voltage for comparison with sensor-generated signals; and/or a watchdog circuit that monitors the operation of the electronic components in the sensor control unit.

Moreover, the sensor control unit may also include digital and/or analog components utilizing semiconductor devices, including transistors. To operate these semiconductor devices, the sensor control unit may include other components including, for example, a bias control generator to correctly bias analog and digital semiconductor devices, an oscillator to provide a clock signal, and a digital logic and timing component to provide timing signals and logic operations for the digital components of the circuit.

As an example of the operation of these components, the sensor circuit and the optional temperature probe circuit provide raw signals from the sensor to the measurement circuit. The measurement circuit converts the raw signals to a desired format, using for example, a current-to-voltage converter, current-to-frequency converter, and/or a binary counter or other indicator that produces a signal proportional to the absolute value of the raw signal. This may be used, for example, to convert the raw signal to a format that can be used by digital logic circuits. The processing circuit may then, optionally, evaluate the data and provide commands to operate the electronics.

Calibration

Analyte sensors may be configured to require no system calibration or no user calibration. For example, a sensor may be factory calibrated and need not require further calibrating. In certain embodiments, calibration may be required, but may be done without user intervention, i.e., may be automatic. In those embodiments in which calibration by the user is required, the calibration may be according to a predetermined schedule or may be dynamic, i.e., the time for which may be determined by the system on a real-time basis according to various factors, including, but not limited to, glucose concentration and/or temperature and/or rate of change of glucose, etc.

In addition to a transmitter, an optional receiver may be included in the sensor control unit. In some cases, the transmitter is a transceiver, operating as both a transmitter and a receiver. The receiver may be used to receive calibration data for the sensor. The calibration data may be used by the processing circuit to correct signals from the sensor. This calibration data may be transmitted by the receiver/display unit or from some other source such as a control unit in a doctor's office. In addition, the optional receiver may be used to receive a signal from the receiver/display units to direct the transmitter, for example, to change frequencies or frequency bands, to activate or deactivate the optional alarm system and/or to direct the transmitter to transmit at a higher rate.

Calibration data may be obtained in a variety of ways. For instance, the calibration data may be factory-determined calibration measurements which can be input into the sensor control unit using the receiver or may alternatively be stored in a calibration data storage unit within the sensor control unit itself (in which case a receiver may not be needed). The calibration data storage unit may be, for example, a readable or readable/writeable memory circuit. In some cases, a system may only need to be calibrated once during the manufacturing process, where recalibration of the system is not required.

If necessary, calibration may be accomplished using an in vitro test strip (or other reference), e.g., a small sample test strip such as a test strip that requires less than about 1 microliter of sample (for example FreeStyle® or Precision® blood glucose monitoring test strips from Abbott Diabetes Care, Alameda, Calif.). For example, test strips that require less than about 1 nanoliter of sample may be used. In certain embodiments, a sensor may be calibrated using only one sample of body fluid per calibration event. For example, a user need only lance a body part one time to obtain a sample for a calibration event (e.g., for a test strip), or may lance more than one time within a short period of time if an insufficient volume of sample is firstly obtained. Embodiments include obtaining and using multiple samples of body fluid for a given calibration event, where glucose values of each sample are substantially similar. Data obtained from a given calibration event may be used independently to calibrate or combined with data obtained from previous calibration events, e.g., averaged including weighted averaged, etc., to calibrate. In certain embodiments, a system need only be calibrated once by a user, where recalibration of the system is not required.

Alternative or additional calibration data may be provided based on tests performed by a health care professional or by the user. For example, it is common for diabetic individuals to determine their own blood glucose concentration using commercially available testing kits. The results of this test is input into the sensor control unit either directly, if an appropriate input device (e.g., a keypad, an optical signal receiver, or a port for connection to a keypad or computer) is incorporated in the sensor control unit, or indirectly by inputting the calibration data into the receiver/display unit and transmitting the calibration data to the sensor control unit.

Other methods of independently determining analyte levels may also be used to obtain calibration data. This type of calibration data may supplant or supplement factory-determined calibration values.

In certain embodiments of the present disclosure, calibration data may be required at periodic intervals, for example, every eight hours, once a day, or once a week, to confirm that accurate analyte levels are being reported. Calibration may also be required each time a new sensor is implanted or if the sensor exceeds a threshold minimum or maximum value or if the rate of change in the sensor signal exceeds a threshold value. In some cases, it may be necessary to wait a period of time after the implantation of the sensor before calibrating to allow the sensor to achieve equilibrium. In certain embodiments, the sensor is calibrated only after it has been inserted. In other embodiments, no calibration of the sensor is needed.

Analyte Monitoring Device

In certain embodiments, the analyte monitoring device includes a sensor control unit and a sensor. In these embodiments, the processing circuit of the sensor control unit is able to determine a level of the analyte and activate an alarm system if the analyte level exceeds a threshold value. The sensor control unit, in these embodiments, has an alarm system and may also include a display, such as an LCD or LED display.

A threshold value is exceeded if the datapoint has a value that is beyond the threshold value in a direction indicating a particular condition. For example, a datapoint which correlates to a glucose level of 200 mg/dL exceeds a threshold value for hyperglycemia of 180 mg/dL, because the datapoint indicates that the user has entered a hyperglycemic state. As another example, a datapoint which correlates to a glucose level of 65 mg/dL exceeds a threshold value for hypoglycemia of 70 mg/dL because the datapoint indicates that the user is hypoglycemic as defined by the threshold value. However, a datapoint which correlates to a glucose level of 75 mg/dL would not exceed the same threshold value of 70 mg/dL for hypoglycemia because the datapoint does not indicate that particular condition as defined by the chosen threshold value.

An alarm may also be activated if the sensor readings indicate a value that is outside of (e.g., above or below) a measurement range of the sensor. For glucose, the physiologically relevant measurement range may be 30-400 mg/dL, including 40-300 mg/dL and 50-250 mg/dL, of glucose in the interstitial fluid.

The alarm system may also, or alternatively, be activated when the rate of change or acceleration of the rate of change in analyte level increase or decrease reaches or exceeds a threshold rate or acceleration. For example, in the case of a subcutaneous glucose monitor, the alarm system may be activated if the rate of change in glucose concentration exceeds a threshold value which may indicate that a hyperglycemic or hypoglycemic condition is likely to occur. In some cases, the alarm system is activated if the acceleration of the rate of change in glucose concentration exceeds a threshold value which may indicate that a hyperglycemic or hypoglycemic condition is likely to occur.

A system may also include system alarms that notify a user of system information such as battery condition, calibration, sensor dislodgment, sensor malfunction, etc. Alarms may be, for example, auditory and/or visual. Other sensory-stimulating alarm systems may be used including alarm systems which heat, cool, vibrate, or produce a mild electrical shock when activated.

Drug Delivery System

The subject matter of the present disclosure also includes sensors used in sensor-based drug delivery systems. The system may provide a drug to counteract the high or low level of the analyte in response to the signals from one or more sensors. Alternatively, the system may monitor the drug concentration to ensure that the drug remains within a desired therapeutic range. The drug delivery system may include one or more (e.g., two or more) sensors, a processing unit such as a transmitter, a receiver/display unit, and a drug administration system. In some cases, some or all components may be integrated in a single unit. A sensor-based drug delivery system may use data from the one or more sensors to provide necessary input for a control algorithm/mechanism to adjust the administration of drugs, e.g., automatically or semi-automatically. As an example, a glucose sensor may be used to control and adjust the administration of insulin from an external or implanted insulin pump.

Each of the various references, presentations, publications, provisional and/or non-provisional U.S. Patent Applications, U.S. Patents, non-U.S. Patent Applications, and/or non-U.S. Patents that have been identified herein, is incorporated herein by reference in its entirety.

Other embodiments and modifications within the scope of the present disclosure will be apparent to those skilled in the relevant art. Various modifications, processes, as well as numerous structures to which the embodiments of the subject matter of the present disclosure may be applicable will be readily apparent to those of skill in the art to which the present disclosure is directed upon review of the specification. Various aspects and features of the present disclosure may have been explained or described in relation to understandings, beliefs, theories, underlying assumptions, and/or working or prophetic examples, although it will be understood that the present disclosure is not bound to any particular understanding, belief, theory, underlying assumption, and/or working or prophetic example. Although various aspects and features of the present disclosure may have been described largely with respect to applications, or more specifically, medical applications, involving diabetic humans, it will be understood that such aspects and features also relate to any of a variety of applications involving non-diabetic humans and any and all other animals. Further, although various aspects and features of the present disclosure may have been described largely with respect to applications involving partially implanted sensors, such as transcutaneous or subcutaneous sensors, it will be understood that such aspects and features also relate to any of a variety of sensors that are suitable for use in connection with the body of an animal or a human, such as those suitable for use as fully implanted in the body of an animal or a human. Finally, although the various aspects and features of the present disclosure have been described with respect to various embodiments and specific examples herein, all of which may be made or carried out conventionally, it will be understood that the present disclosure is entitled to protection within the full scope of the appended claims.

The following examples are put forth so as to provide those of ordinary skill in the art with a complete disclosure and description of how to make and use the embodiments of the present disclosure, and are not intended to limit the scope of what the inventors regard as their invention nor are they intended to represent that the experiments below are all or the only experiments performed. Efforts have been made to ensure accuracy with respect to numbers used (e.g., amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

The temperature sensor may be internal or external to the on-body housing. The temperature sensor may also sit above the skin, or be provided as an electrode running along the analyte sensor to be transcutaneously implanted below the skin. The temperature sensor electrode would then be electrically coupled to a temperature measurement circuit within the on-body housing. The temperature measurements may be transmitted to the blood glucose meter upon request. For manufacturability and cost-effectiveness, particularly when the on-body housing is intended to be disposable, it may be desirable to avoid the inclusion of a temperature sensor and/or control circuitry in the on-body housing. As such, in certain embodiments, there is provided reader (e.g., a blood glucose meter, or other hand-held measurement or analysis instrument) with a temperature measurement sensor and control system. The temperature measurement sensor may be provided on the permanent hand-held instrument to avoid disposing of the temperature measurement components when the on-body housing is disposed.

The concentration of drugs, such as, for example, antibiotics (e.g., gentamicin, vancomycin, and the like), digitoxin, digoxin, drugs of abuse, theophylline, and warfarin, may also be monitored. In those embodiments that monitor more than one analyte, the analytes may be monitored at the same or different times. In certain embodiments, the analyte sensor is a glucose sensor. In another embodiment, the analyte sensor is a ketone sensor Example Embodiments In some aspects of the present disclosure, methods of detecting and/or determining an analyte level by compensating for ambient temperature using a single temperature sensor (e.g., coupled to an in vivo analyte sensor) are provided that include receiving an analyte sensor signal (e.g., analyte sensor information, such as current, voltage, etc.) derived from an in vivo analyte sensor; detecting a temperature measurement from a temperature sensor; determining, with a processor, whether a threshold requirement is exceeded based on the temperature measurement; and determining, with the processor, a temperature-compensated analyte sensor signal. When the threshold requirement is not exceeded, the temperature-compensated analyte sensor signal is determined using the temperature measurement. Only when the threshold requirement is exceeded, the temperature-compensated analyte sensor signal is determined using an ambient-compensated temperature that is derived by compensating the temperature measurement for ambient temperature.

In certain embodiments, the processor is coupled to an on-body unit including the in vivo analyte sensor.

In certain embodiments, the processor is coupled to a receiver that communicates wired or wirelessly with an on-body unit including the in vivo analyte sensor.

In certain embodiments, the temperature measurement is performed by an on-body unit including the in vivo analyte sensor.

In certain embodiments, the temperature measurement is performed by a receiver that communicates wired or wirelessly with an on-body unit including the in vivo analyte sensor.

In certain embodiments, the methods include determining an analyte level based on the temperature-compensated analyte sensor signal.

In certain embodiments, the temperature sensor is coupled to an on-body unit including the in vivo analyte sensor.

In certain embodiments, the temperature measurement represents skin temperature.

In certain embodiments, the ambient-compensated temperature is derived by adding a correction factor to the temperature measurement.

In certain embodiments, the analyte is glucose.

In certain embodiments, the threshold requirement includes an upper threshold value, and adding a correction factor decreases the temperature measurement when the upper threshold value is exceeded.

In certain embodiments, the threshold requirement includes a lower threshold value, and adding a correction factor increases the temperature measurement when the lower threshold value is exceeded.

In certain embodiments, the threshold requirement includes an upper threshold value and a lower threshold value, and adding a correction factor decreases the temperature measurement when the upper threshold value is exceeded and increases the temperature measurement when the lower threshold value is exceeded.

In certain embodiments, the threshold requirement is exceeded when a value of the temperature measurement exceeds the threshold requirement.

In certain embodiments, the threshold requirement is exceeded when a rate-of-change of the temperature measurement exceeds the threshold requirement.

In certain embodiments, the methods include detecting a calibration temperature measured by the temperature sensor when the on-body sensor is coupled to a body of a test subject; and determining, with a processor, a threshold requirement based on the calibration temperature.

In certain embodiments, the threshold requirement includes a predetermined amount of deviation from the calibration temperature.

In certain embodiments, the threshold requirement includes an amount of deviation from the calibration temperature, and the amount of deviation is detected by monitoring changes during a period of time.

In certain embodiments, the calibration temperature is determined based on temperature measurements during a period of time.

In certain embodiments, the threshold requirement is exceeded when a rate-of-change of the temperature measurement exceeds the threshold requirement.

In certain embodiments, the processor determining the threshold requirement is coupled to an on-body unit including the in vivo analyte sensor.

In certain embodiments, the processor determining the threshold requirement is coupled to a receiver that communicates wired or wirelessly with an on-body unit including the in vivo analyte sensor.

In some aspects of the present disclosure, analyte monitoring devices are provided. The analyte monitoring devices include a housing; a processor coupled to the housing; and memory communicably coupled to the processor. An in vivo analyte sensor is communicably coupled to the processor, and a temperature sensor is communicably coupled to the processor. The memory includes instructions stored therein that, when executed by the processor, cause the processor to receive an sensor signal from the in vivo analyte sensor; detecting a temperature measurement from the temperature sensor; determine whether a threshold requirement is exceeded based on the temperature measurement; and determine a temperature-compensated analyte sensor signal. When the threshold requirement is not exceeded, the temperature-compensated analyte sensor signal is determined using the temperature measurement. Only when the threshold requirement is exceeded, the temperature-compensated analyte sensor signal is determined using an ambient-compensated temperature that is derived by compensating the temperature measurement for ambient temperature.

In certain embodiments, the temperature measurement represents skin temperature.

In certain embodiments, the ambient-compensated temperature is derived by adding a correction factor to the temperature measurement.

In certain embodiments, the analyte is glucose.

In certain embodiments, the threshold requirement includes an upper threshold value, and adding a correction factor decreases the temperature measurement when the upper threshold value is exceeded.

In certain embodiments, the threshold requirement includes a lower threshold value, and adding a correction factor increases the temperature measurement when the lower threshold value is exceeded.

In certain embodiments, the threshold requirement includes an upper threshold value and a lower threshold value, and adding a correction factor decreases the temperature measurement when the upper threshold value is exceeded and increases the temperature measurement when the lower threshold value is exceeded.

In certain embodiments, the threshold requirement is exceeded when a value of the temperature measurement exceeds the threshold requirement.

In certain embodiments, the threshold requirement is exceeded when a rate-of-change of the temperature measurement exceeds the threshold requirement.

In certain embodiments, the memory includes instructions that, when executed by the processor, cause the processor to detect a calibration temperature measured by the temperature sensor when the analyte monitoring device is coupled to a body of a test subject; and determine a threshold requirement based on the calibration temperature.

In certain embodiments, the threshold requirement includes a predetermined amount of deviation from the calibration temperature.

In certain embodiments, the threshold requirement includes an amount of deviation from the calibration temperature, and the amount of deviation is detected by monitoring changes during a period of time.

In certain embodiments, the calibration temperature is determined based on temperature measurements during a period of time.

In certain embodiments, the threshold requirement is exceeded when a rate-of-change of the temperature measurement exceeds the threshold requirement.

In certain embodiments, the in vivo analyte sensor is coupled to the housing.

In certain embodiments, the temperature sensor is coupled to the housing.

In certain embodiments, the in vivo analyte sensor is coupled to an on-body unit, and the analyte monitoring device receives wired or wireless communications from the on-body unit.

In certain embodiments, the temperature sensor is coupled to the housing.

In certain embodiments, the memory includes instructions that, when executed by the processor, cause the processor to determine an analyte level based on the temperature-compensated analyte sensor signal.

In certain embodiments, the temperature measurement is performed by an on-body unit including the in vivo analyte sensor and communicated to the analyte monitoring device.

In certain embodiments, the temperature measurement is performed by the analyte monitoring device.

In some aspects of the present disclosure, methods of compensating for ambient temperature using a single temperature sensor are provided. The methods include detecting a temperature measurement from a temperature sensor; and determining, with a processor, an ambient-compensated temperature from the temperature measurement using an offset term.

In certain embodiments, the offset term is based on a predetermined core body temperature.

In certain embodiments, the temperature sensor is coupled to an on-body unit including an in vivo analyte sensor.

In certain embodiments, the temperature sensor protrudes from a skin-contacting surface of the on-body sensor, and the temperature measurement represents skin temperature.

In certain embodiments, the methods include receiving a sensor signal from an in vivo analyte sensor; and determining, with a processor, a temperature-compensated analyte sensor signal with the ambient-compensated temperature.

In certain embodiments, the processor that determines the ambient-compensated temperature is the same processor as the processor that determines the temperature-compensated analyte sensor signal.

In certain embodiments, the processor that determines the ambient-compensated temperature and the processor that determines the temperature-compensated analyte sensor signal are coupled to a receiver that communicates wired or wirelessly with an on-body unit including the in vivo analyte sensor.

In certain embodiments, the processor that determines the ambient-compensated temperature and the processor that determines the temperature-compensated analyte sensor signal are coupled to an on-body unit including the in vivo analyte sensor.

In certain embodiments, the processor that determines the ambient-compensated temperature is coupled to an on-body unit including the in vivo analyte sensor, and the processor that determines the temperature-compensated analyte sensor signal is coupled to a receiver that communicates wired or wirelessly with the on-body unit.

In certain embodiments, the methods include determining an analyte level based on the temperature-compensated analyte sensor signal.

In certain embodiments, the temperature measurement is performed by an on-body unit including the in vivo analyte sensor.

In certain embodiments, the temperature measurement is performed by a receiver that communicates wired or wirelessly with an on-body unit including the in vivo analyte sensor.

In certain embodiments, the temperature sensor is disposed on a printed circuit board of the on-body sensor.

In certain embodiments, the predetermined core body temperature is between 36° C. and 38° C.

In certain embodiments, the predetermined core body temperature is approximately 37° C.

In some aspects of the present disclosure, analyte monitoring devices are provided. The analyte monitoring devices include a housing; a processor coupled to the housing; and memory communicably coupled to the processor. An in vivo analyte sensor is communicably coupled to the processor, and a temperature sensor is communicably coupled to the processor. The memory includes instructions stored therein that, when executed by the processor, cause the processor to detect a temperature measurement from the temperature sensor; and determine an ambient-compensated temperature from the temperature measurement using an offset term.

In certain embodiments, the offset term is based on a predetermined core body temperature.

In certain embodiments, the temperature sensor protrudes from a skin-contacting surface of the housing, and the temperature measurement represents skin temperature.

In certain embodiments, the memory includes instructions that, when executed by the processor, cause the processor to receive a sensor signal from the in vivo analyte sensor; and determine a temperature-compensated analyte sensor signal with the ambient-compensated temperature.

In certain embodiments, the memory includes instructions that, when executed by the processor, cause the processor to determine an analyte level based on the temperature-compensated analyte sensor signal.

In certain embodiments, the in vivo analyte sensor is coupled to the housing.

In certain embodiments, the temperature sensor is coupled to the housing.

In certain embodiments, the in vivo analyte sensor is coupled to an on-body unit, and the analyte monitoring device receives wired or wireless communications from the on-body unit.

In certain embodiments, the temperature sensor is coupled to the housing.

In certain embodiments, the temperature measurement is performed by an on-body unit including the in vivo analyte sensor and communicated to the analyte monitoring device.

In certain embodiments, the temperature measurement is performed by the analyte monitoring device.

In certain embodiments, the temperature sensor is coupled to an on-body unit including the in vivo analyte sensor.

In certain embodiments, the temperature sensor is disposed on a printed circuit board coupled to the housing.

In certain embodiments, the predetermined core body temperature is between 36° C. and 38° C.

In certain embodiments, the predetermined core body temperature is approximately 37° C.

In some aspects of the present disclosure, methods of compensating for ambient temperature using temperature sensors are provided. The methods include sampling at a first sampling rate, with a processor, first temperature measurements from a first temperature sensor on an on-body sensor; determining, with a processor, first ambient-compensated temperatures from the first temperature measurements; and determining, with a processor, final ambient-compensated temperatures by applying a correction gain or factor to the first ambient-compensated temperatures. The correction gain or factor changes value at a slower rate than the sampling rate.

In certain embodiments, the processor sampling first temperatures at a first sampling rate, the processor determining first ambient-compensated temperatures, and the processor determining final ambient compensated temperatures are the same processor.

In certain embodiments, the sampling of first temperatures at a first sampling rate, the determining of first ambient-compensated temperatures, and the determining of final ambient compensated temperatures are performed by an on-body unit including an in vivo analyte sensor.

In certain embodiments, the sampling of first temperatures at a first sampling rate, the determining of first ambient-compensated temperatures, and the determining of final ambient compensated temperatures are performed by a receiver that communicates with an on-body unit including an in vivo analyte sensor.

In certain embodiments, one or more of the processor sampling first temperatures at a first sampling rate, the processor determining first ambient-compensated temperatures, and the processor determining final ambient compensated temperatures are different processors.

In certain embodiments, the sampling of first temperatures at a first sampling rate, the determining of first ambient-compensated temperatures, and the determining of final ambient compensated temperatures are each performed by either a processor coupled to an on-body unit including an in vivo analyte sensor or by a processor coupled to a receiver that communicates with the on-body unit.

In certain embodiments, the correction gain is applied to the first ambient-compensated temperatures.

In certain embodiments, the methods include sampling at the first sampling rate, with a processor, second temperature measurements from a second temperature sensor on the on-body sensor; and determining, with a processor, second ambient-compensated temperatures with the second temperature measurements. The correction gain is calculated by performing a moving average between first ambient-compensated temperatures and second ambient-compensated temperatures, such that the correction gain is based on a set of recent pairs of first ambient-compensated temperatures and second ambient-compensated temperatures.

In certain embodiments, the processor sampling first temperatures at a first sampling rate, the processor determining first ambient-compensated temperatures, the processor determining final ambient compensated temperatures, the processor sampling second temperatures at the first sampling rate, and the processor determining the second ambient-compensated temperature are the same processor.

In certain embodiments, the sampling of first temperatures at a first rate, the determining of first ambient-compensated temperatures, the determining of final ambient compensated temperatures, the determining of final ambient compensated temperatures, the sampling of second temperatures at the first sampling rate, and the determining of the second ambient-compensated temperature are performed an on-body unit including an in vivo analyte sensor.

In certain embodiments, the sampling of first temperatures at a first rate, the determining of first ambient-compensated temperatures, the determining of final ambient compensated temperatures, the determining of final ambient compensated temperatures, the sampling of second temperatures at the first sampling rate, and the determining of the second ambient-compensated temperature are performed by a receiver that communicates with an on-body unit including an in vivo analyte sensor.

In certain embodiments, one or more of the processor sampling first temperatures at a first sampling rate, the processor determining first ambient-compensated temperatures, the processor determining final ambient compensated temperatures, the processor sampling second temperatures at the first sampling rate, and the processor determining the second ambient-compensated temperature are different processors.

In certain embodiments, the sampling of first temperatures at a first rate, the determining of first ambient-compensated temperatures, the determining of final ambient compensated temperatures, the determining of final ambient compensated temperatures, the sampling of second temperatures at the first sampling rate, and the determining of the second ambient-compensated temperature are each performed by either a processor coupled to an on-body unit including an in vivo analyte sensor or by a processor coupled to a receiver that communicates with the on-body unit.

In certain embodiments, the correction gain is calculated using parameter adaptation.

In certain embodiments, the parameter adaptation is MIT adaptation.

In certain embodiments, the correction factor is applied to the first ambient-compensated temperatures.

In certain embodiments, the methods include sampling at the first sampling rate, with a processor, second temperatures measured from a second temperature sensor on the on-body sensor; and determining, with a processor, second ambient-compensated temperatures with the second temperature measurements. The correction factor is calculated by performing windowed comparisons between the first ambient-compensated temperatures and the second ambient-compensated temperatures, such that the correction factor is based on a set of recent pairs of first ambient-compensated temperatures and second ambient-compensated temperatures.

In certain embodiments, the processor sampling first temperatures at a first sampling rate, the processor determining first ambient-compensated temperatures, the processor determining final ambient compensated temperatures, the processor sampling second temperatures at the first sampling rate, and the processor determining the second ambient-compensated temperature are the same processor.

In certain embodiments, the sampling of first temperatures at a first rate, the determining of first ambient-compensated temperatures, the determining of final ambient compensated temperatures, the determining of final ambient compensated temperatures, the sampling of second temperatures at the first sampling rate, and the determining of the second ambient-compensated temperature are performed an on-body unit including an in vivo analyte sensor.

In certain embodiments, the sampling of first temperatures at a first rate, the determining of first ambient-compensated temperatures, the determining of final ambient compensated temperatures, the determining of final ambient compensated temperatures, the sampling of second temperatures at the first sampling rate, and the determining of the second ambient-compensated temperature are performed by a receiver that communicates with an on-body unit including an in vivo analyte sensor.

In certain embodiments, one or more of the processor sampling first temperatures at a first sampling rate, the processor determining first ambient-compensated temperatures, the processor determining final ambient compensated temperatures, the processor sampling second temperatures at the first sampling rate, and the processor determining the second ambient-compensated temperature are different processors.

In certain embodiments, the sampling of first temperatures at a first rate, the determining of first ambient-compensated temperatures, the determining of final ambient compensated temperatures, the determining of final ambient compensated temperatures, the sampling of second temperatures at the first sampling rate, and the determining of the second ambient-compensated temperature are each performed by either a processor coupled to an on-body unit including an in vivo analyte sensor or by a processor coupled to a receiver that communicates with the on-body unit.

In some aspects of the present disclosure analyte monitoring device are provided. The analyte monitoring device include a housing; a processor coupled to the housing; and memory communicably coupled to the processor. An in vivo analyte sensor is communicably coupled to the processor, and a first temperature sensor and second temperature sensor are communicably coupled to the processor. The memory includes instructions stored therein that, when executed by the processor, cause the processor to sample at a first sampling rate, with a processor, first temperatures measured from a first temperature sensor on the housing; determine first ambient-compensated temperatures from the first temperature measurements; and determine final ambient-compensated temperatures by applying a correction gain or factor to the first ambient-compensated temperatures. The correction gain or factor changes value at a slower rate than the sampling rate.

In certain embodiments, the in vivo analyte sensor is coupled to the housing.

In certain embodiments, the first temperature sensor and/or second temperature sensor is coupled to the housing.

In certain embodiments, the in vivo analyte sensor is coupled to an on-body unit, and the analyte monitoring device receives wired or wireless communications from the on-body unit.

In certain embodiments, the first temperature sensor and/or second temperature sensor is coupled to the housing.

In certain embodiments, the first temperature measurement and/or second temperature measurement is performed by an on-body unit including the in vivo analyte sensor and communicated to the analyte monitoring device.

In certain embodiments, the first temperature measurement and/or second temperature measurement is performed by the analyte monitoring device.

In certain embodiments, the correction gain is applied to the first ambient-compensated temperatures.

In certain embodiments, the memory includes instructions that, when executed by the processor, cause the processor to sample at the first sampling rate second temperatures measured from a second temperature sensor on the housing; and determine second ambient-compensated temperatures with the second temperature measurements. The correction gain is calculated by performing a moving average between first ambient-compensated temperatures and second ambient-compensated temperatures, such that the correction gain is based on a set of recent pairs of first ambient-compensated temperatures and second ambient-compensated temperatures.

In certain embodiments, the in vivo analyte sensor is coupled to the housing.

In certain embodiments, the first temperature sensor and/or second temperature sensor is coupled to the housing.

In certain embodiments, the in vivo analyte sensor is coupled to an on-body unit, and the analyte monitoring device receives wired or wireless communications from the on-body unit.

In certain embodiments, the first temperature sensor and/or second temperature sensor is coupled to the housing.

In certain embodiments, the first temperature measurement and/or second temperature measurement is performed by an on-body unit including the in vivo analyte sensor and communicated to the analyte monitoring device.

In certain embodiments, the first temperature measurement and/or the second temperature measurement is performed by the analyte monitoring device.

In certain embodiments, the correction gain is calculated using parameter adaptation.

In certain embodiments, the correction gain is calculated using MIT adaptation.

In certain embodiments, the correction factor is applied to the first ambient-compensated temperatures.

In certain embodiments, the memory includes instructions that, when executed by the processor, cause the processor to sample at the first sampling rate second temperatures measured from a second temperature sensor on the housing; and determine second ambient-compensated temperatures with the second temperature measurements. The correction factor is calculated by performing windowed comparisons between the first ambient-compensated temperatures and the second ambient-compensated temperatures, such that the correction factor is based on a set of recent pairs of first ambient-compensated temperatures and second ambient-compensated temperatures.

In certain embodiments, the first temperature sensor is disposed at a skin-contacting surface of the housing and the second temperature sensor is disposed on a printed circuit board coupled to the housing.

In certain embodiments, the memory includes instructions that, when executed by the processor, cause the processor to receive a sensor signal from the in vivo analyte sensor; and determine a temperature-compensated analyte sensor signal with the ambient-compensated temperature.

In certain embodiments, the memory includes instructions that, when executed by the processor, cause the processor to determine, with the processor, an analyte level based on the temperature-compensated analyte sensor signal.

In certain embodiments, the in vivo analyte sensor is coupled to the housing.

In certain embodiments, the first temperature sensor and/or second temperature sensor is coupled to the housing.

In certain embodiments, the in vivo analyte sensor is coupled to an on-body unit, and the analyte monitoring device receives wired or wireless communications from the on-body unit.

In certain embodiments, the first temperature sensor is disposed at a skin-contacting surface of the housing and the second temperature sensor is disposed on a printed circuit board on the housing.

In some aspects of the present disclosure, in vivo analyte sensors are provided. The in vivo analyte sensors include a substrate layer; an electrode layer disposed on the substrate layer; and a temperature sensing element disposed on the substrate layer, the temperature sensing element providing a signal for determining temperature adjacent the sensing area. The electrode layer includes a sensing area, In certain embodiments, the temperature sensing element is a thermistor.

In certain embodiments, the temperature sensing element is a resistance temperature detector (RTD).

In certain embodiments, the electrode layer includes a plurality of electrodes, and one electrode of the plurality of electrodes is the temperature sensing element.

In certain embodiments, the plurality of electrodes includes a working electrode, reference, electrode, and a counter electrode, and the temperature sensing element is the counter electrode and includes two contact points for electric coupling to a current providing circuit.

In certain embodiments, the temperature sensing element extends back and forth a plurality of times.

In certain embodiments, the temperature sensing element includes two traces of dissimilar metals that join at a junction adjacent the sensing area.

In certain embodiments, the two dissimilar metals are gold, silver, carbon, titanium, or an alloy thereof.

In certain embodiments, the two traces are on a same side of the substrate layer as the electrode layer.

In certain embodiments, the two traces are on an opposite side of the substrate layer as the electrode layer.

In certain embodiments, the junction is directly opposite the sensing area.

In certain embodiments, each of the two traces are on a different side of the substrate layer from one another, and a through-hole is used to join the two traces.

In certain embodiments, the two traces are conductive ink.

In certain embodiments, the temperature sensing element is a pyro-electric sensor.

In certain embodiments, the temperature sensing element is a semiconductor sensor.

In certain embodiments, the temperature sensing element includes a second sensing area and a analyte reservoir, the analyte reservoir includes a known volume of analyte at a known concentration.

In certain embodiments, the secondary sensing area is isolated and the reservoir lasts for the life of the sensor.

In certain embodiments, the analyte sensors include a membrane between the second sensing area and the reservoir.

In certain embodiments, the analyte sensors include a temporary barrier between the second sensing area and the reservoir that ceases to separate the second sensing area and the reservoir when the analyte sensor is positioned in vivo.

In some aspects of the present disclosure, analyte monitoring devices are provided that include a housing; electronic circuitry coupled to the housing, the electronic circuitry including a processor; and an in vivo analyte sensor electrically coupled to the electronic circuitry and extending from the housing. The in vivo analyte sensor include a substrate layer; an electrode layer disposed on the substrate layer; and a temperature sensing element disposed on the substrate layer, the temperature sensing element providing a signal for determining temperature adjacent a sensing area.

In certain embodiments, the temperature sensing element is a thermistor.

In certain embodiments, the temperature sensing element is a resistance temperature detector (RTD).

In certain embodiments, the electrode layer includes a plurality of electrodes, and one electrode of the plurality of electrodes is the temperature sensing element.

In certain embodiments, the plurality of electrodes includes a working electrode, reference, electrode, and a counter electrode, and the temperature sensing element is the counter electrode and includes two electrical contacts for electric coupling to a current providing circuit.

In certain embodiments, the temperature sensing element extends back and forth a plurality of times.

In certain embodiments, the electronic circuitry includes a working electrode contact that electrically couple to the working electrode, a reference electrode contact that electrically couple to the reference electrode, and two counter electrode contacts that electrically couple to the two electrical contacts of the temperature sensing element and supply the temperature sensing element with current.

In certain embodiments, the electronic circuitry includes two electrode contacts that electrically couple to two electrical contacts of the temperature sensing element and supply the temperature sensing element with current.

In certain embodiments, the temperature sensing element includes two traces of dissimilar metals that join at a junction adjacent the sensing area.

In certain embodiments, the two dissimilar metals are gold, silver, carbon, titanium, or an alloy thereof.

In certain embodiments, the two traces are on a same side of the substrate layer as the electrode layer.

In certain embodiments, the two traces are on an opposite side of the substrate layer as the electrode layer.

In certain embodiments, the junction is directly opposite the sensing area.

In certain embodiments, each of the two traces are on a different side of the substrate layer from one another, and a through-hole is used to join the two traces.

In certain embodiments, the two traces are conductive ink.

In certain embodiments, the temperature sensing element is a pyro-electric sensor.

In certain embodiments, the temperature sensing element is a semiconductor sensor.

In certain embodiments, the temperature sensing element includes a second sensing area and a analyte reservoir, the analyte reservoir includes a known volume of analyte at a known concentration.

In certain embodiments, the secondary sensing area is isolated and the reservoir lasts for the life of the analyte sensor.

In certain embodiments, the analyte sensors include a membrane between the second sensing area and the reservoir.

In certain embodiments, the analyte sensors include a temporary barrier between the second sensing area and the reservoir that ceases to separate the second sensing area and the reservoir when the analyte sensor is positioned in vivo.

In some aspects of the present disclosure, analyte sensor devices are provided that include a body including an elongated member having a central tunnel that inserts into skin of a subject; electrodes disposed on the body; and a temperature sensor coupled to the body. The body is adapted to couple to the skin of the subject.

In certain embodiments, the temperature sensor is disposed within the central tunnel and adapted to pierce the skin of the patient, and the electrodes disposed on the outside of the body.

In certain embodiments, the temperature sensor is softened by exposure to body fluids.

In certain embodiments, the central tunnel is for insulin delivery.

In certain embodiments, the electrodes include wires disposed on the body, and the temperature sensor includes a thermocouple wire disposed on the body.

In certain embodiments, the analyte sensor device includes a housing adapted to couple to an insulin delivery tube and insulin pump; and electronic circuitry coupled to the housing, the electronic circuitry including a processor for determining analyte levels.

In some aspects of the present disclosure, methods are provided that include coupling an analyte sensor device to a skin of a subject and inserting a temperature sensor within the skin of the subject. The temperature sensor is disposed within the central tunnel. The sensor coupling device includes a body including an elongated member having a central tunnel that inserts into the skin of a subject, and electrodes disposed on the body. The body is adapted to couple to the skin of the subject.

In certain embodiments, before the temperature sensor is inserted within the skin of the subject, the methods include piercing the skin of the subject with a needle disposed within the central tunnel; removing the needle from the central tunnel; and inserting the temperature sensor within the central tunnel.

In certain embodiments, the methods include determining an analyte level based on a sensor signal from the electrodes that has been compensated for temperature from the temperature sensor.

In certain embodiments, the temperature sensor is adapted to pierce the skin of the subject.

In certain embodiments, the temperature sensor is softened by exposure to body fluids.

In some aspects of the present disclosure, methods are provided that include receiving a first sensor signal from a first electrode on an in vivo analyte sensor on an on-body sensor; receiving a second sensor signal from a second electrode on the in vivo analyte sensor, and determining, with a processor, a compensated temperature at the two working electrodes based on the difference between the temperature dependencies for the different sensing chemistries on the two working electrodes. The first electrode and second electrode include different sensing chemistries with different temperature dependencies.

In certain embodiments, the temperature is determined based on a ratio of the first sensor signal and the second sensor signal.

In certain embodiments, the temperature is determined based on a predetermined temperature, sensor areas, quantity of sensing materials, and efficiencies of the sensing chemistries, and diffusion controlling membrane.

In certain embodiments, the methods include determining, with a processor, a temperature-compensated analyte sensor signal with the compensated temperature.

In certain embodiments, the processor that determines the compensated temperature is the same processor as the processor that determines the temperature-compensated analyte sensor signal.

In certain embodiments, the processor that determines the compensated temperature and the processor that determines the temperature-compensated analyte sensor signal are coupled to a receiver that communicates wired or wirelessly with an on-body unit including the in vivo analyte sensor.

In certain embodiments, the processor that determines the compensated temperature and the processor that determines the temperature-compensated analyte sensor signal are coupled to an on-body unit including the in vivo analyte sensor.

In certain embodiments, the processor that determines the compensated temperature is coupled to an on-body unit including the in vivo analyte sensor, and the processor that determines the temperature-compensated analyte sensor signal is coupled to a receiver that communicates wired or wirelessly with the on-body unit.

In certain embodiments, the methods include determining an analyte level based on the temperature-compensated analyte sensor signal.

In certain embodiments, the temperature-compensated analyte sensor signal is determined with the first sensor signal and not the second sensor signal.

In certain embodiments, the temperature-compensated analyte sensor signal is determined with the second sensor signal and not the first sensor signal.

In certain embodiments, the temperature-compensated analyte sensor signal is determined with both the first sensor signal and the second sensor signal.

In certain embodiments, the first electrode includes a first plurality of sensing elements on the in vivo analyte sensor and the second electrode includes a second plurality of sensing elements disposed on the in vivo analyte sensor.

In some aspects of the present disclosure, analyte monitoring devices are provided that include a housing; a processor coupled to the housing; and memory communicably coupled to the processor. An in vivo analyte sensor is communicably coupled to the processor, and the in vivo analyte sensor includes two working electrodes. The memory includes instructions stored therein that, when executed by the processor, cause the processor to detect a first sensor signal from a first electrode on the in vivo analyte sensor; detect a second sensor signal from a second electrode on the in vivo analyte sensor; and determine a compensated temperature at the two working electrodes based on the difference between the temperature dependencies for the different sensing chemistries on the two working electrodes. The first electrode and second electrode include different sensing chemistries with different temperature dependencies.

In certain embodiments, the in vivo analyte sensor is coupled to the housing.

In certain embodiments, the compensated temperature is determined by the analyte monitoring device.

In certain embodiments, the in vivo analyte sensor is coupled to an on-body unit, and the analyte monitoring device receives wired or wireless communications from the on-body unit.

In certain embodiments, the memory includes instructions that, when executed by the processor, cause the processor to determine an analyte level based on the temperature-compensated analyte sensor signal.

In certain embodiments, the compensated temperature is determined by an on-body unit including the in vivo analyte sensor and communicated to the analyte monitoring device.

In certain embodiments, the temperature is determined based on a ratio of the first sensor signal and the second sensor signal.

In certain embodiments, the temperature is determined based on a predetermined temperature, sensor areas, quantity of sensing materials, and efficiencies of the sensing chemistries, and diffusion controlling membrane.

In certain embodiments, the memory includes instructions stored therein that, when executed by the processor, cause the processor to determining a temperature-compensated analyte sensor signal with the compensated temperature.

In certain embodiments, the in vivo analyte sensor is coupled to the housing.

In certain embodiments, the compensated temperature is determined by the analyte monitoring device.

In certain embodiments, the in vivo analyte sensor is coupled to an on-body unit, and the analyte monitoring device receives wired or wireless communications from the on-body unit.

In certain embodiments, the memory includes instructions that, when executed by the processor, cause the processor to determine an analyte level based on the temperature-compensated analyte sensor signal.

In certain embodiments, the compensated temperature is determined by an on-body unit including the in vivo analyte sensor and communicated to the analyte monitoring device.

In certain embodiments, the temperature-compensated analyte sensor signal is determined with the first sensor signal and not the second sensor signal.

In certain embodiments, the temperature-compensated analyte sensor signal is determined with the second sensor signal and not the first sensor signal.

In certain embodiments, the temperature-compensated analyte sensor signal is determined with both the first sensor signal and the second sensor signal.

In certain embodiments, the first electrode includes a first plurality of sensing elements on the in vivo analyte sensor and the second electrode includes a second plurality of sensing elements disposed on the in vivo analyte sensor.

In some aspects of the present disclosure, analyte monitoring systems are provided that include an on-body unit and receiver. The on-body includes a first processor and first memory communicably coupled to the first processor; an in vivo analyte sensor communicably coupled to the first processor; and a temperature sensor communicably coupled to the first processor. The receiver is configured to communicate with the on-body unit and includes a second processor and second memory communicably coupled to the second processor. At least one of the first and second memory includes instructions stored therein that, when executed by at least one of the first and second processors, cause the at least one first and second processors to receive a sensor signal from the in vivo analyte sensor; detect a temperature measurement from the temperature sensor; determine whether a threshold requirement is exceeded based on the temperature measurement; and determine a temperature-compensated analyte sensor signal. When the threshold requirement is not exceeded, the temperature-compensated analyte sensor signal is determined using the temperature measurement. Only when the threshold requirement is exceeded, the temperature-compensated analyte sensor signal is determined using an ambient-compensated temperature that is derived by compensating the temperature measurement for ambient temperature.

It should be appreciated that the steps may be performed in various combinations by the processor on the on-body unit and the receiver in communication with the on-body unit in different embodiments. For example, in certain embodiments, the temperature sensor is coupled to the on-body unit and a processor on the on-body unit is detecting the temperature measurement, determining whether the threshold requirement is met, performing the ambient temperature compensation, and determining the temperature-compensated signal. Then, for example, the temperature-compensated signal is sent to a receiver wherein the temperature-compensated analyte level is displayed on a user-interface of the receiver for instance. In another embodiment, for example, the temperature sensor is coupled to the on-body unit and a processor on the on-body unit transmits the temperature measurements to the receiver where a processor coupled to the receiver determines whether the threshold requirement is met, performs the ambient temperature compensation, and determines the temperature-compensated signal. Then, for example, the temperature-compensated analyte level is displayed on a user-interface of the receiver for instance. It should be appreciated that the steps may be split up in other combinations between the on-body unit and the receiver.

In certain embodiments, the temperature measurement represents skin temperature.

In certain embodiments, the ambient-compensated temperature is derived by adding a correction factor to the temperature measurement.

In certain embodiments, the analyte is glucose.

In certain embodiments, the threshold requirement includes an upper threshold value, and wherein adding a correction factor decreases the temperature measurement when the upper threshold value is exceeded.

In certain embodiments, the threshold requirement includes a lower threshold value, and wherein adding a correction factor increases the temperature measurement when the lower threshold value is exceeded.

In certain embodiments, the threshold requirement includes an upper threshold value and a lower threshold value, and wherein adding a correction factor decreases the temperature measurement when the upper threshold value is exceeded and increases the temperature measurement when the lower threshold value is exceeded.

In certain embodiments, the threshold requirement is exceeded when a value of the temperature measurement exceeds the threshold requirement.

In certain embodiments, the threshold requirement is exceeded when a rate-of-change of the temperature measurement exceeds the threshold requirement.

In certain embodiments, the at least one memory includes instructions that, when executed by the at least one first and second processor, cause the at least one first and second processor to detect a calibration temperature measured by the temperature sensor when the on-body unit is coupled to a body of a test subject; and determine a threshold requirement based on the calibration temperature.

In certain embodiments, the threshold requirement includes a predetermined amount of deviation from the calibration temperature.

In certain embodiments, the threshold requirement includes an amount of deviation from the calibration temperature, and wherein the amount of deviation is detected by monitoring changes during a period of time.

In certain embodiments, the calibration temperature is determined based on temperature measurements during a period of time.

In certain embodiments, the threshold requirement is exceeded when a rate-of-change of the temperature measurement exceeds the threshold requirement.

In certain embodiments, the at least one memory includes instructions that, when executed by the at least one first and second processor, cause the at least one first and second processor to determine an analyte level based on the temperature-compensated analyte sensor signal.

In certain embodiments, the temperature measurement is performed by the on-body unit and communicated to the receiver.

In certain embodiments, the temperature measurement is performed by the receiver.

In some aspects of the present disclosure, analyte monitoring systems are provided that include an on-body unit and receiver. The on-body includes a first processor and first memory communicably coupled to the first processor; an in vivo analyte sensor communicably coupled to the first processor; and a temperature sensor communicably coupled to the first processor. The receiver is configured to communicate with the on-body unit and includes a second processor and second memory communicably coupled to the second processor. At least one of the first and second memory includes instructions stored therein that, when executed by at least one of the first and second processors, cause the at least one first and second processors to detect a temperature measurement from the temperature sensor; and determine an ambient-compensated temperature from the temperature measurement using an offset term.

It should be appreciated that the steps may be performed in various combinations by the processor on the on-body unit and the receiver in communication with the on-body unit in different embodiments. For example, in certain embodiments, the temperature sensor is coupled to the on-body unit and a processor on the on-body unit detects the temperature measurement, determines an ambient-compensated temperature from the measured temperature using an offset term, and determines the temperature-compensated signal. Then, for example, the temperature-compensated signal is sent to a receiver wherein the temperature-compensated analyte level is displayed on a user-interface of the receiver for instance. In another embodiment, for example, the temperature sensor is coupled to the on-body unit and a processor on the on-body unit transmits the temperature measurements to the receiver where a processor coupled to the receiver determines an ambient-compensated temperature from the measured temperature using an offset term, and determines the temperature-compensated signal. Then, for example, the temperature-compensated analyte level is displayed on a user-interface of the receiver for instance. It should be appreciated that in other embodiments, the steps may be split up in other combinations between the on-body unit and the receiver.

In certain embodiments, the temperature sensor protrudes from a skin-contacting surface of the on-body unit, and wherein the temperature measurement represents skin temperature.

In certain embodiments, the at least one memory includes instructions that, when executed by the at least one first and second processor, cause the at least one first and second processor to receive a sensor signal from the in vivo analyte sensor; and determine a temperature-compensated analyte sensor signal with the ambient-compensated temperature.

In certain embodiments, the at least one memory includes instructions that, when executed by the at least one first and second processor, cause the at least one first and second processor to determine an analyte level based on the temperature-compensated analyte sensor signal.

In certain embodiments, the temperature measurement is performed by an on-body unit and communicated to the receiver.

In certain embodiments, the offset term that is based on a predetermined core body temperature.

In certain embodiments, the temperature sensor is disposed on a printed circuit board coupled to the on-body unit.

In certain embodiments, the offset term that is based on a predetermined core body temperature, and wherein the predetermined core body temperature is between 36° C. and 38° C.

In certain embodiments, the offset term that is based on a predetermined core body temperature, and wherein the predetermined core body temperature is approximately 37° C.

In some aspects of the present disclosure, analyte monitoring systems are provided that include an on-body unit and receiver. The on-body includes a first processor and first memory communicably coupled to the first processor; an in vivo analyte sensor communicably coupled to the first processor; and a first temperature sensor and second temperature sensor communicably coupled to the first processor. The receiver is configured to communicate with the on-body unit and includes a second processor and second memory communicably coupled to the second processor. At least one of the first and second memory includes instructions stored therein that, when executed by at least one of the first and second processors, cause the at least one first and second processors to sample, at a first sampling rate, first temperatures measured from a first temperature sensor; determine first ambient-compensated temperatures from the first temperature measurements; and determine final ambient-compensated temperatures by applying a correction gain or factor to the first ambient-compensated temperatures. The correction gain or factor changes value at a slower rate than the sampling rate.

It should be appreciated that the steps may be performed in various combinations by the processor on the on-body unit and the receiver in communication with the on-body unit in different embodiments. For example, in certain embodiments, the temperature sensors are coupled to the on-body unit and a processor on the on-body unit samples the temperatures sensors, determines the ambient-compensated temperature from the one-temperature sensor model and two-temperature sensor model, determines the correction factor or gain, determines the final ambient-compensated temperatures. The processor on the on-body unit may then, for example, either determine the temperature-compensated signal, or transmit the final ambient-compensated signal to a receiver having a processor that determines the temperature compensated signal and presents the corresponding analyte level on a user interface. It should be appreciated that the steps may be split up in other combinations between the on-body unit and the receiver in other embodiments. For example, in other embodiments, one or more of the steps in determining the ambient-compensated signal and/or final ambient compensated signal may be performed by the receiver.

In certain embodiments, the first temperature measurement and/or second temperature measurement is performed by the on-body unit and communicated to the receiver.

In certain embodiments, the first temperature measurement and/or second temperature measurement is performed by the receiver.

In certain embodiments, the correction gain is applied to the first ambient-compensated temperatures.

In certain embodiments, the at least one memory includes instructions that, when executed by the at least one first and second processor, cause the at least one first and second processor to sample at the first sampling rate second temperatures measured from a second temperature sensor; and determine second ambient-compensated temperatures with the second temperature measurements. The correction gain is calculated by performing a moving average between first ambient-compensated temperatures and second ambient-compensated temperatures, such that the correction gain is based on a set of recent pairs of first ambient-compensated temperatures and second ambient-compensated temperatures.

In certain embodiments, the first temperature measurement and/or second temperature measurement is performed by the on-body unit and communicated to the receiver.

In certain embodiments, the first temperature measurement and/or the second temperature measurement is performed by the receiver.

In certain embodiments, the correction gain is calculated using parameter adaptation.

In certain embodiments, the correction gain is calculated using MIT adaptation.

In certain embodiments, the correction factor is applied to the first ambient-compensated temperatures.

In certain embodiments, the at least one memory includes instructions that, when executed by the at least one first and second processor, cause the at least one first and second processor to sample at the first sampling rate second temperatures measured from a second temperature sensor; and determine second ambient-compensated temperatures with the second temperature measurements. The correction factor is calculated by performing windowed comparisons between the first ambient-compensated temperatures and the second ambient-compensated temperatures, such that the correction factor is based on a set of recent pairs of first ambient-compensated temperatures and second ambient-compensated temperatures.

In certain embodiments, the first temperature sensor is disposed at a skin-contacting surface of the on-body unit and the second temperature sensor is disposed on a printed circuit board of the on-body unit.

In certain embodiments, the at least one memory includes instructions that, when executed by the at least one first and second processor, cause the at least one first and second processor to receive a sensor signal from the in vivo analyte sensor; and determine a temperature-compensated analyte sensor signal with the ambient-compensated temperature.

In certain embodiments, the at least one memory includes instructions that, when executed by the at least one first and second processor, cause the at least one first and second processor to determine, with the processor, an analyte level based on the temperature-compensated analyte sensor signal.

In certain embodiments, the first temperature sensor is disposed at a skin-contacting surface of the on-body unit and the second temperature sensor is disposed on a printed circuit board of the on-body unit.

In some aspects of the present disclosure, analyte monitoring system are provided that include an on-body unit and receiver. The on-body includes a first processor and first memory communicably coupled to the first processor; and an in vivo analyte sensor communicably coupled to the first processor. The in vivo analyte sensor includes two working electrodes. The receiver is configured to communicate with the on-body unit and includes a second processor and second memory communicably coupled to the second processor. At least one of the first and second memory includes instructions stored therein that, when executed by at least one of the first and second processors, cause the at least one first and second processors to detect a first sensor signal from a first electrode on the in vivo analyte sensor; detect a second sensor signal from a second electrode on the in vivo analyte sensor; and determine a compensated temperature at the two working electrodes based on the difference between the temperature dependencies for the different sensing chemistries on the two working electrodes. The first electrode and second electrode include different sensing chemistries with different temperature dependencies.

It should be appreciated that the steps may be performed in various combinations by the processor on the on-body unit and the receiver in communication with the on-body unit in different embodiments. For example, in certain embodiments, the processor on the on-body unit detects the first sensor signal from the first electrode on the in vivo analyte sensor; detects the second sensor signal from a second electrode on the in vivo analyte sensor; and determines the compensated temperature at the two working electrodes based on the difference between the temperature dependencies for the different sensing chemistries on the two working electrodes. As another example, in certain embodiments, the processor on the on-body unit detects the first sensor signal from the first electrode on the in vivo analyte sensor and detects the second sensor signal from a second electrode on the in vivo analyte sensor. The first sensor signal and the second sensor signal are transmitted to the receiver. The receiver receives the first sensor signal and the second sensor signal. After the detecting the first sensor signal and the second sensor signal, the processor on the receiver determines the compensated temperature at the two working electrodes based on the difference between the temperature dependencies for the different sensing chemistries on the two working electrodes.

In certain embodiments, the compensated temperature is determined by the on-body unit.

In certain embodiments, the at least one memory includes instructions that, when executed by the at least one first and second processor, cause the at least one first and second processor to determine an analyte level based on the temperature-compensated analyte sensor signal.

In certain embodiments, the compensated temperature is determined by the on-body unit and communicated to the receiver.

In certain embodiments, the temperature is determined based on a ratio of the first sensor signal and the second sensor signal, In certain embodiments, the temperature is determined based on a predetermined temperature, sensor areas, quantity of sensing materials, and efficiencies of the sensing chemistries, and diffusion controlling membrane.

In certain embodiments, the at least one memory includes instructions that, when executed by the at least one first and second processor, cause the at least one first and second processor to determining a temperature-compensated analyte sensor signal with the compensated temperature.

In certain embodiments, the at least one memory includes instructions that, when executed by the at least one first and second processor, cause the at least one first and second processor to determine an analyte level based on the temperature-compensated analyte sensor signal.

In certain embodiments, the compensated temperature is determined by the on-body unit and communicated to the receiver.

In certain embodiments, the temperature-compensated analyte sensor signal is determined with the first sensor signal and not the second sensor signal.

In certain embodiments, the temperature-compensated analyte sensor signal is determined with the second sensor signal and not the first sensor signal.

In certain embodiments, the temperature-compensated analyte sensor signal is determined with both the first sensor signal and the second sensor signal.

In certain embodiments, the first electrode includes a first plurality of sensing elements on the in vivo analyte sensor and the second electrode includes a second plurality of sensing elements disposed on the in vivo analyte sensor.

In some aspects of the present disclosure, computer systems are provided that include a processor; and memory communicably coupled to the first processor. The memory includes instructions stored therein that, when executed by the processor, cause the processor to receive analyte data (e.g., a sensor signal from an in vivo analyte sensor); receive temperature data (e.g., a temperature measurement from a temperature sensor); determine whether a threshold requirement is exceeded based on the temperature measurement; and determine a temperature-compensated analyte sensor signal. When the threshold requirement is not exceeded, the temperature-compensated analyte sensor signal is determined using the temperature measurement. Only when the threshold requirement is exceeded, the temperature-compensated analyte sensor signal is determined using an ambient-compensated temperature that is derived by compensating the temperature measurement for ambient temperature.

In certain embodiments, the computer systems include an in vivo analyte sensor, at least one temperature sensor, a sensor electronics unit that receives analyte data from the in vivo analyte sensor, and a receiver unit that receives analyte data from the sensor electronics unit.

In certain embodiments, the temperature measurement represents skin temperature.

In certain embodiments, the ambient-compensated temperature is derived by adding a correction factor to the temperature measurement.

In certain embodiments, the analyte is glucose.

In certain embodiments, the threshold requirement includes an upper threshold value, and wherein adding a correction factor decreases the temperature measurement when the upper threshold value is exceeded.

In certain embodiments, the threshold requirement includes a lower threshold value, and wherein adding a correction factor increases the temperature measurement when the lower threshold value is exceeded.

In certain embodiments, the threshold requirement includes an upper threshold value and a lower threshold value, and wherein adding a correction factor decreases the temperature measurement when the upper threshold value is exceeded and increases the temperature measurement when the lower threshold value is exceeded.

In certain embodiments, the threshold requirement is exceeded when a value of the temperature measurement exceeds the threshold requirement.

In certain embodiments, the threshold requirement is exceeded when a rate-of-change of the temperature measurement exceeds the threshold requirement.

In certain embodiments, the memory includes instructions that, when executed by the processor, cause the processor to detect a calibration temperature measured by the temperature sensor when an on-body unit including the in vivo analyte sensor is coupled to a body of a test subject; and determine a threshold requirement based on the calibration temperature.

In certain embodiments, the threshold requirement includes a predetermined amount of deviation from the calibration temperature.

In certain embodiments, the threshold requirement includes an amount of deviation from the calibration temperature, and wherein the amount of deviation is detected by monitoring changes during a period of time.

In certain embodiments, the calibration temperature is determined based on temperature measurements during a period of time.

In certain embodiments, the threshold requirement is exceeded when a rate-of-change of the temperature measurement exceeds the threshold requirement.

In certain embodiments, the memory includes instructions that, when executed by the processor, cause the processor to determine an analyte level based on the temperature-compensated analyte sensor signal.

In certain embodiments, the temperature measurement is performed by an on-body unit and communicated to a receiver.

In certain embodiments, the temperature measurement is performed by a receiver.

In some aspects of the present disclosure, computer systems are provided that include a processor; and memory communicably coupled to the first processor. The memory includes instructions stored therein that, when executed by the processor, cause the processor to receive temperature data (e.g., a temperature measurement from a temperature sensor); and determine an ambient-compensated temperature from the temperature measurement using an offset term.

In certain embodiments, the computer systems include an in vivo analyte sensor, at least one temperature sensor, a sensor electronics unit that receives analyte data from the in vivo analyte sensor, and a receiver unit that receives analyte data from the sensor electronics unit.

In certain embodiments, the temperature sensor protrudes from a skin-contacting surface of an on-body unit, and wherein the temperature measurement represents skin temperature.

In certain embodiments, the memory includes instructions that, when executed by the processor, cause the processor to receive analyte data (e.g., a sensor signal from the in vivo analyte sensor); and determine a temperature-compensated analyte sensor signal with the ambient-compensated temperature.

In certain embodiments, the memory includes instructions that, when executed by the processor, cause the processor to determine an analyte level based on the temperature-compensated analyte sensor signal.

In certain embodiments, the temperature measurement is performed by an on-body unit and communicated to a receiver.

In certain embodiments, the offset term that is based on a predetermined core body temperature.

In certain embodiments, the temperature sensor is disposed on a printed circuit board coupled to an on-body unit.

In certain embodiments, the offset term that is based on a predetermined core body temperature, and wherein the predetermined core body temperature is between 36° C. and 38° C.

In certain embodiments, the offset term that is based on a predetermined core body temperature, and wherein the predetermined core body temperature is approximately 37° C.

In some aspects of the present disclosure, computer systems are provided that include a processor; and memory communicably coupled to the first processor. The memory includes instructions stored therein that, when executed by the processor, cause the processor to (receive temperature data (e.g., sample, at a first sampling rate, first temperatures measured from a first temperature sensor); determine first ambient-compensated temperatures from the first temperature measurements; and determine final ambient-compensated temperatures by applying a correction gain or factor to the first ambient-compensated temperatures. The correction gain or factor changes value at a slower rate than the sampling rate.

In certain embodiments, the computer systems include an in vivo analyte sensor, at least one temperature sensor, a sensor electronics unit that receives analyte data from the in vivo analyte sensor, and a receiver unit that receives analyte data from the sensor electronics unit.

In certain embodiments, the first temperature measurement and/or a second temperature measurement is performed by the on-body unit and communicated to the receiver.

In certain embodiments, the first temperature measurement and/or a second temperature measurement is performed by the receiver.

In certain embodiments, the correction gain is applied to the first ambient-compensated temperatures.

In certain embodiments, the memory includes instructions that, when executed by the processor, cause the processor to sample, at the first sampling rate, additional temperature data (e.g., second temperatures measured from a second temperature sensor); and determine second ambient-compensated temperatures with the second temperature measurements. The correction gain is calculated by performing a moving average between first ambient-compensated temperatures and second ambient-compensated temperatures, such that the correction gain is based on a set of recent pairs of first ambient-compensated temperatures and second ambient-compensated temperatures.

In certain embodiments, the first temperature measurement and/or second temperature measurement is performed by an on-body unit and communicated to a receiver.

In certain embodiments, the first temperature measurement and/or the second temperature measurement is performed by a receiver.

In certain embodiments, the correction gain is calculated using parameter adaptation.

In certain embodiments, the correction gain is calculated using MIT adaptation.

In certain embodiments, the correction factor is applied to the first ambient-compensated temperatures.

In certain embodiments, the memory includes instructions that, when executed by the processor, cause the processor to sample, at the first sampling rate, second temperatures measured from a second temperature sensor; and determine second ambient-compensated temperatures with the second temperature measurements. The correction factor is calculated by performing windowed comparisons between the first ambient-compensated temperatures and the second ambient-compensated temperatures, such that the correction factor is based on a set of recent pairs of first ambient-compensated temperatures and second ambient-compensated temperatures.

In certain embodiments, the first temperature sensor is disposed at a skin-contacting surface of an on-body unit and the second temperature sensor is disposed on a printed circuit board of the on-body unit.

In certain embodiments, the memory includes instructions that, when executed by the processor, cause the processor to receive analyte data (e.g., a sensor signal from the in vivo analyte sensor); and determine a temperature-compensated analyte sensor signal with the ambient-compensated temperature.

In certain embodiments, the memory includes instructions that, when executed by the processor, cause the processor to determine, with the processor, an analyte level based on the temperature-compensated analyte sensor signal.

In certain embodiments, the first temperature sensor is disposed at a skin-contacting surface of an on-body unit and the second temperature sensor is disposed on a printed circuit board of the on-body unit.

In some aspects of the present disclosure, computer systems are provided that include a processor; and memory communicably coupled to the first processor. The memory includes instructions stored therein that, when executed by the processor, cause the processor to receive sensor data (e.g., detect a first sensor signal) from a first electrode on the in vivo analyte sensor; receive additional sensor data (e.g., detect a second sensor signal) from a second electrode on the in vivo analyte sensor, wherein the first electrode and second electrode include different sensing chemistries with different temperature dependencies; and determine a compensated temperature at the two working electrodes based on the difference between the temperature dependencies for the different sensing chemistries on the two working electrodes.

In certain embodiments, the computer systems include an in vivo analyte sensor, at least one temperature sensor, a sensor electronics unit that receives analyte data from the in vivo analyte sensor, and a receiver unit that receives analyte data from the sensor electronics unit.

In certain embodiments, the compensated temperature is determined by an on-body unit.

In certain embodiments, the memory includes instructions that, when executed by the processor, cause the processor to determine an analyte level based on the temperature-compensated analyte sensor signal.

In certain embodiments, the compensated temperature is determined by an on-body unit and communicated to a receiver.

In certain embodiments, the temperature is determined based on a ratio of the first sensor signal and the second sensor signal.

In certain embodiments, the temperature is determined based on a predetermined temperature, sensor areas, quantity of sensing materials, and efficiencies of the sensing chemistries, and diffusion controlling membrane.

In certain embodiments, the memory includes instructions that, when executed by the processor, cause the processor to determining a temperature-compensated analyte sensor signal with the compensated temperature.

In certain embodiments, the memory includes instructions that, when executed by the processor, cause the processor to determine an analyte level based on the temperature-compensated analyte sensor signal.

In certain embodiments, the compensated temperature is determined by an on-body unit and communicated to a receiver.

In certain embodiments, the temperature-compensated analyte sensor signal is determined with the first sensor signal and not the second sensor signal.

In certain embodiments, the temperature-compensated analyte sensor signal is determined with the second sensor signal and not the first sensor signal.

In certain embodiments, the temperature-compensated analyte sensor signal is determined with both the first sensor signal and the second sensor signal.

In certain embodiments, the first electrode includes a first plurality of sensing elements on the in vivo analyte sensor and the second electrode includes a second plurality of sensing elements disposed on the in vivo analyte sensor.

In some aspects of the present disclosure, computer-implemented methods of determining an analyte level by compensating for ambient temperature using a temperature sensor are provided. The computer-implemented method include receiving analyte data (e.g., a sensor signal derived from an in vivo analyte sensor); receiving temperature data (e.g., detecting a temperature measurement from a temperature sensor); determining, with a processor, whether a threshold requirement is exceeded based on the temperature measurement; and determining, with the processor, a temperature-compensated analyte sensor signal. When the threshold requirement is not exceeded, the temperature-compensated analyte sensor signal is determined using the temperature measurement. Only when the threshold requirement is exceeded, the temperature-compensated analyte sensor signal is determined using an ambient-compensated temperature that is derived by compensating the temperature measurement for ambient temperature.

In certain embodiments, the computer-implemented methods include determining an analyte level based on the temperature-compensated analyte sensor signal.

In certain embodiments, the temperature sensor is coupled to an on-body unit including the in vivo analyte sensor.

In certain embodiments, the temperature measurement represents skin temperature.

In certain embodiments, the ambient-compensated temperature is derived by adding a correction factor to the temperature measurement.

In certain embodiments, the analyte is glucose.

In certain embodiments, the threshold requirement includes an upper threshold value, and wherein adding a correction factor decreases the temperature measurement when the upper threshold value is exceeded.

In certain embodiments, the threshold requirement includes a lower threshold value, and wherein adding a correction factor increases the temperature measurement when the lower threshold value is exceeded.

In certain embodiments, the threshold requirement includes an upper threshold value and a lower threshold value, and wherein adding a correction factor decreases the temperature measurement when the upper threshold value is exceeded and increases the temperature measurement when the lower threshold value is exceeded.

In certain embodiments, the threshold requirement is exceeded when a value of the temperature measurement exceeds the threshold requirement.

In certain embodiments, the threshold requirement is exceeded when a rate-of-change of the temperature measurement exceeds the threshold requirement.

In some aspects of the present disclosure, computer-implemented methods of compensating for ambient temperature using a temperature sensor are provided. The computer-implemented methods include receiving temperature data (e.g., detecting a temperature measurement from a temperature sensor); and determining, with a processor, an ambient-compensated temperature from the temperature measurement using an offset term.

In certain embodiments, the computer-implemented methods include receiving analyte data (e.g., a sensor signal from an in vivo analyte sensor); and determining, with a processor, a temperature-compensated analyte sensor signal with the ambient-compensated temperature.

In certain embodiments, the computer-implemented methods include determining an analyte level based on the temperature-compensated analyte sensor signal.

In certain embodiments, the offset term that is based on a predetermined core body temperature.

In certain embodiments, the predetermined core body temperature is between 36° C. and 38° C.

In certain embodiments, the predetermined core body temperature is approximately 37° C.

In some aspects of the present disclosure, computer-implemented methods of compensating for ambient temperature using temperature sensors are provided. The computer-implemented methods include receiving temperature data (e.g., sampling at a first sampling rate, with a processor, first temperature measurements from a first temperature sensor on an on-body sensor); determining, with a processor, first ambient-compensated temperatures from the first temperature measurements; and determining, with a processor, final ambient-compensated temperatures by applying a correction gain or factor to the first ambient-compensated temperatures. The correction gain or factor changes value at a slower rate than the sampling rate.

In certain embodiments, the correction gain is applied to the first ambient-compensated temperatures.

In certain embodiments, the computer-implemented methods include receiving second sensor data (e.g., sampling at the first sampling rate, with a processor, second temperature measurements from a second temperature sensor on the on-body sensor); and determining, with a processor, second ambient-compensated temperatures with the second temperature measurements. The correction gain is calculated by performing a moving average between first ambient-compensated temperatures and second ambient-compensated temperatures, such that the correction gain is based on a set of recent pairs of first ambient-compensated temperatures and second ambient-compensated temperatures.

In certain embodiments, one or more of the processor sampling first temperatures at a first sampling rate, the processor determining first ambient-compensated temperatures, the processor determining final ambient compensated temperatures, the processor sampling second temperatures at the first sampling rate, and the processor determining the second ambient-compensated temperature are different processors.

In certain embodiments, the sampling of first temperatures at a first rate, the determining of first ambient-compensated temperatures, the determining of final ambient compensated temperatures, the determining of final ambient compensated temperatures, the sampling of second temperatures at the first sampling rate, and the determining of the second ambient-compensated temperature are each performed by either a processor coupled to an on-body unit including an in vivo analyte sensor or by a processor coupled to a receiver that communicates with the on-body unit.

In certain embodiments, the correction gain is calculated using parameter adaptation.

In certain embodiments, the parameter adaptation is MIT adaptation.

In certain embodiments, the correction factor is applied to the first ambient-compensated temperatures.

In certain embodiments, the computer-implemented methods include sampling at the first sampling rate, with a processor, second temperatures measured from a second temperature sensor on the on-body sensor; and determining, with a processor, second ambient-compensated temperatures with the second temperature measurements. The correction factor is calculated by performing windowed comparisons between the first ambient-compensated temperatures and the second ambient-compensated temperatures, such that the correction factor is based on a set of recent pairs of first ambient-compensated temperatures and second ambient-compensated temperatures.

In some aspects of the present disclosure, computer-implemented methods are provided that receive sensor data (e.g., a first sensor signal from a first electrode on an in vivo analyte sensor on an on-body sensor); receive additional sensor data (e.g., a second sensor signal from a second electrode on the in vivo analyte sensor); and determine a compensated temperature at the two working electrodes based on the difference between the temperature dependencies for the different sensing chemistries on the two working electrodes. The first electrode and second electrode include different sensing chemistries with different temperature dependencies.

In certain embodiments, the temperature is determined based on a ratio of the first sensor signal and the second sensor signal.

In certain embodiments, the temperature is determined based on a predetermined temperature, sensor areas, quantity of sensing materials, and efficiencies of the sensing chemistries, and diffusion controlling membrane.

In certain embodiments, the computer-implemented methods include determining, with a processor, a temperature-compensated analyte sensor signal with the compensated temperature.

In certain embodiments, the computer-implemented methods include determining an analyte level based on the temperature-compensated analyte sensor signal.

In certain embodiments, the temperature-compensated analyte sensor signal is determined with the first sensor signal and not the second sensor signal.

In certain embodiments, the temperature-compensated analyte sensor signal is determined with the second sensor signal and not the first sensor signal.

In certain embodiments, the temperature-compensated analyte sensor signal is determined with both the first sensor signal and the second sensor signal.

In certain embodiments, the first electrode includes a first plurality of sensing elements on the in vivo analyte sensor and the second electrode includes a second plurality of sensing elements disposed on the in vivo analyte sensor.

Various other modifications and alterations in the structure and method of operation of this disclosure will be apparent to those skilled in the art without departing from the scope and spirit of the embodiments of the present disclosure. Although the present disclosure has been described in connection with particular embodiments, it should be understood that the present disclosure as claimed should not be unduly limited to such particular embodiments. It is intended that the following claims define the scope of the present disclosure and that structures and methods within the scope of these claims and their equivalents be covered thereby.

It should be understood that techniques introduced above can be implemented by programmable circuitry programmed or configured by software and/or firmware, or they can be implemented entirely by special-purpose "hardwired" circuitry, or in a combination of such forms. Such special-purpose circuitry (if any) can be in the form of, for example, one or more application-specific integrated circuits (ASICS), programmable logic devices (PLDs), field-programmable gate arrays (FPGAs), etc.

Software or firmware implementing the techniques introduced herein may be stored on a machine-readable storage medium and may be executed by one or more general-purpose or special-purpose programmable microprocessors. A "machine-readable medium", as the term is used herein, includes any mechanism that can store information in a form accessible by a machine (a machine may be, for example, a computer, network device, cellular phone, personal digital assistant (PDA), manufacturing took, any device with one or more processors, etc.). For example, a machine-accessible medium includes recordable/non-recordable media (e.g., read-only memory (ROM); random access memory (RAM); magnetic disk storage media; optical storage media; flash memory devices; etc.), etc.

The term "logic", as used herein, can include, for example, special purpose hardwired circuitry, software and/or firmware in conjunction with programmable circuitry, or a combination thereof.

What is claimed is:

1. A method of determining an analyte level by compensating for ambient temperature using a single temperature sensor, the method comprising:
   receiving a sensor signal derived from an in vivo analyte sensor;
   detecting a temperature measurement from a temperature sensor;
   determining, with a processor, whether a threshold requirement is exceeded based on the temperature measurement; and
   determining, with the processor, a temperature-compensated analyte sensor signal;
   wherein when the threshold requirement is not exceeded, the temperature-compensated analyte sensor signal is determined using the temperature measurement; and
   wherein when the threshold requirement is exceeded, the temperature-compensated analyte sensor signal is always determined using an ambient-compensated temperature that is derived by compensating the temperature measurement for ambient temperature.

2. The method of claim 1, wherein the ambient-compensated temperature is derived by adding a correction factor to the temperature measurement.

3. The method of claim 1, wherein the analyte is glucose.

4. The method of claim 1, wherein the threshold requirement is exceeded when a value of the temperature measurement exceeds the threshold requirement.

5. The method of claim 1, wherein the threshold requirement is exceeded when a rate-of-change of the temperature measurement exceeds the threshold requirement.

6. The method of claim 1, further comprising determining analyte concentration based on the temperature-compensated analyte sensor signal.

7. The method of claim 6, further comprising displaying the analyte concentration on a display.

8. The method of claim 7, wherein when the temperature measurement falls within a first predetermined range, the method comprises displaying temperature uncompensated analyte concentration on the display.

9. The method of claim 7, wherein when the temperature measurement falls within a second predetermined range, the method comprises displaying temperature compensated analyte concentration on the display.

10. An analyte monitoring device, comprising:
    a housing;
    a processor coupled to the housing;
    wherein an in vivo analyte sensor is communicably coupled to the processor;
    wherein a temperature sensor is communicably coupled to the processor;
    memory communicably coupled to the processor, wherein the memory includes instructions stored therein that, when executed by the processor, cause the processor to:
    receive a sensor signal from the in vivo analyte sensor;
    detect a temperature measurement from the temperature sensor; determine whether a threshold requirement is exceeded based on the temperature measurement; and
    determine a temperature-compensated analyte sensor signal;
    wherein when the threshold requirement is not exceeded, the temperature-compensated analyte sensor signal is determined using the temperature measurement; and
    wherein when the threshold requirement is exceeded, the temperature-compensated analyte sensor signal is always determined using an ambient-compensated temperature that is derived by compensating the temperature measurement for ambient temperature.

11. The analyte monitoring device of claim 10, wherein the ambient-compensated temperature is derived by adding a correction factor to the temperature measurement.

12. The analyte monitoring device of claim 10, wherein the analyte is glucose.

13. The analyte monitoring device of claim 10, wherein the threshold requirement is exceeded when a value of the temperature measurement exceeds the threshold requirement.

14. The analyte monitoring device of claim 10, wherein the threshold requirement is exceeded when a rate-of-change of the temperature measurement exceeds the threshold requirement.

15. An analyte monitoring system, comprising:
    an on-body unit, comprising:
      a first processor and first memory communicably coupled to the first processor;
      an in vivo analyte sensor communicably coupled to the first processor; and
      a temperature sensor communicably coupled to the first processor; and
    a receiver configured to communicate with the on-body unit, the receiver comprising:
      a second processor and second memory communicably coupled to the second processor;
    wherein at least one of the first memory and second memory includes instructions stored therein that, when executed by at least one of the first and second processors, cause the at least one first and second processor to:
    receive a sensor signal from the in vivo analyte sensor;
    detect a temperature measurement from the temperature sensor;

determine whether a threshold requirement is exceeded based on the temperature measurement; and determine a temperature-compensated analyte sensor signal;

wherein when the threshold requirement is not exceeded, the temperature-compensated analyte sensor signal is determined using the temperature measurement; and wherein when the threshold requirement is exceeded, the temperature-compensated analyte sensor signal is always determined using an ambient-compensated temperature that is derived by compensating the temperature measurement for ambient temperature.

16. The analyte monitoring system of claim 15, wherein the ambient-compensated temperature is derived by adding a correction factor to the temperature measurement.

* * * * *